(12) United States Patent
Torgov et al.

(10) Patent No.: US 8,609,092 B2
(45) Date of Patent: Dec. 17, 2013

(54) ANTIBODY DRUG CONJUGATES (ADC) THAT BIND TO 161P2F10B PROTEINS

(75) Inventors: Michael Torgov, Santa Monica, CA (US); Robert Kendall Morrison, Santa Monica, CA (US); Aya Jakobovits, Beverly Hills, CA (US); Jean Gudas, Los Angeles, CA (US); Zili An, Santa Monica, CA (US)

(73) Assignee: Agensys, Inc., Santa Monica, CA (US)

( * ) Notice: Subject to any disclaimer, the term of this patent is extended or adjusted under 35 U.S.C. 154(b) by 246 days.

(21) Appl. No.: 13/022,905

(22) Filed: Feb. 8, 2011

(65) Prior Publication Data

US 2011/0217321 A1   Sep. 8, 2011

Related U.S. Application Data

(60) Provisional application No. 60/302,489, filed on Feb. 8, 2010.

(51) Int. Cl.
*A61K 39/395* (2006.01)
*A61P 35/00* (2006.01)
*C07K 16/18* (2006.01)
*A61N 5/00* (2006.01)
*C12N 5/09* (2010.01)

(52) U.S. Cl.
USPC ............... 424/133.1; 424/178.1; 530/391.7

(58) Field of Classification Search
USPC ..................... 424/133.1, 178.1; 530/391.7
See application file for complete search history.

(56) References Cited

U.S. PATENT DOCUMENTS

| | | | |
|---|---|---|---|
| 5,001,225 A | 3/1991 | Taylor | |
| 6,323,321 B1 | 11/2001 | Buhring | |
| 6,342,219 B1 | 1/2002 | Thorpe et al. | |
| 6,949,346 B2 | 9/2005 | Buhring et al. | |
| 7,067,130 B2 | 6/2006 | Challita-Eid et al. | |
| 7,226,594 B2 | 6/2007 | Jakobovits et al. | |
| 7,405,290 B2 | 7/2008 | Challita-Eid et al. | |
| 7,427,399 B2* | 9/2008 | Jakobovits et al. | 424/138.1 |
| 7,811,565 B2 | 10/2010 | Jakobovits et al. | |
| 8,236,310 B2 | 8/2012 | Jakobovits et al. | |
| 8,350,009 B2 | 1/2013 | Jakobovits et al. | |
| 2002/0137139 A1 | 9/2002 | Byatt et al. | |
| 2003/0165505 A1 | 9/2003 | Challita-Eid et al. | |
| 2003/0191073 A1 | 10/2003 | Challita-Eid et al. | |
| 2003/0206905 A1 | 11/2003 | Challita-Eid et al. | |
| 2005/0055733 A1 | 3/2005 | Sun et al. | |
| 2005/0265921 A1 | 12/2005 | Challita-Eid et al. | |
| 2005/0265924 A1 | 12/2005 | Challita-Eid et al. | |
| 2006/0002993 A1 | 1/2006 | Challita-Eid et al. | |
| 2006/0088823 A1 | 4/2006 | Haab et al. | |
| 2006/0233794 A1 | 10/2006 | Law et al. | |
| 2006/0275211 A1 | 12/2006 | Jakobovits et al. | |
| 2007/0004913 A1 | 1/2007 | Challita-Eid et al. | |
| 2007/0031335 A1 | 2/2007 | Jakobovits et al. | |
| 2009/0022663 A1* | 1/2009 | Jakobovits et al. | 424/1.49 |

FOREIGN PATENT DOCUMENTS

| | | |
|---|---|---|
| WO | WO-99/60164 | 11/1999 |
| WO | WO-00/21990 | 4/2000 |
| WO | WO-01/57272 | 8/2001 |
| WO | WO-01/57273 | 8/2001 |
| WO | WO-01/57274 | 8/2001 |
| WO | WO-01/57275 | 8/2001 |
| WO | WO-01/57276 | 8/2001 |
| WO | WO-01/57277 | 8/2001 |
| WO | WO-01/57278 | 8/2001 |
| WO | WO-01/60860 | 8/2001 |
| WO | WO-01/75067 | 10/2001 |
| WO | WO-01/86003 | 11/2001 |
| WO | WO-02/079411 | 10/2002 |
| WO | WO-03/004514 | 1/2003 |
| WO | WO-03/016475 | 2/2003 |
| WO | WO-03/040340 | 5/2003 |
| WO | WO-03/048779 | 6/2003 |

OTHER PUBLICATIONS

Jeffrey et al. (Bioconjugate Chem 17:831-840 (2006)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-161 (2009)).*
Alcocer et al., J. Agric. Food Chem (2000) 48:4053-4059.
Amalfitano et al., Current Gene Therapy (2002) 2:111-133.
Andoh et al., "Genomic structure and promoter analysis of the ecto-phosphodiesterase I gene (PDNP3) expressed in glial cells," Biochimica et Biophysica Acta (1999) 1446(3):213-224.
Boehringer Mannheim Biochemicals, 1994 Catalog, p. 93.
Bollen et al., "Nucleotide pyrophosphatases/phosphodiesterases on the move," Critical Reviews in Biochemistry and Molecular Biology (2000) 35(6):393-432.
Buehring et al., Tissue Antigens (2000) 55(Suppl. 01):68.
Buhring et al., Blood 94(7):2343-2356 (1999).
Buhring et al., Blood 97(10):3303-3305 (2001).
Burgess et al., Journal of Cell Biology 111:2129-2138 (1990).
Colbern et al., J. Inorg. Biochem. (1999) 77:117-120.
Coleman, Research in Immunology 145:33-36 (1994).
Database EMBL [Online] Accession No. AK024899 (Sep. 29, 2000).
Database Geneseq [Online] Accession No. ADE56103 (Jan. 29, 2005).
Deissler et al., Journal of Biological Chemistry (1995) 270(17):9849-9855.
Dennis, Nature (2006) 442:739-741.
Dillman, Annals of Internal Medicine (1989) 111:592-603.
Goding et al., Biochimica et Biophysica Acta (2003) 1638(1):1-19.
Houdebine, Journal of Biotechnology (1994) 34:269-287.

(Continued)

*Primary Examiner* — Lynn Bristol

(74) *Attorney, Agent, or Firm* — Morrison & Foerster LLP

(57) ABSTRACT

Antibody drug conjugates (ADC's) that bind to 161P2F10B protein are described herein. 161P2F10B exhibits tissue specific expression in normal adult tissue, and is aberrantly expressed in the cancers listed in Table I. Consequently, the ADC's of the invention provide a therapeutic composition for the treatment of cancer.

5 Claims, 22 Drawing Sheets

(56) References Cited

OTHER PUBLICATIONS

Houghton and Scheinberg, Seminars in Oncology (1986) 13:165-179.
International Search Report for PCT/US02/36002, mailed on Jan. 5, 2005, 5 pages.
International Search Report and Written Opinion for PCT/US06/12314, mailed Jan. 11, 2008, 7 pages.
Jain, Scientific American (1994) 271:58-65.
Jiang et al., J. Biol. Chem. (2005) 280(6):4656-4662.
Jin-Hua et al., Genomics 45(2):412-415 (1997).
Lazar et al., Molecular and Cellular Biology 8(3):1247-1252 (1988).
Lederman et al., Molecular Immunology 28:1171-1181 (1991).
Lewin, ed., Genes VI, Chapter 29, pp. 847-848 (1997).
Li et al., Proc Natl Acad Sci USA 77:3211-3214 (1980).
Maurice et al., "Biosynthesis and intracellular transport of a bile canalicular plasma membrane protein: studies in vivo and in the perfused rat liver," Hepatology (1994) 19(3):648-655.
Maurice et al., "Characterization of rat hepatocyte plasma membrane domains by monoclonal antibodies," European Journal of Cell Biology (1985) 39(1):122-129.
McCormick, Nature Reviews (2001) 1:130-141.
Meibohm, ed., Pharmacokinetics and Pharmacodynamics of Biotech Drugs, Wiley-VHC, 2006, Chapter 3, pp. 45-91.
NCBI Accession No. NP_004439, Version: NP_004439.1, GI:4758298, PRI date: Oct. 14, 1999, pp. 1-4.
Pandha et al., Current Opinion in Investigational Drugs (2000) 1:122-134.
Paul (Ed.), Fundamental Immunology, 3rd ed., p. 242 (1993).
PN IM3575, 100 tests, 20 µL/test, IOTest Conjugated Antibodies, Immunotech, A Coulter Company, Vers. 01, Apr. 4, 2001, retrieved from Internet.
Reiger et al., Glossary of Genetics and Cytogenetics, Classical and Molecular, 4th Ed., Springer-Verlag, Berlin (1976).
Rolland, Advanced Drug Delivery Reviews (2005) 57:669-673.
Schwartz et al., Proc Natl Acad Sci USA 84:6408-6411 (1987).
Scott et al., "Biochemical and molecular identification of distinct forms of alkaline phosphodiesterase I expressed on the apical and basolateral plasma membrane surfaces of rat hepatocytes," Hepatology (1997) 25(4):995-1002.
Srivastava, Nature Immunology (2000) 1(5):363-366.
Stancoviski et al., PNAS USA (1991) 88:8691-8695.
Supplementary Partial European Search Report for EP 02 79 7088.8, mailed on Oct. 25, 2006, 7 pages.
Supplementary European Search Report for EP 02 79 7088, mailed on Feb. 5, 2007, 8 pages.
Supplementary European Search Report for EP 06749164.7, mailed Aug. 20, 2009, 12 pages.
Verma et al., Nature (1997) 389:239-242.
Weiner, Seminars in Oncology (1999) 26(Suppl. 12):41-50.
White et al., Ann Rev Med (2001) 52:125-145.
Yano et al., Cancer Letters (2004) 207(2):139-147.
Yano et al., International Journal of Molecular Medicine (2003) 12(5):763-766.
Restriction Requirement for U.S. Appl. No. 10/005,480, mailed on May 24, 2004.
Response to Restriction Requirement and Amendment Under 37 CFR § 1.111 for U.S. Appl. No. 10/005,480, filed on Jun. 18, 2004.
Non-Final Office Action for U.S. Appl. No. 10/005,480, mailed on Aug. 17, 2004.
Restriction Requirement for U.S. Appl. No. 10/062,109, mailed on Jul. 9, 2004.
Response to Restriction Requirement for U.S. Appl. No. 10/062,109, filed on Jul. 15, 2004.
Non-Final Office Action for U.S. Appl. No. 10/062,109, mailed on Aug. 25, 2004.
Amendment in Response to Non-Final Office Action for U.S. Appl. No. 10/062,109, filed on Sep. 17, 2004.
Final Office Action for U.S. Appl. No. 10/062,109, mailed on Nov. 12, 2004.
Amendment After Final Action (37 CFR § 1.116) for U.S. Appl. No. 10/062,109, filed on Dec. 1, 2004.
Request for Continued Examination from U.S. Appl. No. 10/062,109, filed via facsimile on Mar. 2, 2005.
Notice of Allowance for U.S. Appl. No. 10/062,109, mailed on May 4, 2005.
Non-Final Office Action for U.S. Appl. No. 10/860,769, mailed on Dec. 5, 2006.
Amendment in Response to Non-Final Office Action for U.S. Appl. No. 10/860,769, filed on Mar. 5, 2007.
Notice of Allowance and Fee(s) Due from U.S. Appl. No. 10/860,769, mailed Jun. 1, 2007.
Non-Final Office Action for U.S. Appl. No. 10/859,643, mailed on Nov. 13, 2006.
Amendment in Response to Non-Final Office Action for U.S. Appl. No. 10/859,643, filed on Mar. 5, 2007.
Notice of Allowance and Fee(s) Due from U.S. Appl. No. 10/859,643, mailed Jun. 8, 2007.
Non-Final Office Action for U.S. Appl. No. 11/097,912, mailed on Nov. 6, 2006.
Amendment in Response to Non-Final Office Action from U.S. Appl. No. 11/097,912, filed via EFS-Web on May 4, 2007.
Non-Final Office Action (2nd) from U.S. Appl. No. 11/097,912, mailed Jun. 27, 2007.
Amendment in Response to Non-Final Office Action (2nd) from U.S. Appl. No. 11/097,912, filed via EFS-Web on Dec. 13, 2007.
Non-Final Office Action for U.S. Appl. No. 11/097,864, mailed on Oct. 19, 2006.
Amendment in Response to Non-Final Office Action from U.S. Appl. No. 11/097,864, filed via EFS-Web on Apr. 17, 2007.
Final Office Action from U.S. Appl. No. 11/097,864, mailed Jun. 27, 2007.
Request for Continued Examination from U.S. Appl. No. 11/097,864, filed via EFS-Web on Oct. 30, 2007.
Restriction Requirement for U.S. Appl. No. 10/291,241, mailed on Sep. 21, 2005.
Response to Restriction Requirement for U.S. Appl. No. 10/291,241, filed on Nov. 18, 2005.
Non-Final Office Action for U.S. Appl. No. 10/291,241, mailed on Dec. 29, 2005.
Amendment in Response to Non-Final Office Action for U.S. Appl. No. 10/291,241, filed on Jan. 10, 2006.
Final Office Action for U.S. Appl. No. 10/291,241, mailed on Apr. 5, 2006.
Amendment After Final Action (37 CFR § 1.116) for U.S. Appl. No. 10/291,241, filed on Apr. 19, 2006.
Advisory Action Before the Filing of an Appeal Brief from U.S. Appl. No. 10/291,241, mailed May 19, 2006.
Supplemental Amendment After Final Action (37 CFR § 1.116) for U.S. Appl. No. 10/291,241, filed on Jun. 1, 2006.
Non-Final Office Action for U.S. Appl. No. 10/291,241, mailed on Jun. 28, 2006.
Amendment in Response to Non-Final Office Action for U.S. Appl. No. 10/291,241, filed on Jul. 13, 2006.
Notice of Allowance and Fee(s) Due from U.S. Appl. No. 10/291,241, mailed Oct. 4, 2006.
Notice of Allowance for U.S. Appl. No. 10/291,241, mailed on Dec. 12, 2006.
Restriction Requirement for U.S. Appl. No. 11/396,178, mailed on Feb. 27, 2007.
Non-Final Office Action for U.S. Appl. No. 11/655,822, mailed on Aug. 6, 2008, 19 pages.
Non-Final Office Action for U.S. Appl. No. 11/655,822, mailed on Feb. 23, 2009, 10 pages.
Non-Final Office Action for U.S. Appl. No. 12/196,039, mailed on May 13, 2009, 13 pages.
Non-Final Office Action for U.S. Appl. No. 12/641,261 mailed Jul. 21, 2010, 15 pages.
International Search Report for PCT/US11/24055, mailed on Apr. 6, 2011, 3 pages.

(56) References Cited

OTHER PUBLICATIONS

Written Opinion of the International Searching Authority for PCT/US11/24055, mailed on Apr. 6, 2011, 4 pages.
Johnstone and Thorpe, Immunochemistry in Practice, 2nd Ed., Blackwell Scientific Publications, Oxford (1987) pp. 49-50.
Maynard et al., "Antibody Engineering," Annu. Rev. Biomed. Eng. (2000) 2:339-376.
HUGO Gene Nomenclature Committee, "ENPP3", printed Mar. 8, 2012.
STIC sequence search for SEQ ID No. 17, Uniprot database, Result #1 in "Search Result 20120306_142638_us-13-153-336a-17.rup" Mar. 6, 2012.
Han et al., "Fine epitope mapping of monoclonal antibodies against hemagglutinin of a highly pathogenic H5N1 influenza virus using yeast surface display", Biochemical and Biophysical Research Communications (2011) 409:253-259.
Green, "Antibody engineering via genetic engineering of the mouse: XenoMouse strains are a vehicle for the facile generation of therapeutic human monoclonal antibodies," Journal of Immunological Methods (1999) 231:11-23.

* cited by examiner

Figure 1: The cDNA (SEQ ID NO:1) and amino acid sequence (SEQ ID NO:2) of 161P2F10B variant 2. The 3858 nucleotide sequence of 161P2F10B variant 2 is shown.

```
     1                                            M  E  S  T  L  T
   1 ctactttattctgataaaacaggtctatgcagctaccaggacaATGGAATCTACGTTGAC
   7  L  A  T  F  Q  P  V  K  K  N  T  L  K  K  Y  K  T  A  C  T
  61 TTTAGCAACGGAACAACCTGTTAAGAAGAACACTCTTAAGAAATATAAAATAGCTTGCAT
  27  V  L  L  A  L  L  V  I  M  S  L  G  L  G  L  G  L  G  L  R
 121 TGTTCTTCTTGCTTTGCTGGTGATCATGTCACTTGGATTAGGCCTGGGGCTTGGACTCAG
  47  K  L  E  K  Q  G  S  C  R  K  K  C  F  D  A  S  F  R  G  L
 181 GAAACTGGAAAAGCAAGGCAGCTGCAGGAAGAAGTGCTTTGATGCATCATTTAGAGGACT
  67  E  N  C  R  C  D  V  A  C  K  D  R  G  D  C  C  W  D  F  E
 241 GGAGAACTGCCGGTGTGATGTGGCATGTAAAGACCGAGGTGATTGCTGCTGGGATTTTGA
  87  D  T  C  V  E  S  T  R  I  W  M  C  N  K  F  R  C  G  E  T
 301 AGACACCTGTGTGGAATCAACTCGAATATGGATGTGCAATAAATTTCGTTGTGGAGAGAC
 107  R  L  E  A  S  L  C  S  C  S  D  D  C  L  Q  R  K  D  C  C
 361 CAGATTAGAGGCCAGCCTTTGCTCTTGTTCAGATGACTGTTTGCAGAGGAAAGATTGCTG
 127  A  D  Y  K  S  V  C  Q  G  E  T  S  W  L  E  N  C  D  T
 421 TGCTGACTATAAGAGTGTTTGCCAAGGAGAAACCTCATGGCTGGAAGAAAACTGTGACAC
 147  A  Q  Q  S  Q  C  P  E  G  F  D  L  P  P  V  I  L  F  S  M
 481 AGCCCAGCAGTCTCAGTGCCCAGAAGGGTTTGACCTGCCACCAGTTATCTTGTTTTCTAT
 167  D  G  F  R  A  E  Y  L  Y  T  W  D  T  L  M  P  N  I  N  K
 541 GGATGGATTTAGAGCTGAATATTTATACACATGGGATACTTTAATGCCAAATATCAATAA
 187  L  K  T  C  G  I  H  S  K  Y  M  R  A  M  Y  P  T  K  T  F
 601 ACTGAAAACATGTGGAATTCATTCAAAATACATGAGAGCTATGTATCCTACCAAAACCTT
 207  P  N  H  Y  T  I  V  T  G  L  Y  P  E  S  H  G  I  I  D  N
 661 CCCAAATCATTACACCATTGTCACGGGCTTGTATCCAGAGTCACATGGCATCATTGACAA
 227  N  M  Y  D  V  N  L  N  K  N  F  S  L  S  S  K  E  Q  N  N
 721 TAATATGTATGATGTAAATCTCAACAAGAATTTTTCACTTTCTTCAAAGGAACAAAATAA
 247  P  A  W  W  H  G  Q  P  M  W  L  T  A  M  Y  Q  G  L  K  A
 781 TCCAGCCTGGTGGCATGGGCAACCAATGTGGCTGACAGCAATGTATCAAGGTTTAAAAGC
 267  A  T  Y  F  W  P  G  S  E  V  A  I  N  G  S  F  P  S  I  Y
 841 CGCTACCTACTTTTGGCCCGGATCAGAAGTGGCTATAAATGGCTCCTTTCCTTCCATATA
 287  M  P  Y  N  G  S  V  P  F  E  E  R  I  S  T  L  L  K  W  L
 901 CATGCCTTACAACGGAAGTGTCCCATTTGAAGAGAGGATTTCTACACTGTTAAAATGGCT
 307  D  L  P  K  A  E  R  P  R  F  Y  T  M  Y  F  E  E  P  D  S
 961 GGACCTGCCCAAAGCTGAAAGACCCAGGTTTTATACCATGTATTTTGAAGAACCTGATTC
 327  S  G  H  A  G  G  P  V  S  A  R  V  I  K  A  L  Q  V  V  D
1021 CTCTGGACATGCAGGTGGACCAGTCAGTGCCAGAGTAATTAAAGCCTTACAGGTAGTAGA
 347  H  A  F  G  M  L  M  E  G  L  K  Q  R  N  L  H  N  C  V  N
1081 TCATGCTTTTGGGATGTTGATGGAAGGCCTGAAGCAGCGGAATTTGCACAACTGTGTCAA
 367  I  I  L  L  A  D  H  G  M  D  Q  T  Y  C  N  K  M  E  Y  M
1141 TATCATCCTTCTGGCTGACCATGGAATGGACCAGACTTATTGTAACAAGATGGAATACAT
 387  T  D  Y  F  P  R  I  N  F  F  Y  M  Y  E  G  P  A  P  R  I
1201 GACTGATTATTTTCCCAGAATAAACTTCTTCTACATGTACGAAGGGCCTGCCCCCCGCAT
```

Figure 1-2

```
 407  R  A  H  N  I  P  H  D  F  F  S  F  N  S  E  E  I  V  R  N
1261  CCGAGCTCATAATATACCTCATGACTTTTTTAGTTTTAATTCTGAGGAAATTGTTAGAAA
 427  L  S  C  R  K  P  D  Q  H  F  K  P  Y  L  T  P  D  L  P  K
1321  CCTCAGTTGCCGAAAACCTGATCAGCATTTCAAGCCCTATTTGACTCCTGATTTGCCAAA
 447  R  L  H  Y  A  K  N  V  R  I  D  K  V  H  L  F  V  D  Q  Q
1381  GCGACTGCACTATGCCAAGAACGTCAGAATCGACAAAGTTCATCTCTTTGTGGATCAACA
 467  W  L  A  V  R  S  K  S  N  T  N  C  G  G  G  N  H  G  Y  N
1441  GTGGCTGGCTGTTAGGAGTAAATCAAATACAAATTGTGGAGGAGGCAACCATGGTTATAA
 487  N  E  F  R  S  M  E  A  I  F  L  A  E  G  P  S  F  K  E  K
1501  CAATGAGTTAGGAGCATGGAGGCTATCTTTCTGGCACATGGACCCAGTTTTAAAGAGAA
 507  T  E  V  P  F  E  N  I  E  V  Y  N  L  M  C  D  L  L  R
1561  GACTGAAGTTGAACCATTTGAAAATATTGAAGTCTATAACCTAATGTGTGATCTTCTACG
 527  I  Q  P  A  P  N  N  G  T  H  G  S  L  N  E  L  L  K  V  P
1621  CATTCAACCAGCACCAAACAATGGAACCCATGGTAGTTTAAACCATCTTCTGAAGGTGCC
 547  F  Y  E  P  S  H  A  E  E  V  S  K  F  S  V  C  G  F  A  N
1681  TTTTTATGAGCCATCCCATGCAGAGGAGGTGTCAAAGTTTTCTGTTTGTGGCTTTGCTAA
 567  P  L  P  T  E  S  L  D  C  F  C  P  E  L  Q  N  S  T  Q  L
1741  TCCATTGCCCACAGAGTCTCTTGACTGTTTCTGCCCTCACCTACAAAATAGTACTCAGCT
 587  E  Q  V  N  Q  M  L  N  L  T  Q  E  E  I  T  A  T  V  K  V
1801  GGAACAAGTGAATCAGATGCTAAATCTCACCCAAGAAGAAATAACAGCAACAGTGAAAGT
 607  N  L  P  F  G  R  P  R  V  L  Q  K  N  V  D  H  C  L  L  Y
1861  AAATTGCCATTTGGGAGGCCTAGGGTACTGCAGAAGAACGTGGACCACTGTCTCCTTTA
 627  H  R  E  Y  V  S  G  F  G  K  A  M  R  M  P  M  W  S  S  Y
1921  CCACAGGGAATATGTCAGTGGATTTGGAAAAGCTATGAGGATGCCCATGTGGAGTTCATA
 647  T  V  P  Q  L  G  D  I  S  P  L  P  P  T  V  P  D  C  L  R
1981  CACAGTCCCCCAGTTGGGAGACACATCGCCTCTGCCTCCCACTGTCCCAGACTGTCTGCG
 667  A  D  V  R  V  P  P  S  E  S  Q  K  C  S  F  Y  L  A  D  K
2041  GGCTGATGTCAGGGTTCCTCCTTCTGAGAGCCAAAAATGTTCCTTCTATTTAGCAGACAA
 687  N  I  T  H  G  F  L  Y  P  P  A  S  N  R  T  S  D  S  Q  Y
2101  GAATATCACCCACGGCTTCCTCTATCCTCCTGCCAGCAATAGAACATCAGATAGCCAATA
 707  D  A  L  I  T  S  N  L  V  P  M  Y  E  E  F  R  K  M  W  D
2161  TGATGCTTTAATTACTAGCAATTTGGTACCTATGTATGAAGAATTCAGAAAAATGTGGGA
 727  Y  F  H  S  V  L  L  I  K  H  A  T  E  R  N  G  V  N  V  V
2221  CTACTTCCACAGTGTTCTTCTTATAAAACATGCCACAGAAAGAAATGGAGTAAATGTGGT
 747  S  G  P  I  F  D  Y  N  Y  D  G  H  F  D  A  P  D  E  I  T
2281  TAGTGGACCAATATTTGATTATAATTATGATGGCCATTTTGATGCTCCAGATGAAATTAC
 767  K  H  L  A  N  T  D  V  P  I  P  T  E  Y  F  V  V  L  T  S
2341  CAAACATTTAGCCAACACTGATGTTCCCATCCCAACACACTACTTTGTGGTGCTGACCAG
 787  C  K  N  K  S  H  T  P  E  N  C  P  G  W  L  D  V  L  P  F
2401  TTGTAAAAACAAGAGCCACACACCGGAAAACTGCCCTGGGTGGCTGGATGTCCTACCCTT
 807  I  I  P  H  R  P  T  N  V  E  S  C  P  E  G  K  P  E  A  L
2461  TATCATCCCTCACCGACCTACCAACGTGGAGAGCTGTCCTGAAGGTAAACCAGAAGCTCT
 827  W  V  E  R  F  T  A  H  I  A  R  V  R  D  V  E  L  L  T
2521  TTGGGTTGAAGAAAGATTTACAGCTCACATTGCCCGGGTCCGTGATGTAGAACTTCTCAC
 847  G  L  D  F  Y  Q  D  K  V  Q  P  V  S  E  I  L  Q  L  K  T
```

Figure 1-3

```
2581 TGGGCTTGACTTCTATCAGGATAAAGTGCAGCCTGTCTCTGAAATTTTGCAACTAAAGAC
 867   Y  L  P  T  F  E  T  T  I  *
2641 ATATTTACCAACATTTGAAACCACTATTTAActtaataatgtctacttaatatataattt
2701 actgtataaagtaattttggcaaaatataagtgatttttctggagaattgtaaaataaa
2761 gttttctattttttccttaaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaaataaataaataaaataaaagtaa
2941 caataaaataaaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagacccttcaagattcaaagttccatttga
3421 cagagcaaaggcacttcgcaagcagaagggttttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaaggagagttttagaaccagcaca
3661 tccactggagatgctgggccaccagacccctcccagtcaataaagtctggtgcctcattt
3721 gatctcagcctcatcatgaccctggagagaccctgataccatctgccagtccccgacagc
3781 ttaggcactccttgccatcaacctgaccccccgagtggttctccaggctccctgccccac
3841 ccattcaggccggaattc
```

Figure 2:

<u>Figure 2A</u>  The cDNA (SEQ ID NO:3) and amino acid sequence (SEQ ID NO:4) of H16-7.8 heavy chain.

```
                                                    M  K  H  L  W  F  F  L  L
   1 TTTCTGAGAGTCCTGGACCTCCTGTGCAAGAACATGAAACACCTGTGGTTCTTCCTCCTG
      L  V  A  A  P  R  W  V  L  S  Q  V  Q  L  Q  E  S  G  P  G
  61 CTGGTGGCAGCTCCCAGATGGGTCCTGTCCCAGGTGCAGCTGCAGGAGTCGGGCCCAGGA
      L  V  K  P  S  Q  T  L  S  L  T  C  T  V  S  G  G  S  I  S
 121 CTGGTGAAGCCTTCACAGACCCTGTCCCTCACCTGCACTGTCTCTGGTGGCTCCATCAGC
      S  G  G  Y  Y  W  S  W  I  R  Q  H  P  G  K  G  L  E  W  I
 181 AGTGGTGGTTACTACTGGAGCTGGATCCGCCAGCACCCAGGGAAGGGCCTGGAGTGGATT
      G  I  I  Y  Y  S  G  S  T  Y  Y  N  P  S  L  K  S  R  V  T
 241 GGGATCATCTATTACAGTGGGAGCACCTACTACAACCCGTCCCTCAAGAGTCGAGTTACC
      I  S  V  D  T  S  K  N  Q  F  S  L  K  L  N  S  V  T  A  A
 301 ATATCAGTAGACACGTCTAAGAACCAGTTCTCCCTGAAGCTGAACTCTGTGACTGCCGCG
      D  T  A  V  F  Y  C  A  R  V  A  I  V  T  T  I  P  G  G  M
 361 GACACGGCCGTGTTTTACTGTGCGAGAGTGGCTATAGTGACTACGATCCCGGGCGGTATG
      D  V  W  G  Q  G  T  T  V  T  V  S  S  A  S  T  K  G  P  S
 421 GACGTCTGGGGCCAAGGGACCACGGTCACCGTCTCCTCAGCCTCCACCAAGGGCCCATCG
      V  F  P  L  A  P  C  S  R  S  T  S  E  S  T  A  A  L  G  C
 481 GTCTTCCCCCTGGCGCCCTGCTCCAGGAGCACCTCCGAGAGCACAGCGGCCCTGGGCTGC
      L  V  K  D  Y  F  P  E  P  V  T  V  S  W  N  S  G  A  L  T
 541 CTGGTCAAGGACTACTTCCCCGAACCGGTGACGGTGTCGTGGAACTCAGGCGCTCTGACC
      S  G  V  H  T  F  P  A  V  L  Q  S  S  G  L  Y  S  L  S  S
 601 AGCGGCGTGCACACCTTCCCAGCTGTCCTACAGTCCTCAGGACTCTACTCCCTCAGCAGC
      V  V  T  V  P  S  S  N  F  G  T  Q  T  Y  T  C  N  V  D  H
 661 GTGGTGACCGTGCCCTCCAGCAACTTCGGCACCCAGACCTACACCTGCAACGTAGATCAC
      K  P  S  N  T  K  V  D  K  T  V  E  R  K  C  C  V  E  C  P
 721 AAGCCCAGCAACACCAAGGTGGACAAGACAGTTGAGCGCAAATGTTGTGTCGAGTGCCCA
      P  C  P  A  P  P  V  A  G  P  S  V  F  L  F  P  P  K  P  K
 781 CCGTGCCCAGCACCACCTGTGGCAGGACCGTCAGTCTTCCTCTTCCCCCCAAAACCCAAG
      D  T  L  M  I  S  R  T  P  E  V  T  C  V  V  V  D  V  S  H
 841 GACACCCTCATGATCTCCCGGACCCCTGAGGTCACGTGCGTGGTGGTGGACGTGAGCCAC
      E  D  P  E  V  Q  F  N  W  Y  V  D  G  V  E  V  H  N  A  K
 901 GAAGACCCCGAGGTCCAGTTCAACTGGTACGTGGACGGCGTGGAGGTGCATAATGCCAAG
      T  K  P  R  E  E  Q  F  N  S  T  F  R  V  V  S  V  L  T  V
 961 ACAAAGCCACGGGAGGAGCAGTTCAACAGCACGTTCCGTGTGGTCAGCGTCCTCACCGTT
      V  H  Q  D  W  L  N  G  K  E  Y  K  C  K  V  S  N  K  G  L
1021 GTGCACCAGGACTGGCTGAACGGCAAGGAGTACAAGTGCAAGGTCTCCAACAAAGGCCTC
      P  A  P  I  E  K  T  I  S  K  T  K  G  Q  P  R  E  P  Q  V
1081 CCAGCCCCCATCGAGAAAACCATCTCCAAAACCAAAGGGCAGCCCCGAGAACCACAGGTG
      Y  T  L  P  P  S  R  E  E  M  T  K  N  Q  V  S  L  T  C  L
1141 TACACCCTGCCCCCATCCCGGGAGGAGATGACCAAGAACCAGGTCAGCCTGACCTGCCTG
      V  K  G  F  Y  P  S  D  I  A  V  E  W  E  S  N  G  Q  P  E
1201 GTCAAAGGCTTCTACCCCAGCGACATCGCCGTGGAGTGGGAGAGCAATGGGCAGCCGGAG
      N  N  Y  K  T  T  P  P  M  L  D  S  D  G  S  F  F  L  Y  S
1261 AACAACTACAAGACCACACCTCCCATGCTGGACTCCGACGGCTCCTTCTTCCTTTACAGC
      K  L  T  V  D  K  S  R  W  Q  Q  G  N  V  F  S  C  S  V  M
1321 AAGCTCACCGTGGACAAGAGCAGGTGGCAGCAGGGGAACGTCTTCTCATGCTCCGTGATG
      H  E  A  L  H  N  H  Y  T  Q  K  S  L  S  L  S  P  G  K  *
1381 CATGAGGCTCTGCACAACCACTACACGCAGAAGAGCCTCTCCCTGTCTCCGGGTAAATAA
```

Figure 2B The cDNA (SEQ ID NO:5) and amino acid sequence (SEQ ID NO:6) of H16-7.8 light chain.

```
                                                      M   L   P   S   Q   L
  1  AGGAGTAGAAAATGAGCAAAACTGACAAGTCAAGGCAGGAAGATGTTGCCATCACAACTC
        I   G   F   L   L   W   V   P   A   S   R   G   E   I   V   L   T   Q   S
 61  ATTGGGTTTCTGCTGCTCTGGGTTCCAGCCTCCAGGGGTGAAATTGTGCTGACTCAGTCT
        P   D   F   Q   S   V   T   P   K   E   K   V   T   I   T   C   R   A   S   Q
121  CCAGACTTTCAGTCTGTGACTCCAAAGGAGAAAGTCACCATCACCTGCCGGGCCAGTCAG
        S   I   G   I   S   L   H   W   Y   Q   Q   K   P   D   Q   S   P   K   L   L
181  AGCATTGGTATTAGCTTACACTGGTACCAGCAGAAACCAGATCAGTCTCCAAAGCTCCTC
        I   K   Y   A   S   Q   S   F   S   G   V   P   S   R   F   S   G   S   G   S
241  ATCAAGTATGCTTCCCAGTCCTTCTCAGGGGTCCCCTCGAGGTTCAGTGGCAGTGGATCT
        G   T   D   F   T   L   T   I   N   S   L   E   A   E   D   A   A   T   Y   Y
301  GGGACAGATTTCACCCTCACCATCAATAGCCTGGAAGCTGAAGATGCTGCAACGTATTAC
        C   H   Q   S   R   S   F   P   W   T   F   G   Q   G   T   K   V   E   I   K
361  TGTCATCAGAGTAGGAGTTTCCCGTGGACGTTCGGCCAAGGGACCAAGGTGGAAATCAAA
        R   T   V   A   A   P   S   V   F   I   F   P   P   S   D   E   Q   L   K   S
421  CGAACTGTGGCTGCACCATCTGTCTTCATCTTCCCGCCATCTGATGAGCAGTTGAAATCT
        G   T   A   S   V   V   C   L   L   N   N   F   Y   P   R   E   A   K   V   Q
481  GGAACTGCCTCTGTTGTGTGCCTGCTGAATAACTTCTATCCCAGAGAGGCCAAAGTACAG
        W   K   V   D   N   A   L   Q   S   G   N   S   Q   E   S   V   T   E   Q   D
541  TGGAAGGTGGATAACGCCCTCCAATCGGGTAACTCCCAGGAGAGTGTCACAGAGCAGGAC
        S   K   D   S   T   Y   S   L   S   S   T   L   T   L   S   K   A   D   Y   E
601  AGCAAGGACAGCACCTACAGCCTCAGCAGCACCCTGACGCTGAGCAAAGCAGACTACGAG
        K   H   K   V   Y   A   C   E   V   T   H   Q   G   L   S   S   P   V   T   K
661  AAACACAAAGTCTACGCCTGCGAAGTCACCCATCAGGGCCTGAGCTCGCCCGTCACAAAG
        S   F   N   R   G   E   C   *
721  AGCTTCAACAGGGGAGAGTGTTAG
```

Figure 3:

Figure 3A The amino acid sequence (SEQ ID NO:7) of H16-7.8 heavy chain.

```
  1  MKHLWFFLLL VAAPRWVLSQ VQLQESGPGL VKPSQTLSLT CTVSGGSISS
 51  GGYYWSWIRQ HPGKGLEWIG IIYYSGSTYY NPSLKSRVTI SVDTSKNQFS
101  LKLNSVTAAD TAVFYCARVA IVTTIPGGMD VWGQGTTVTV SSASTKGPSV
151  FPLAPCSRST SESTAALGCL VKDYFPEPVT VSWNSGALTS GVHTFPAVLQ
201  SSGLYSLSSV VTVPSSNFGT QTYTCNVDHK PSNTKVDKTV ERKCCVECPP
251  CPAPPVAGPS VFLFPPKPKD TLMISRTPEV TCVVVDVSHE DPEVQFNWYV
301  DGVEVHNAKT KPREEQFNST FRVVSVLTVV HQDWLNGKEY KCKVSNKGLP
351  APIEKTISKT KGQPREPQVY TLPPSREEMT KNQVSLTCLV KGFYPSDIAV
401  EWESNGQPEN NYKTTPPMLD SDGSFFLYSK LTVDKSRWQQ GNVFSCSVMH
451  EALHNHYTQK SLSLSPGK
```

Figure 3B The amino acid sequence (SEQ ID NO:8) of H16-7.8 light chain.

```
  1  MLPSQLIGFL LLWVPASRGE IVLTQSPDFQ SVTPKEKVTI TCRASQSIGI
 51  SLHWYQQKPD QSPKLLIKYA SQSFSGVPSR FSGSGSGTDF TLTINSLEAE
101  DAATYYCHQS RSFPWTFGQG TKVEIKRTVA APSVFIFPPS DEQLKSGTAS
151  VVCLLNNFYP REAKVQWKVD NALQSGNSQE SVTEQDSKDS TYSLSSTLTL
201  SKADYEKHKV YACEVTHQGL SSPVTKSFNR GEC
```

Figure 4

Figure 4A Alignment of H16-7.8 Heavy Chain Variable Region (SEQ ID NO:11) to human germline VH4-31/D5-12/JH6

```
                        <-------------------------------------FWR1-------------------------------------
H16-7.8    1    CAGGTGCAGCTGCAGGAGTCGGGCCCAGGACTGGTGAAGCCTTCACAGACCCTGTCCCTCACCTGCACTGTCTCTGGTGG    80
VH4-31     1    ................................................T...........................    80
D5-12           --------------------------------------------------------------------------------
JH6             --------------------------------------------------------------------------------

------>  <-------CDR1------->  <-------------------FWR2------------------->  <--
H16-7.8    81   CTCCATCAGC  AGTGGTGTTACTACTGGAGC  TGGATCCGGCAGCACCCAGGGAAGGGCCTGGAGTGGATTGGG  ATCATCT  160
VH4-31     81   ..........  ....................  .........................................  TA.....  160
D5-12           ----------  --------------------  -----------------------------------------  -------
JH6             ----------  --------------------  -----------------------------------------  -------

--------CDR2-------->  <-----------------------------FWR3-----------------------------
H16-7.8    161  ATTACAGTGGGAGCACCTACTACAACCCGTCCCTCAAGAGT  CGAGTTACCATATCAGTAGACGTCTAAGAACCAGTTC    240
VH4-31     161  .........................................  ....................................    240
D5-12           -----------------------------------------  ------------------------------------
JH6             -----------------------------------------  ------------------------------------

----------------------------------->
H16-7.8    241  TCCCTGAAGCTGAGCTCTGTGACTGCCGCGGACACGGCCGTGTTTTACTGTGCGAGA  GTGGCTATAGTGACTACGATCCC    320
VH4-31     241  .............G...........................................  ....................    298
D5-12      1    ---------------------------------------------------------  ...A........G.......    20
JH6             ---------------------------------------------------------  --------------------

H16-7.8    321  GGGCGGTATGGACGTCTGGGGCCAAGGGACCACGGTCACCGTCTCCTCA    369
VH4-31          -------------------------------------------------
D5-12           -------------------------------------------------
JH6        17   ..............G..................................    62
```

Figure 4(B) Alignment of H16-7.8 Light Chain Variable Region (SEQ ID NO:12) to human germline A26/JK1

```
                         <------------------------------FWR1-----------------------------> <-------
H16-7.8   100  GAAATTGTGCTGACTCAGTCTCCAGACTTTCAGTCTGTGACTCCAAAGGAGAAAGTCACCATCACCTGC CGGGCCAGTCA  179
A26         1  ..........................................................................  ...........   80
JK1

-----CDR1------------>  <-----------------------------FWR2-----------------------> <-------CDR2
H16-7.8   180  GAGCATTGGTATTAGCTTACAC  TGGTACCAGCAGAAACCAGATCAGCTCTCCAAAGCTCCTCATCAAG TATGCTTCCCAGT  259
A26        81  ..........G...........  ..............................................  .............  160
JK1

-------->  <----------------------------------FWR3-----------------------------
H16-7.8   260  CCTTCTCA   GGGGTCCCCTCGAGGTTCAGTGGCAGTGGATCTGGGACAGATTTCACCCTCACCATCAATAGCCTGGAAGCT  339
A26       161  ........   ....................................................................  240
JK1

-->
H16-7.8   340  GAAGATGCTGCAACGTATTACTGT  CATCAGAGTAGGAGTTTCCCGTGGACGTTCGGCCAAGGGACCAAGGTGGAAATCAA  419
A26       241  ........................  .........................T.................................  281
JK1         1                            .......................................................   36

H16-7.8   420  ACGAACTGTGGCTGCACCATCTGTCTTCATCTTCCCGCCATCTGATGAGCAGTTGAAATCTGGAACTGCCTCTGTTGTGT  499
A26
JK1        37  ...............................................................................   38

H16-7.8   500  GCCTGCTGAATAACTTCTATCCCAGAGAGGCCAAAGTACAGTGGAAGGTGGA  551
A26
JK1
```

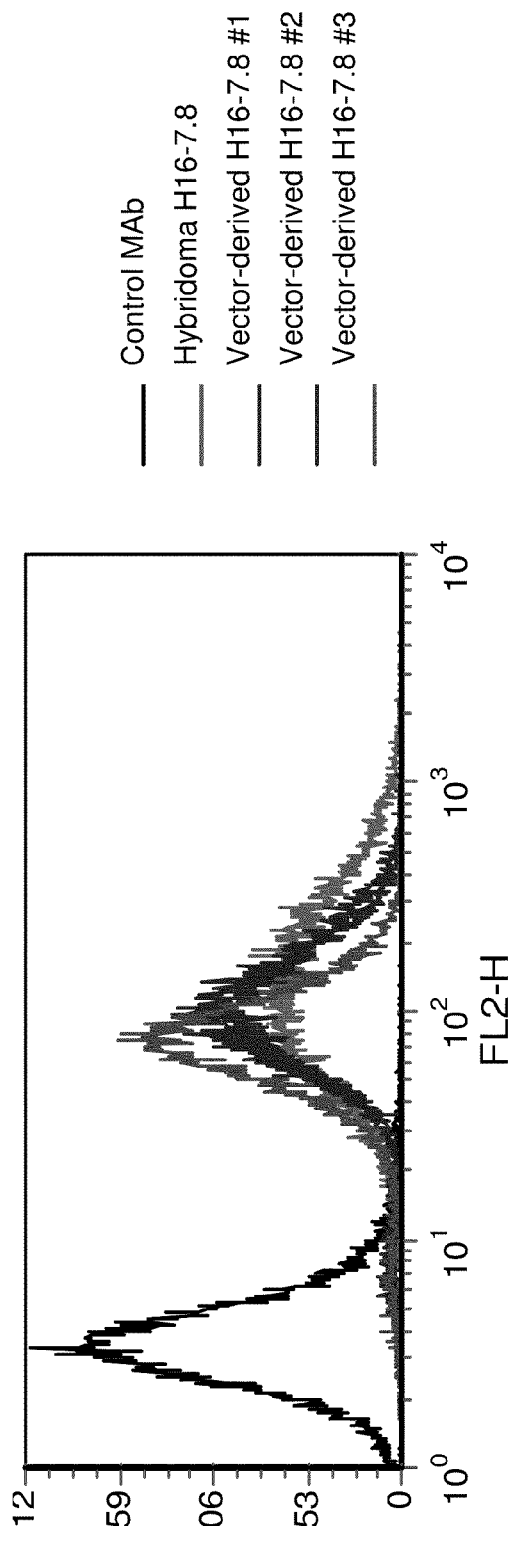
Figure 5: H16-7.8 Recombinant Expression in CHO Cells

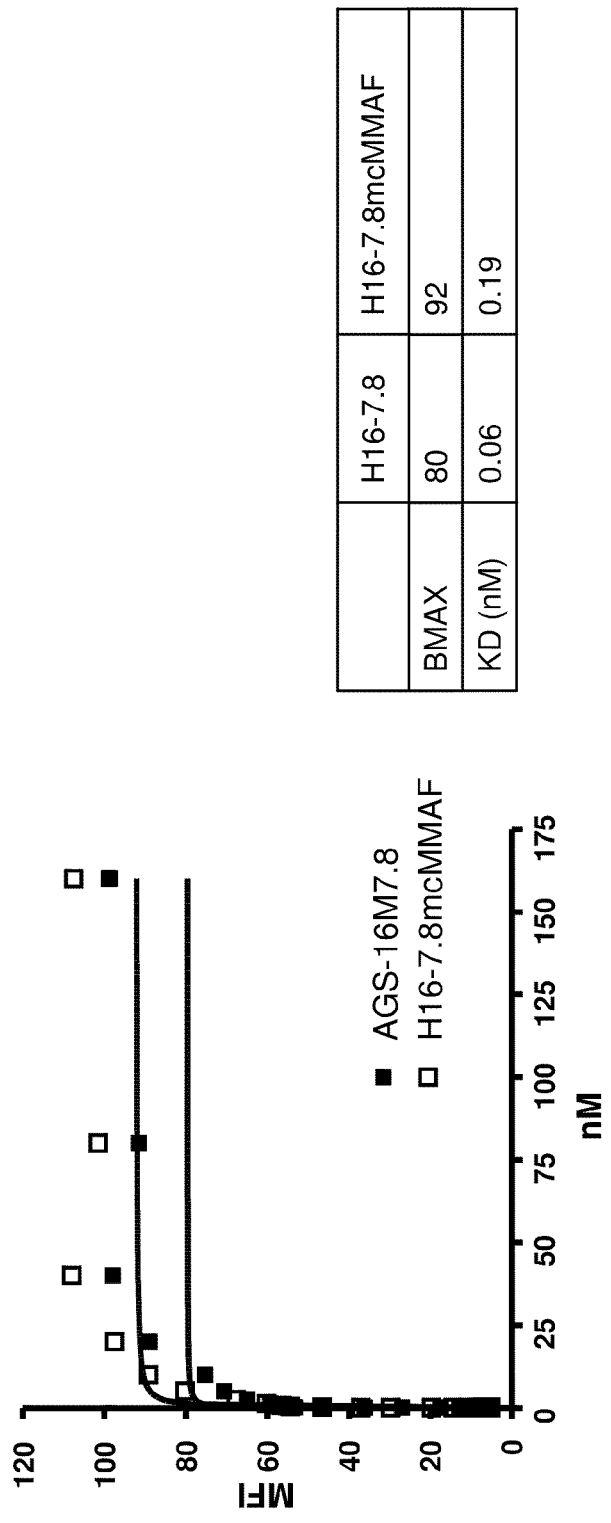
Figure 6: Cell Binding and Affinity of H16-7.8 and H16-7.8mcMMAF

Figure 7: Binding of H16-7.8 and H16-7.8mcMMAF to Renal Cancer Cells
UG-K3:
H16-7.8
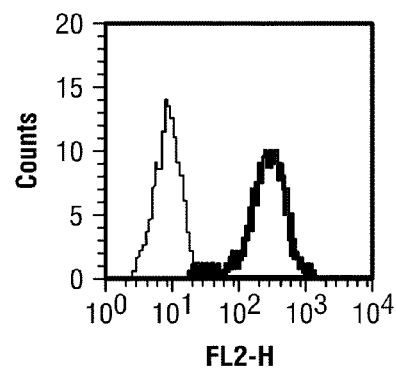
H16-7.8mcMMAF
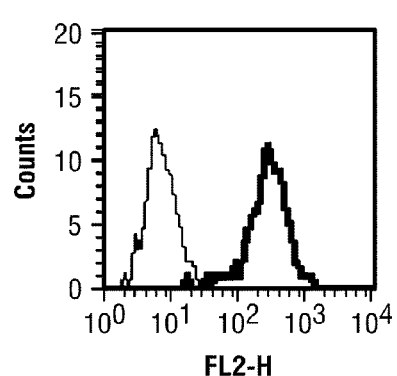
RXF-393:
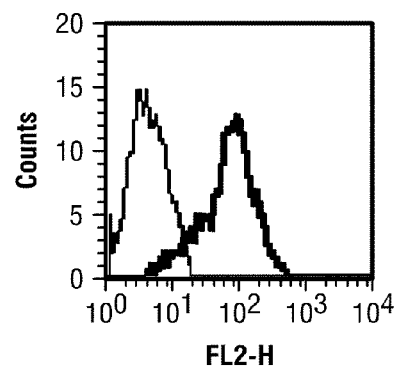
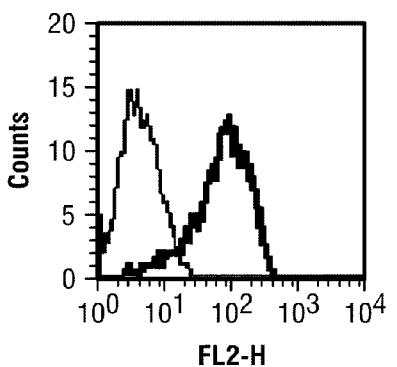

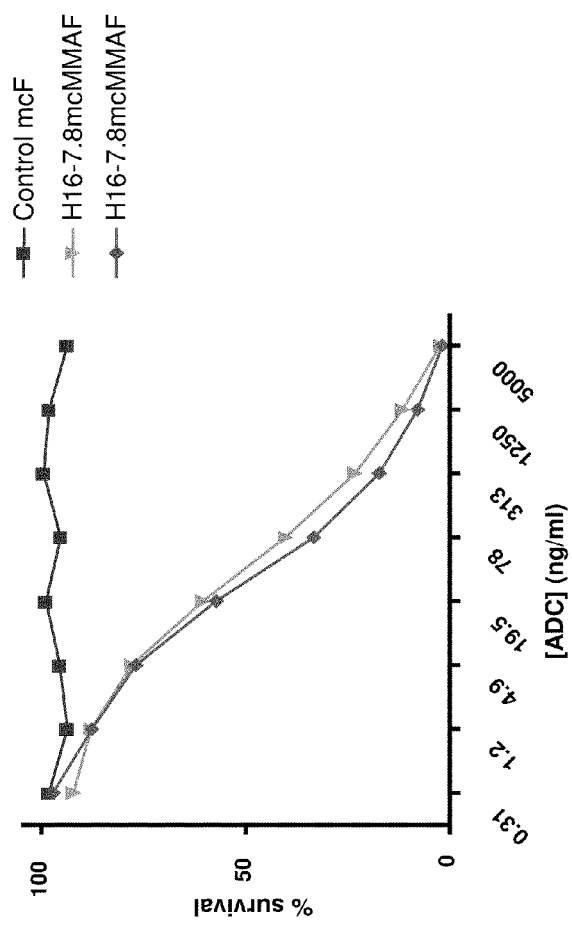
Figure 8: Cytotoxicity of H16-7.8mcMMAF for KU812 Cells

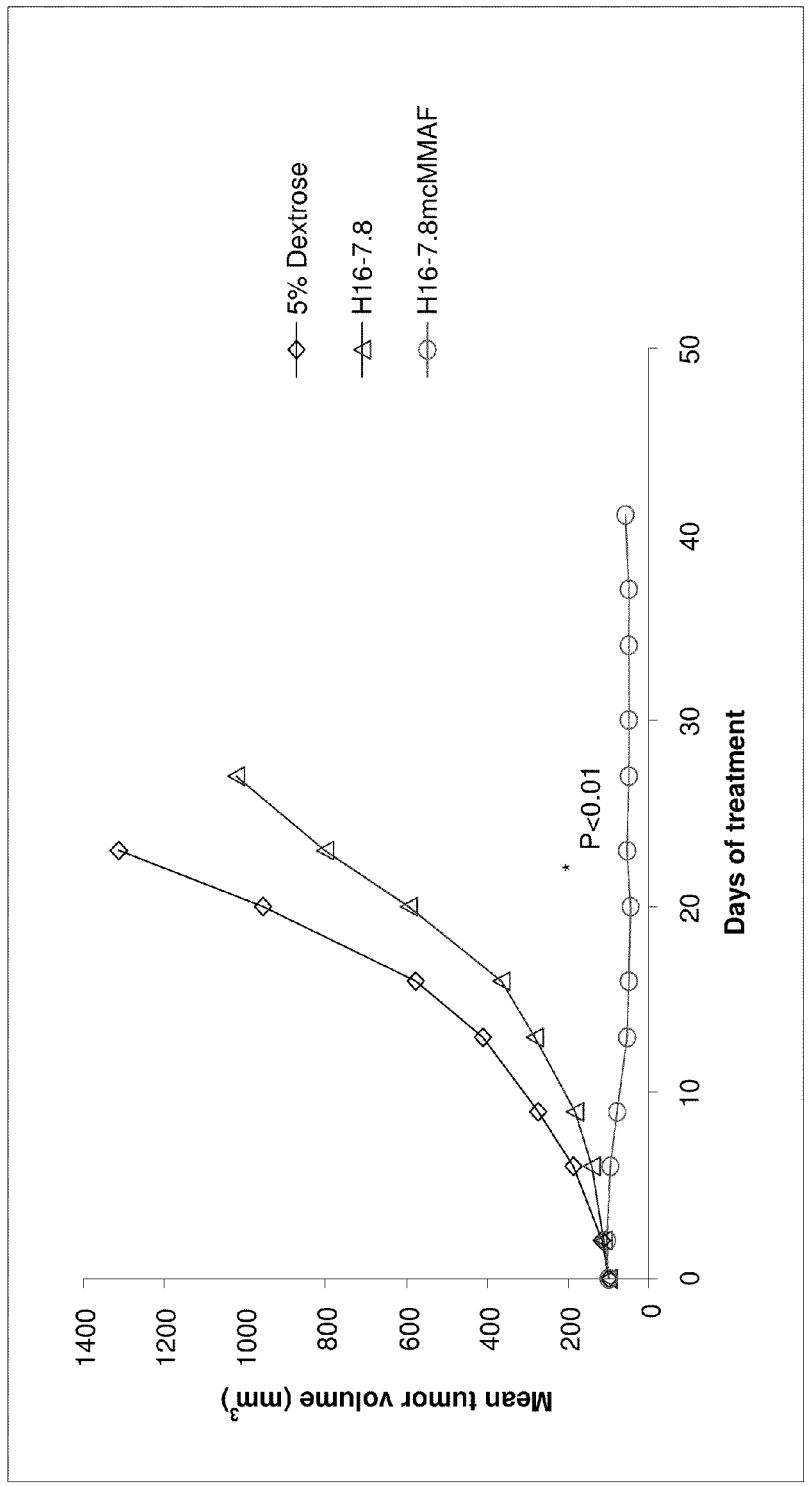
Figure 9: Efficacy of H16-7.8mcMMAF in subcutaneously established human renal cancer xenograft UG-K3 in SCID mice

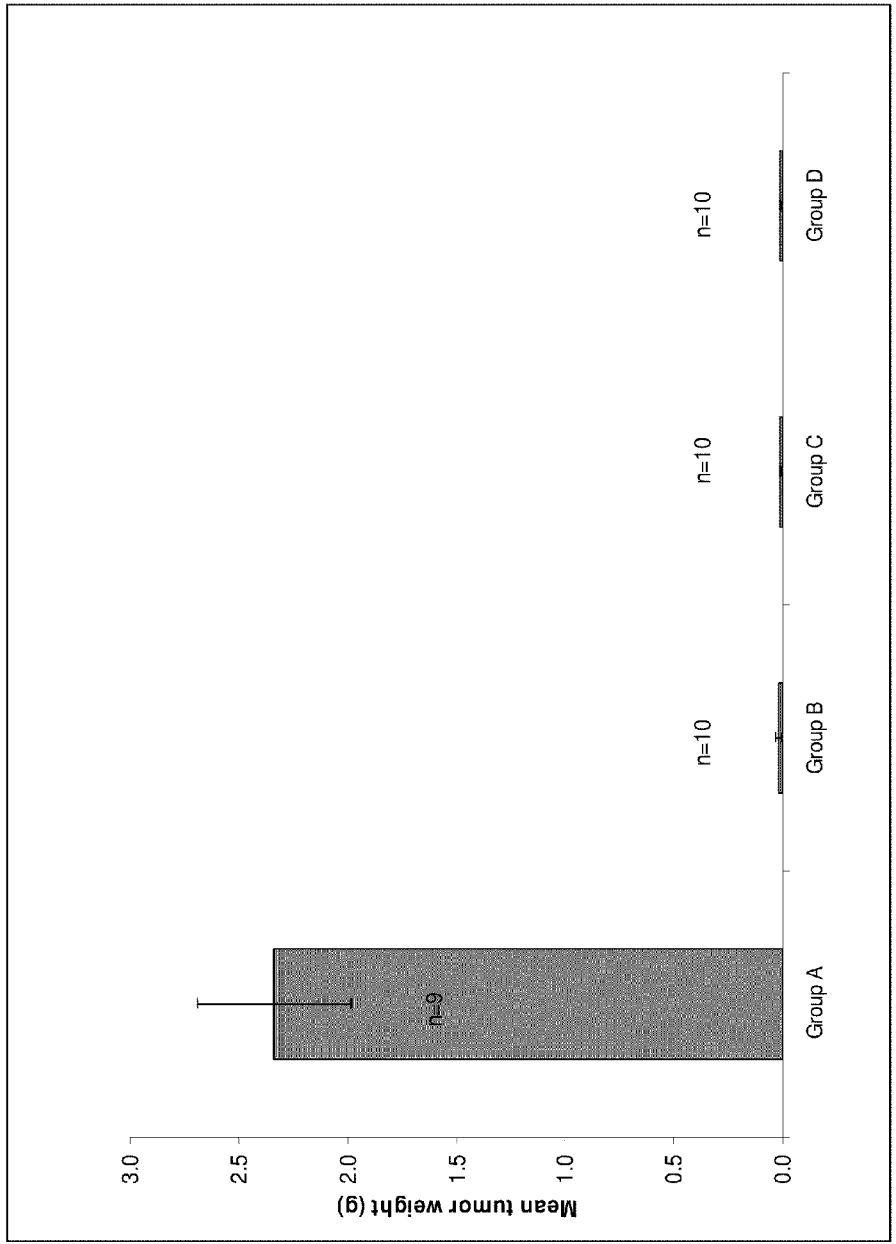
Figure 10: Potent Inhibition of Established Orthotopic Renal Cancer Xenografts with Different Doses and Schedules of H16-7.8mcMMAF

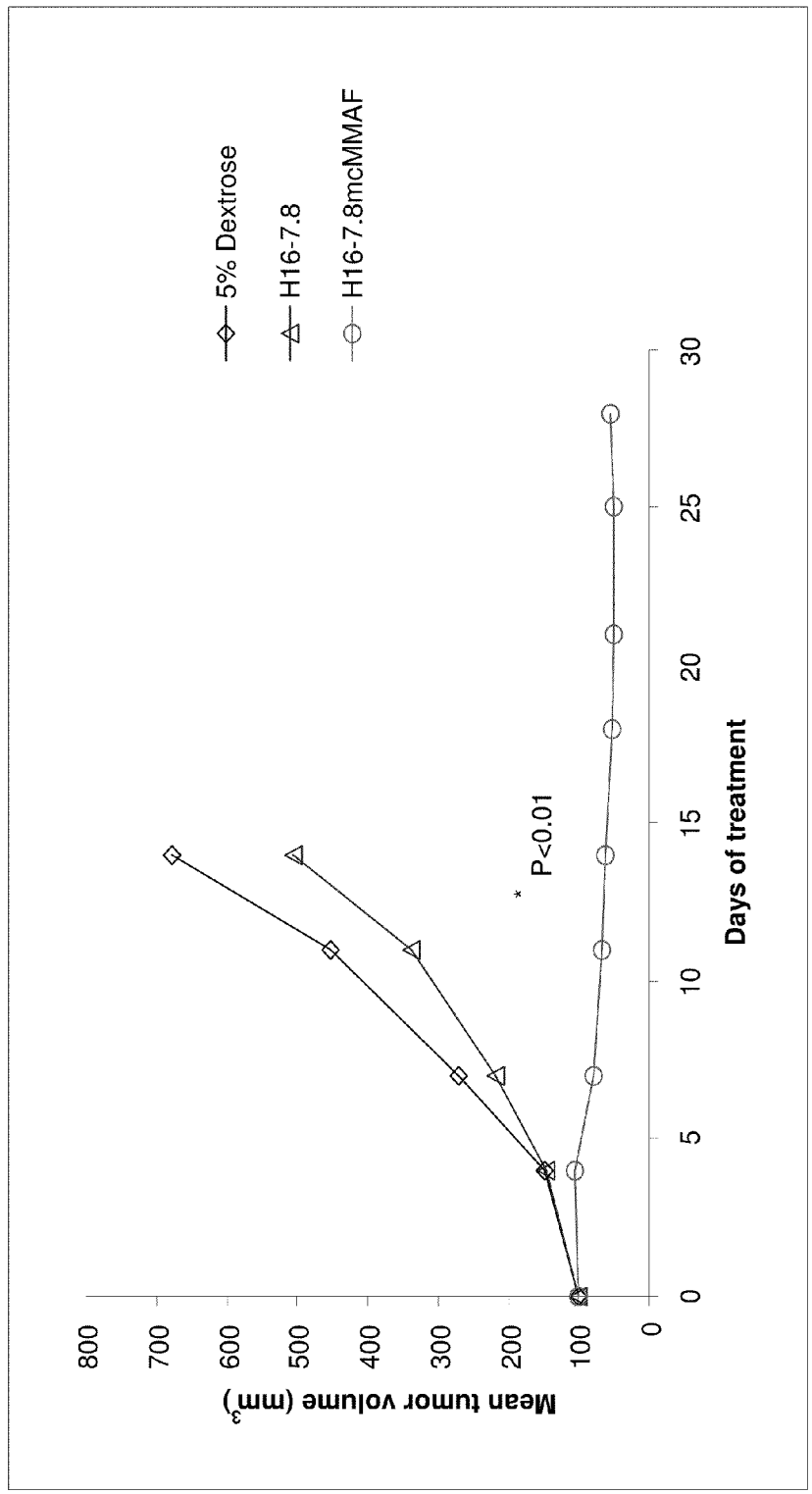

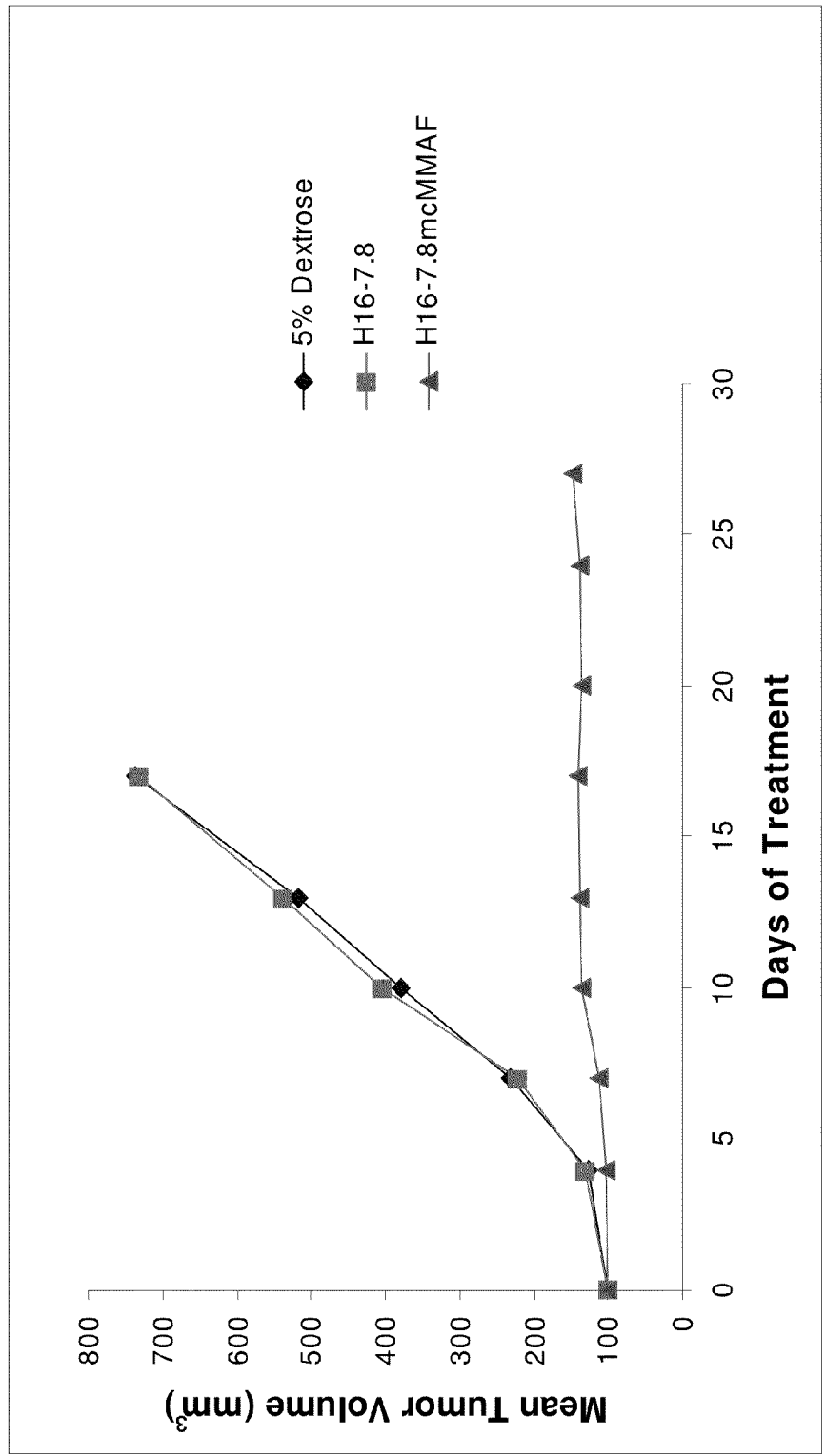
Figure 12: Efficacy Study of H16-7.8mcMMAF compared to H16-7.8 in subcutaneously established human renal cancer SKRC-01 in SCID mice

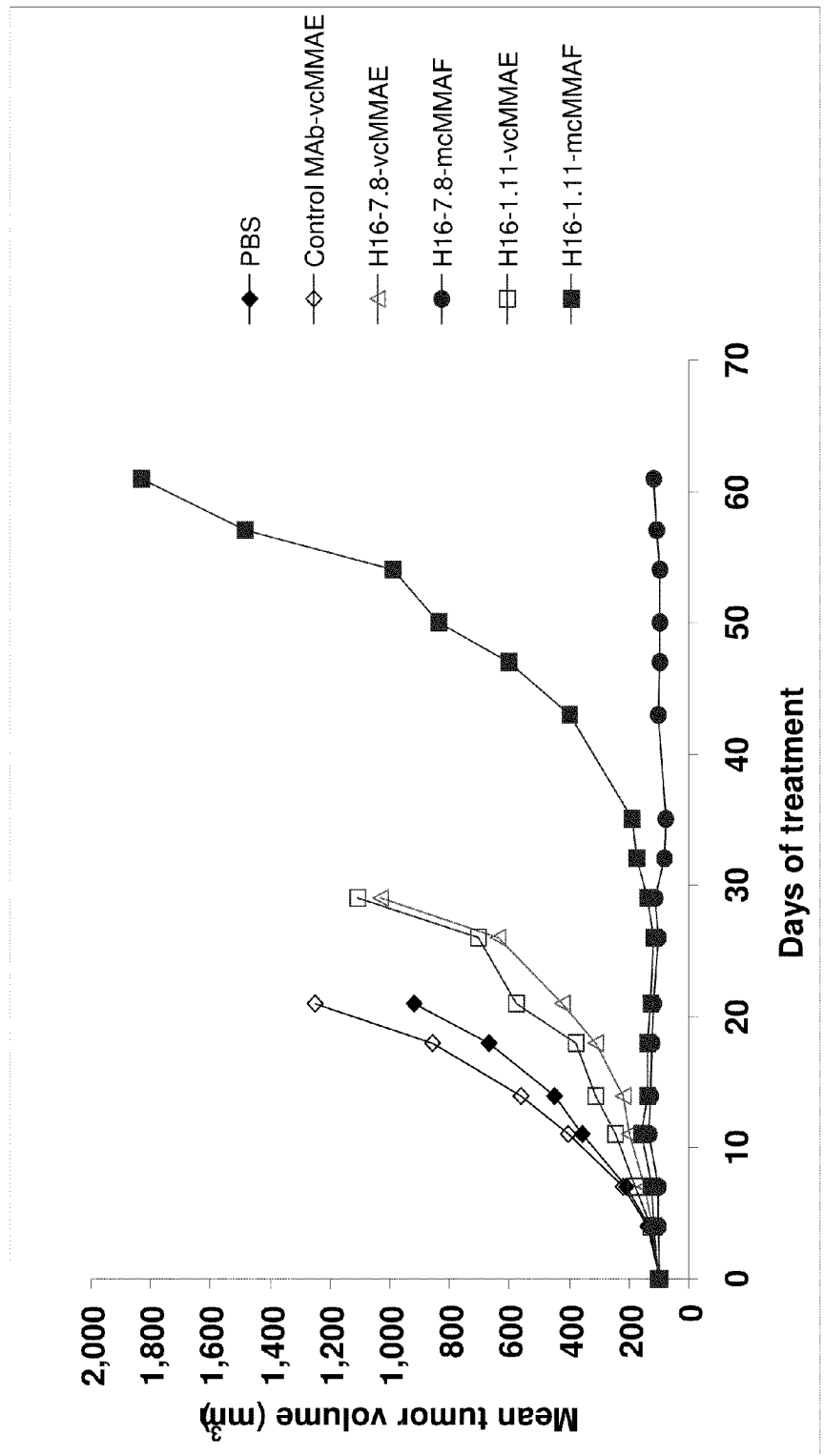
Figure 13: Efficacy of H16-7.8mcMMAF compared to other 161P2F10B Antibody Drug Conjugates (ADCs) in subcutaneous established UG-K3 xenografts in SCID mice

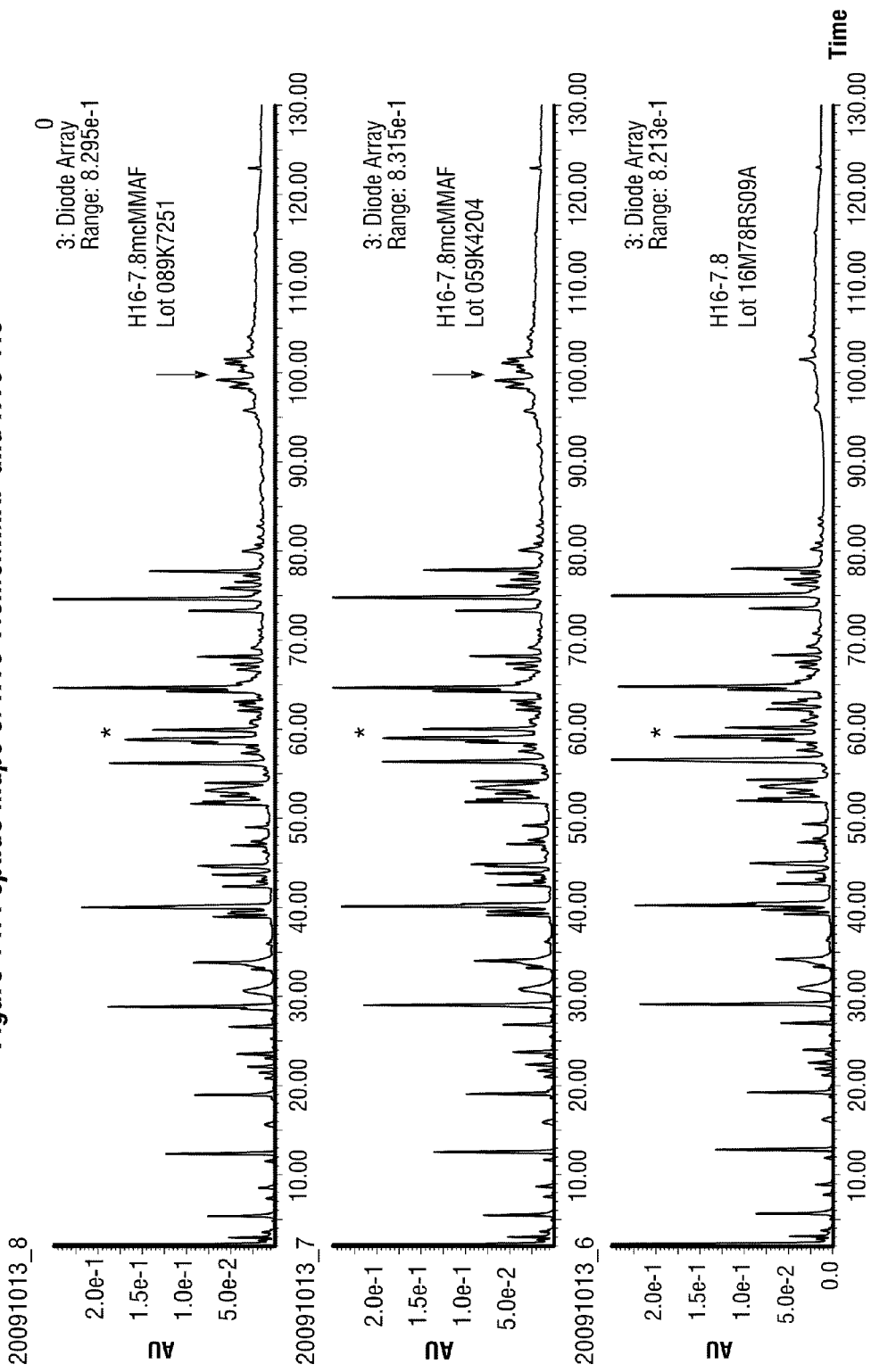
Figure 14. Peptide maps of H16-7.8mcMMAF and H16-7.8

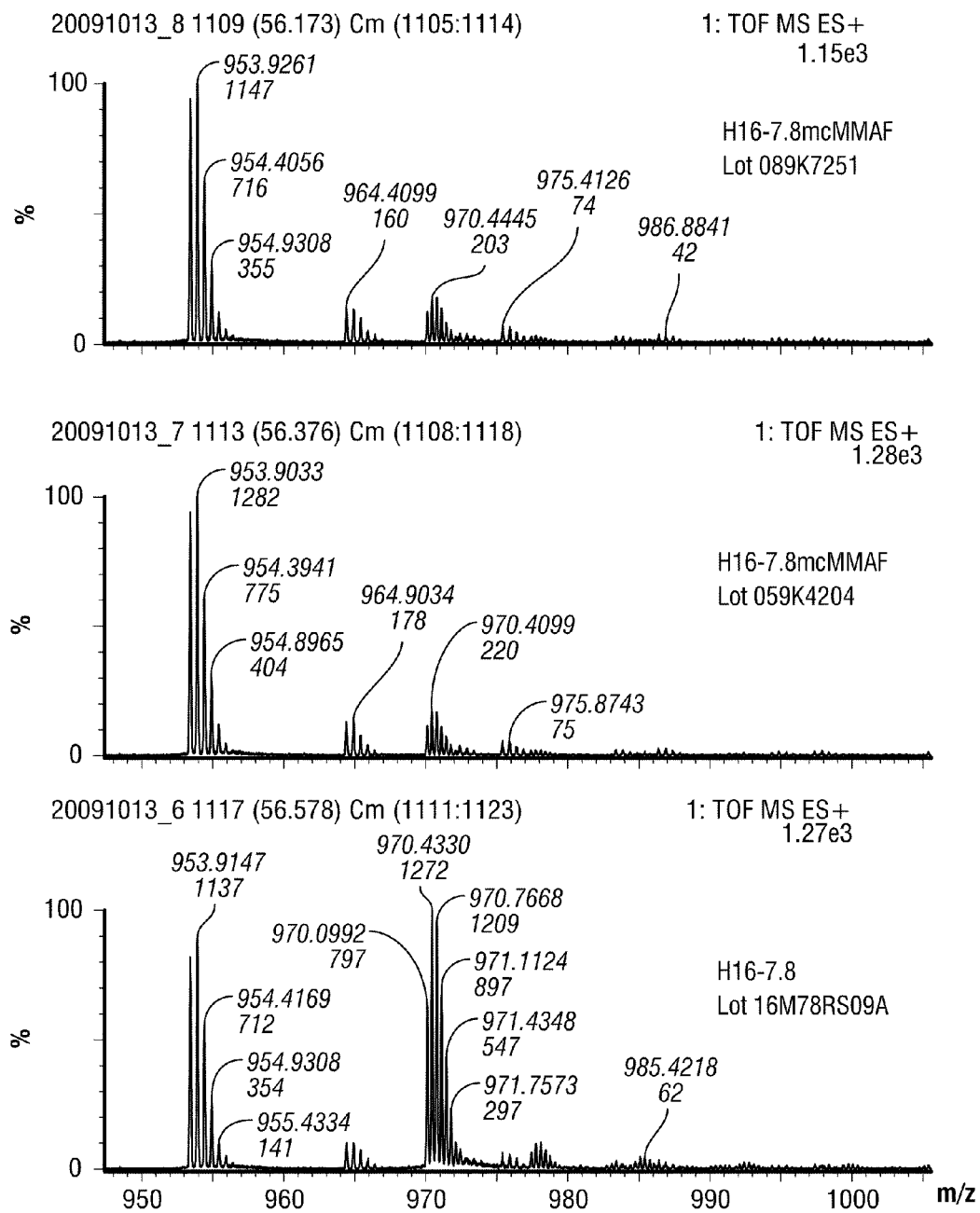
Figure 15. Mass Spectra of the (*) Peak of H16-7.8mcMMAF and H16-7.8

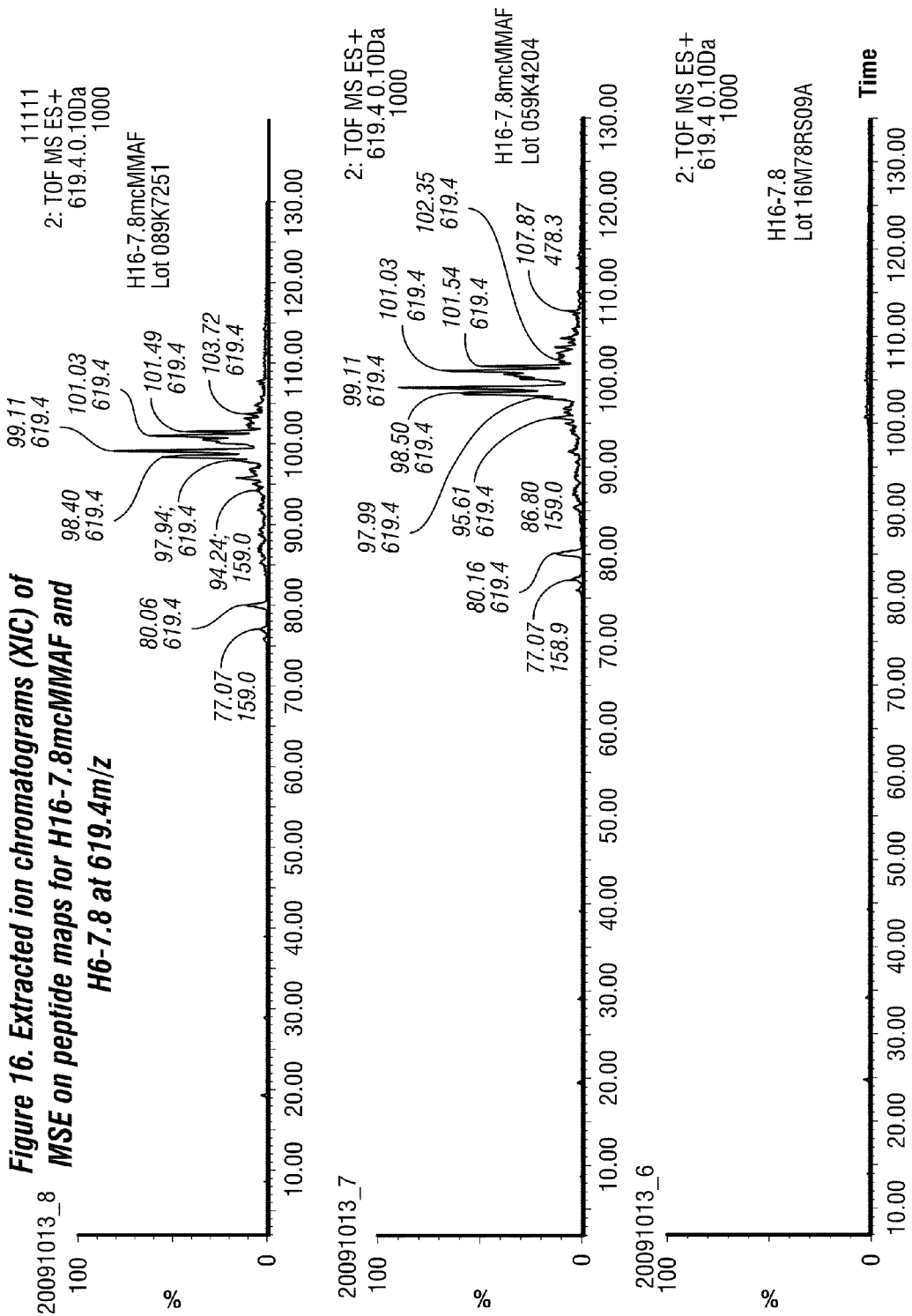
Figure 16. Extracted ion chromatograms (XIC) of MSE on peptide maps for H16-7.8mcMMAF and H6-7.8 at 619.4m/z

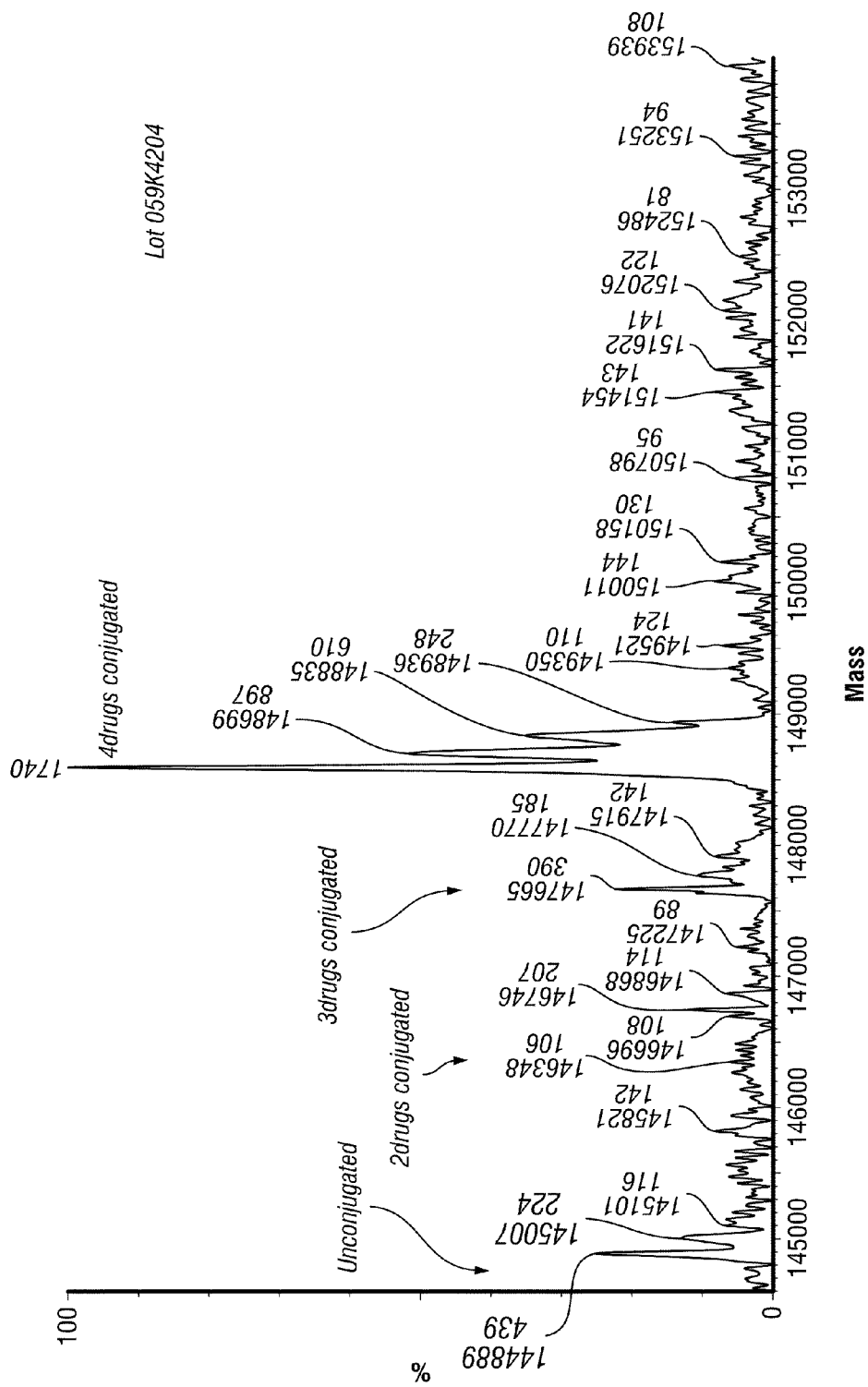
Figure 17(a). Example Spectra showing mass profiles of deglycosylated H16-7.8mcMMAF

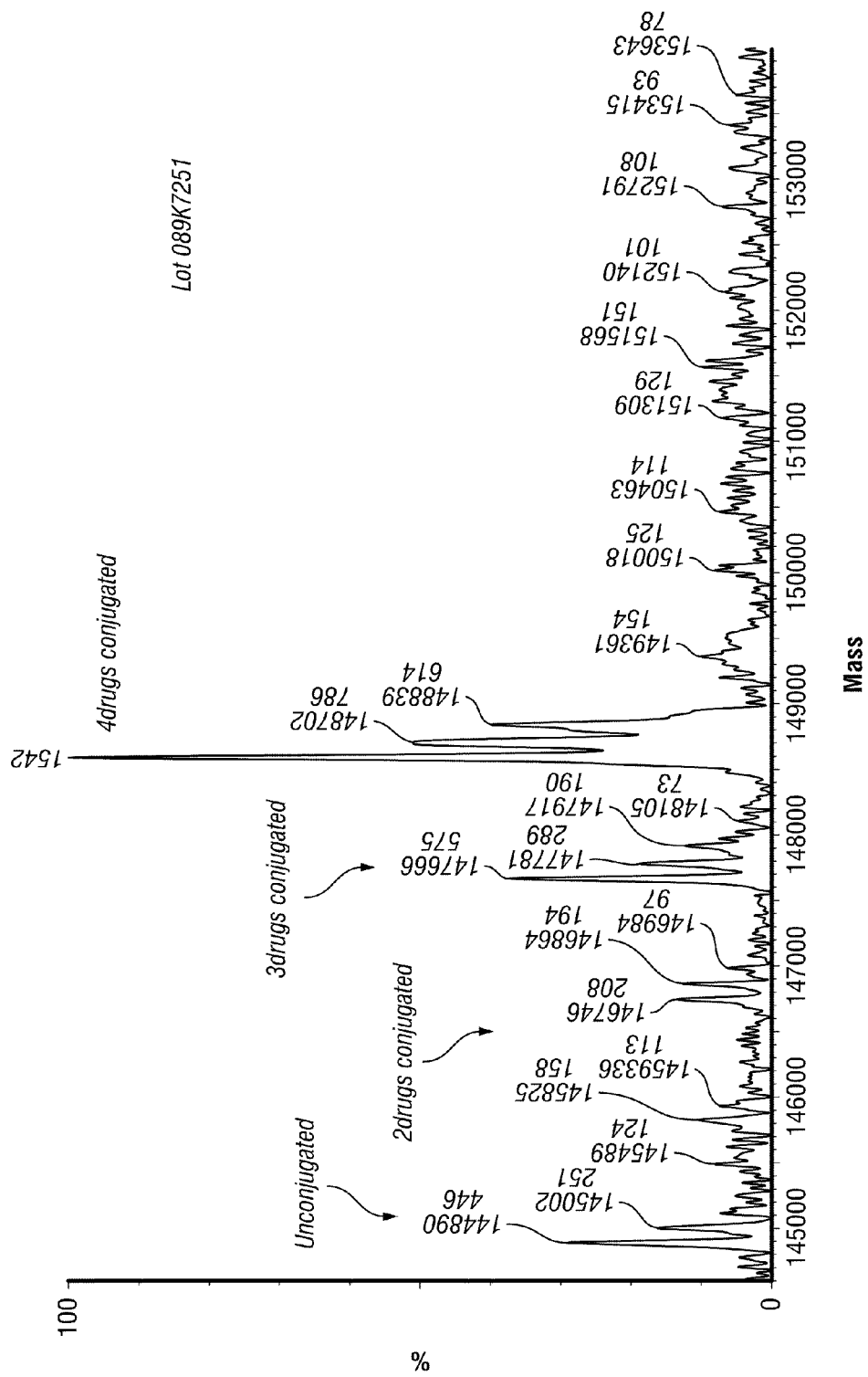
Figure 17(b). Example Spectra showing mass profiles of deglycosylated H16-7.8mcMMAF

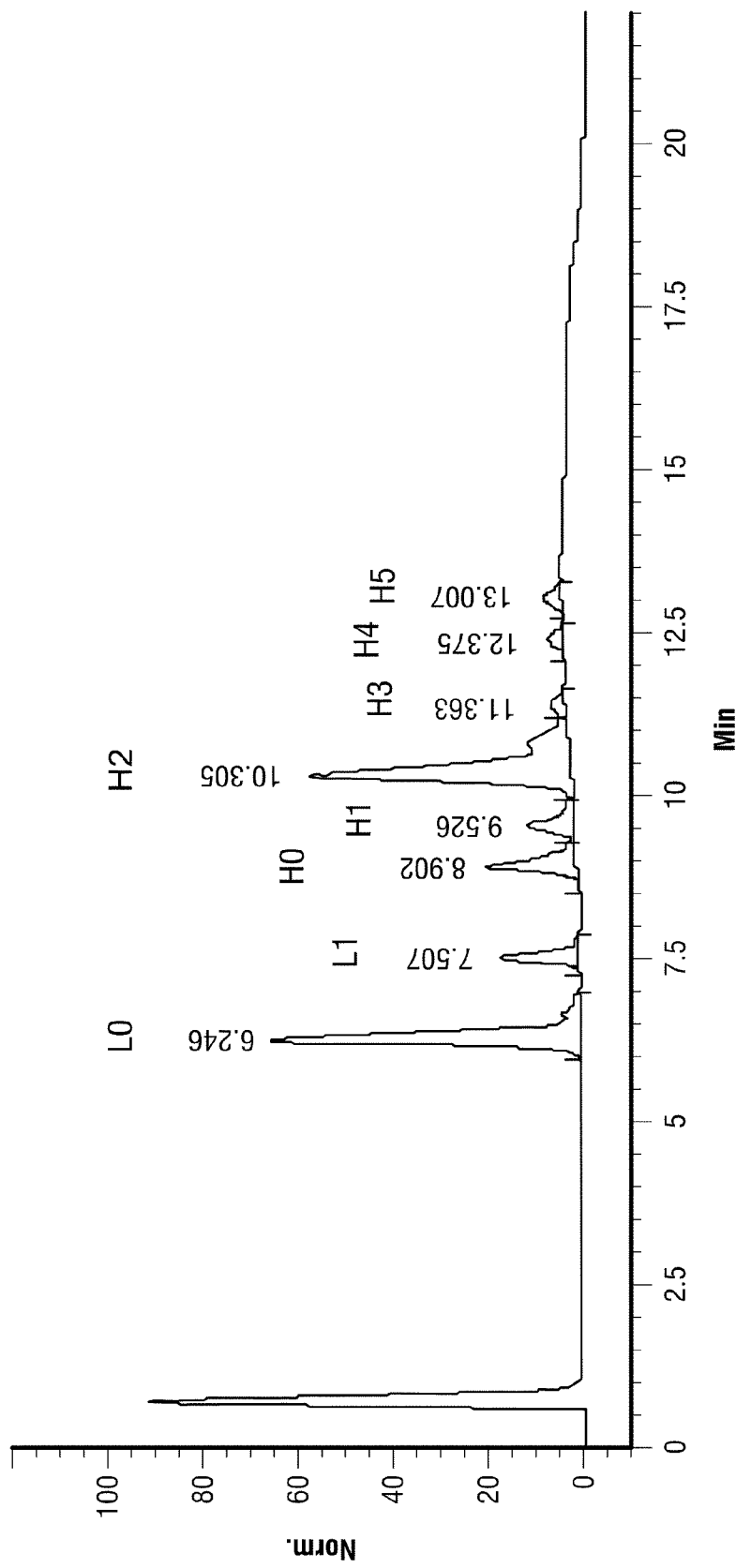
Figure 18. Drug Antibody Ratio (DAR) Profile of H16-7.8mcMMAF

ANTIBODY DRUG CONJUGATES (ADC) THAT BIND TO 161P2F10B PROTEINS

CROSS-REFERENCE TO RELATED APPLICATION

This application claims the benefit of priority to U.S. Provisional Application No. 61/302,489, filed on Feb. 8, 2010. The contents of that application are hereby incorporated by reference in their entirety.

STATEMENT OF RIGHTS TO INVENTIONS MADE UNDER FEDERALLY SPONSORED RESEARCH

Not applicable.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 511582006231Seqlist.txt | Jan. 27, 2011 | 43,609 bytes |

FIELD OF THE INVENTION

The invention described herein relates to antibody drug conjugates (ADCs) thereof that bind proteins, termed 161P2F10B. The invention further relates to prognostic, prophylactic and therapeutic methods and compositions useful in the treatment of cancers.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

While previously identified markers such as PSA, PSM, PCTA and 161P2F10B have facilitated efforts to diagnose and treat prostate cancer, there is need for the identification of additional markers and therapeutic targets for prostate and related cancers in order to further improve diagnosis and therapy.

Renal Cell Cancer (RCC) presently ranks 10th as the leading cause of cancer death in the United States. An estimated 51,190 people will be diagnosed annually with renal cell carcinoma in the US and approximately 12,890 died from the disease in 2007 (American Cancer Society). Historically, treatment has focused primarily on nephrectomy, followed by nonspecific immunotherapy, and sometimes radiation therapy (Hauke, 2006). Nonspecific immunotherapy includes treatment with the cytokines interleukin-2 or interferon-$\alpha$ as either single agents or in combination. After surgical excision, 20-30% of patients will develop metastatic disease within 1-3 years, often in the lung (Motzer, et al., 2006). Median survival for patients with metastatic disease is approximately 13 months (Cohen and McGovern, 2005).

Since 2005, six (6) agents have been approved by FDA for the treatment advanced renal cell cancer. These advances include several agents that target the specific pathways implicated in renal cell cancer. These agents include sorafenib (Nexavar®, FDA approved in December 2005), sunitinib (Sutent®, FDA approved in January 2006), temsirolimus (Torisel®, FDA approved in May 2007), everolimus (Affinitor®, FDA approved in March, 2009), bevacizumab (Avastin® in combination with interferon alpha, FDA approved in August 2009) and pazopanib (Votrient® FDA approved in October 2009). However, despite advances in the treatment, metastatic Renal cell cancer remains incurable and only temsirolimus was approved based on an advantage in overall survival.

Additionally, hepatocellular carcinoma (i.e., cancer of the liver) accounts for 80-90% of all liver cancers. This type of liver cancer occurs more often in men than in women. It is usually seen in people ages 50-60. Generally, treatment of liver cancer is aggressive surgery or a liver transplant which may successfully treat small or slow growing tumors if they are diagnosed early. However, few patients are diagnosed early. Chemotherapy and radiation treatments are not usually effective. However, these therapies are used to shrink tumors so surgery has a greater chance of success. Sorafenib tosylate (Nexavar®) is now available for patients with liver cancer. The prognosis for patients with liver cancer is usually poor, since only 10-20% of hepatocellular carcinomas can be removed using surgery. Accordingly, there is a need to develop an agent used to treat liver cancer.

The therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari, et al., Annual Rev. Immunol., 6:555-580 (1988)).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann, et al., *Proc. Nat'l. Acad. Sci. USA* 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse® mice and is commercially available from Amgen Fremont, Inc. (Fremont Calif.).

SUMMARY OF THE INVENTION

The invention provides antibody drug conjugates (ADCs) that bind to 161P2F10B proteins. In some embodiments, the invention comprises fully human antibodies conjugated with a therapeutic agent.

The invention further provides various immunogenic or therapeutic compositions, such as antibody drug conjugates, and strategies for treating cancers such as cancers of tissues listed in Table I.

The present invention relates to:

[1] An antibody drug conjugate comprising an antibody or antigen binding fragment thereof that binds specifically to a 161P2F10B protein comprising the amino acid sequence of SEQ ID NO:2, and wherein the antibody comprises the amino acid sequence of the $V_H$ region of SEQ ID NO:7, from 20 to 142 and the $V_L$ region of SEQ ID NO:8, from 20 to 127 and wherein said antibody is conjugated to monomethyl auristatin F (MMAF).

[2] The antibody drug conjugate of [1], wherein the antigen binding fragment is an Fab, F(ab')$_2$ or Fv fragment.

[3] The antibody drug conjugate of [1], wherein the antibody is a fully human antibody.

[4] The antibody drug conjugate of [1], which is recombinantly produced.

[5] A pharmaceutical composition that comprises the antibody drug conjugate of [1] in a human unit dose form.

[6] The pharmaceutical composition of [5], wherein the composition is for cancer treatment.

[7] The pharmaceutical composition of [6], wherein the cancer is renal cancer or liver cancer.

[8] A method of inhibiting growth of cancer cells in a subject, comprising: administering to said subject an antibody drug conjugate of [1].

[9] A method of delivering a cytotoxic agent or a diagnostic agent to a cell, comprising:
providing MMAF(s) conjugated to an antibody or antigen binding fragment thereof that binds specifically to a 161P2F10B protein comprising the amino acid sequence of SEQ ID NO:2, and wherein the antibody comprises the amino acid sequence of the $V_H$ region of SEQ ID NO:7, from 20 to 142 and the $V_L$ region of SEQ ID NO:8, from 20 to 127, to form an antibody drug conjugate; and,
exposing the cell to the antibody drug or fragment drug conjugate.

[10] A method for treating tumor in a mammal comprising treating the mammal with an effective amount of an antibody drug conjugate of [1].

[11] A method for reducing tumor growth in a mammal comprising treating the mammal with an effective amount of a combination of an antibody drug conjugate of [1] and radiation.

[12] A method for reducing tumor growth in a mammal comprising treating the mammal with an effective amount of a combination of an antibody drug conjugate of [1] and a chemotherapeutic agent.

[13] A method for reducing tumor growth in a mammal comprising treating the mammal with an effective amount of a combination of an antibody drug conjugate of [1] and a drug or biologically active therapy.

[14] A method for treating cancer in a mammal, comprising treating the mammal with an effective amount of a combination of an antibody drug conjugate of [1] and a chemotherapeutic agent.

[15] An antibody drug conjugate (ADC), wherein the ADC having the formula L-(LU-D)p, wherein: (a) L is the antibody comprising an antibody or antigen binding fragment thereof that binds specifically to a 161P2F10B protein comprising the amino acid sequence of SEQ ID NO:2, and wherein the antibody comprises the amino acid sequence of the $V_H$ region of SEQ ID NO:7, from 20 to 142 and the $V_L$ region of SEQ ID NO:8, from 20 to 127; (b) LU is a linker; (c) D is a drug moiety wherein drug is monomethyl auristatin F (MMAF); (d) p is 1, 2, 3, 4, 5, 6, 7, 8, 9, 10, 11 or 12.

[16] An antibody drug conjugate (ADC), wherein the ADC having the following formula, wherein Ab-S is the antibody comprising an antibody or antigen binding fragment thereof that binds specifically to a 161P2F10B protein comprising the amino acid sequence of SEQ ID NO:2, and wherein the antibody comprises the amino acid sequence of the $V_H$ region of SEQ ID NO:7, from 20 to 142 and the $V_L$ region of SEQ ID NO:8, from 20 to 127; p is 1, 2, 3, 4, 5, 6, 7, 8, 9, 10, 11 or 12.

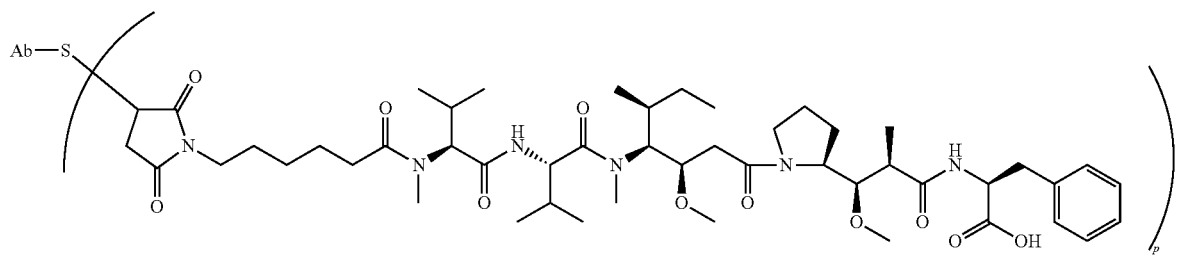

[17] An antibody drug conjugate comprising an antibody that binds specifically to a 161P2F10B protein comprising the amino acid sequence of SEQ ID NO:2, and wherein the antibody comprises the amino acid sequence of the heavy chain of SEQ ID NO:7, from 20 to 468 and the light chain of SEQ ID NO:8, from 20 to 233 and wherein said antibody is conjugated to monomethyl auristatin F (MMAF).

[18] An antibody drug conjugate (ADC), wherein the ADC having the formula L-(LU-D)p, wherein: (a) L is the antibody comprising an antibody that binds specifically to a 161P2F10B protein comprising the amino acid sequence of SEQ ID NO:2, and wherein the antibody comprises the amino acid sequence of the heavy chain of SEQ ID NO:7, from 20 to 468 and the light chain of SEQ ID NO:8, from 20 to 233; (b) LU is a linker; (c) D is a drug moiety wherein drug is monomethyl auristatin F (MMAF); (d) p is 1, 2, 3, 4, 5, 6, 7, 8, 9, 10, 11 or 12.

[19] An antibody drug conjugate (ADC), wherein the ADC having the following formula, wherein Ab-S is the antibody comprising an antibody that binds specifically to a 161P2F10B protein comprising the amino acid sequence of SEQ ID NO:2, and wherein the antibody comprises the amino acid sequence of the heavy chain of SEQ ID NO:7, from 20 to 468 and the light chain of SEQ ID NO:8, from 20 to 233; p is 1, 2, 3, 4, 5, 6, 7, 8, 9, 10, 11 or 12.

FIG. 4B. Alignment of H16-7.8 light chain to human germline A26/JK1.

FIG. 5. H16-7.8 Recombinant Expression in CHO Cells. H16-7.8 heavy and light chain sequences were cloned into expression vectors. Vectors were transfected into CHO cells. 3T3-control and 3T3-161P2F10B cells were stained with H16-7.8 from either hybridoma or from CHO cells. Binding was detected by flow cytometry. Results show H16-7.8 recombinantly expressed in CHO cells is secreted and binds specifically to cell-surface 161P2F10B.

FIG. 6. Cell Binding and Affinity of H16-7.8 and H16-7.8mcMMAF. H16-7.8 and H16-7.8mcMMAF were tested for the binding affinity to 161P2F10B endogenously expressed on Ku812 cells. Briefly, eleven (11) dilutions of H16-7.8 or H16-7.8mcMMAF were incubated with Ku812 cells (50,000 cells per well) overnight at 4° C. at a final concentration of 160 nM to 0.0001 nM. At the end of the incubation, cells were washed and incubated with anti-hIgG-PE detection antibody for 45 min at 4° C. After washing the unbound detection antibodies, the cells were analyzed by FACS. Mean Florescence Intensity (MFI) values are obtained (See, Table IV). MFI values were entered into Graphpad Prisim software and analyzed using the one site binding (hyperbola) equation of Y=Bmax*X/(Kd+X) to generate H16-7.8 or H16-7.8mcMMAF saturation curves shown in FIG. 6.

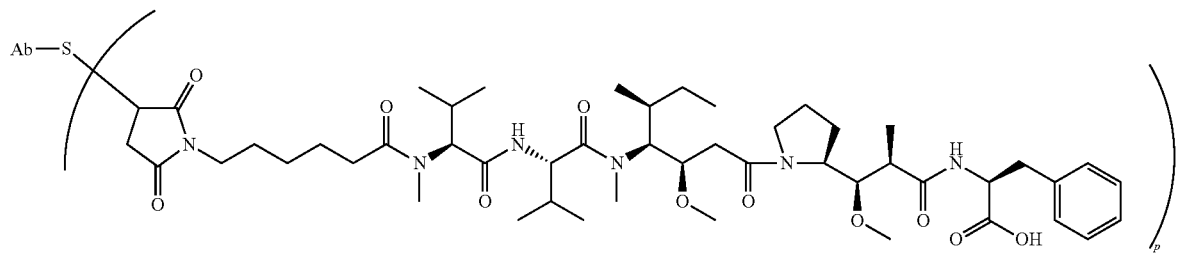

BRIEF DESCRIPTION OF THE FIGURES

FIG. 1. The cDNA and amino acid sequence of 161P2F10B is shown in FIG. 1. The open reading frame extends from nucleic acid 44-2671 including the stop codon.

FIG. 2. Nucleic Acid and Amino Acid sequences of 161P2F10B antibodies.

FIG. 2A. The cDNA and amino acid sequence of H16-7.8 heavy chain. Underlined is the leader sequence and double-underlined is the heavy chain variable region. Dashed underline shows the human IgG2 constant region.

FIG. 2B. The cDNA and amino acid sequence of H16-7.8 light chain. Underlined is the leader sequence and double-underlined is the light chain variable region. Dashed underline shows the human Ig kappa constant region.

FIG. 3. Amino Acid sequences of 161P2F10B antibodies.

FIG. 3A. The amino acid sequence of H16-7.8 heavy chain. Underlined is the leader sequence and double-underlined is the heavy chain variable region. Dashed underline shows the human IgG2 constant region.

FIG. 3B. The amino acid sequence of H16-7.8 light chain. Underlined is the leader sequence and double-underlined is the light chain variable region. Dashed underline shows the human Ig kappa constant region.

FIG. 4. Alignment of H16-7.8 antibodies to human germline.

FIG. 4A. Alignment of H16-7.8 heavy chain to human germline VH4-31/D5-12/JH6.

Bmax is the MFI value at maximal binding of H16-7.8 or H16-7.8mcMMAF to 161P2F10B; Kd is H16-7.8 or H16-7.8mcMMAF binding affinity which is the concentration of H16-7.8 or H16-7.8mcMMAF required to reach half-maximal binding. The calculated affinity (Kd) of H16-7.8 and H16-7.8mcMMAF is 0.06 nM and 0.19 nM, respectively on 161P2F10B endogenously expressed on the surface of Ku812 cells.

FIG. 7. Binding of H16-7.8 and H16-7.8mcMMAF to Renal Cancer Cells. Human UGK-3 cells (patient derived clear cell renal cancer) and RXF-393 cells (clear cell renal cancer) were stained with 10 μg/ml of native H16-7.8, H16-7.8mcMMAF, or an isotype control human IgG2 and evaluated by FACS. The results in FIG. 7 (left panels) demonstrate strong staining of the two different renal tumor cells with H16-7.8 (gray lines), but not with the control MAb (filled histograms). The panels on the right demonstrate a similar strong staining of the same renal tumor cells with H16-7.8mcMMAF (gray lines). (FIG. 7; right panels). These results show that both H16-7.8 and H16-7.8mcMMAF bind native 161P2F10B antigen expressed on the surface of human cancer cells. Conjugation of native H16-7.8 to generate the H16-7.8mcMMAF did not alter its cell surface binding to native 161P2F10B antigen expressed on human cancer cells.

FIG. 8. Cell Cytotoxicity by H16-7.8mcMMAF. 2000 viable KU812 cells were plated in triplicate on Day 0 and allowed to recover overnight. The next day, serial 1:4 dilutions of different lots of H16-7.8mcMMAF or a control MAb conjugated with mcMMAF were added to yield the final concentrations. The cells were allowed to incubate for six (6) days at which time 20 μl of Alamar blue was added to each well. The plates were incubated for an additional four (4) hours and the fluorescence intensity read on a fluorescent plate reader using an excitation wavelength of 540 nM and an emission wavelength of 620 nM. The results show that both lots of H16-7.8mcMMAF potently inhibited the proliferation of KU812 cells. The IC 50 was determined to be 0.2 nM and 0.1 nM for Lots (1) and Lot (2) respectively. A fully human Control MAb that does not bind KU812 cells was conjugated with mcMMAF to yield a DAR of 3.9 (+/−0.2). The Control ADC (Control mcF) did not inhibit KU812 cell proliferation further demonstrating the specificity of cytotoxicity. Thus, these results indicate that H16-7.8mcMMAF can selectively deliver a cytotoxic drug to 161P2F10B expressing cells, leading to their killing.

FIG. 9. Efficacy of H16-7.8mcMMAF in subcutaneously established human renal cancer xenograft UG-K3 in SCID mice. In this experiment, patient-derived human renal cancer xenograft UG-K3 was maintained by serial passages in SCID mice. Stock tumors were harvested sterilely and minced to small pieces. The tumor pieces were enzymatically digested to single cell suspensions using Liberase Blendzyme (Roche Applied Science, Indianapolis, Ind.). $1.5 \times 10^6$ cells were injected into the flanks of individual SCID mice and tumors were allowed to grow untreated until they reached an approximate volume of 100 $mm^3$. Animals were randomly assigned to the following cohorts: an H16-7.8mcMMAF treated group, an H16-7.8 control and a 5% Dextrose control. H16-7.8mcMMAF and H16-7.8 were dosed at 10 mg/kg once on day 0 by intravenous bolus injection. The amount of H16-7.8mcMMAF and H16-7.8 administered was based on the individual body weight of each animal obtained immediately prior to dosing. The 5% Dextrose control was dosed at 150 μL per animal. Tumor growth was monitored using caliper measurements every 3 to 4 days until the end of the study. Tumor volume is calculated as $Width^2 \times Length/2$, where width is the smallest dimension and length is the largest. Animals in control groups were humanely euthanized when tumors reached approximately 1000 $mm^3$. Animals in H16-7.8mcMMAF treated group were monitored for an additional two weeks before sacrifice. Statistical analysis was performed at the last time point when data for both control groups were available, using Kruskal-Wallis test with $\alpha=0.05$.

The results demonstrated that treatment of UG-K3 renal clear cell xenograft tumors with H16-7.8mcMMAF at all doses and schedules examined resulted in significant inhibition of tumor growth in SCID mice.

FIG. 10. Growth Inhibition of Established Orthotopic UG-K3 Xenografts by H16-7.8mcMMAF. The ability of H16-7.8mcMMAF to inhibit the growth of established renal tumors grown orthotopically was evaluated using patient-derived, UG-K3 tumor xenografts. Briefly, stocks of UG-K3 tumors were digested enzymatically and 1.5 million viable cells were surgically implanted into the kidneys of male SCID mice on Day 0. The tumors were allowed to grow for 7 days at which time animals were randomized to 4 different treatment groups (n=10 per group). Animals randomized to Group A received Control ADC at 5 mpk, Group B received H16-7.8mcMMAF at 3 mg/kg and Group C received H16-7.8mcMMAF at 5 mg/kg administered every 4 days for a total of 4 doses. Group D received H16-7.8mcMMAF at 10 mg/kg one time. At the end of the study (Day 41) the animals were sacrificed and the right and left kidneys weighed on an electronic balance. The tumor weights plotted on the graph were determined by subtracting the weight of the tumor-free contralateral kidney from the weight of the tumor-bearing right kidney.

The results demonstrated that treatment of UG-K3 renal clear cell xenograft tumors with H16-7.8mcMMAF at all doses and schedules examined resulted in dramatic inhibition of tumor growth. Tumor weights in all H16-7.8mcMMAF treatment groups (B, C, and D) were less than 1% of the tumor weights in the Control treated group. These differences were highly statistically significant (p<0.0001, ANOVA).

FIG. 11. Efficacy of H16-7.8mcMMAF in subcutaneously established human renal cancer xenograft RXF-393 in SCID mice. In this experiment, human renal cancer cells RXF-393 ($0.5 \times 10^6$ cells per mouse) were injected into the flanks of individual mice and tumors were allowed to grow untreated until they reached an approximate volume of 100 $mm^3$. Animals were then randomly assigned to the following cohorts: an H16-7.8mcMMAF treated group, an H16-7.8 treated group and a 5% Dextrose control. H16-7.8mcMMAF and H16-7.8 were dosed at 10 mg/kg once a week for a total of two doses by intravenous bolus injection. The amount of H16-7.8mcMMAF and H16-7.8 administered was based on the individual body weight of each animal obtained immediately prior to dosing. The 5% Dextrose control was dosed at 150 μL per animal. Tumor growth was monitored using caliper measurements every 3 to 4 days until the end of the study. Tumor volume is calculated as $Width^2 \times Length/2$, where width is the smallest dimension and length is the largest. Animals in control groups were humanely euthanized when tumors reached approximately 1000 $mm^3$ Animals in H16-7.8mcMMAF treated group were monitored for an additional two weeks before sacrifice.

The results demonstrated that treatment of RFX-393 human renal cancer xenograft tumors with H16-7.8mcMMAF at all doses and schedules examined resulted in significant inhibition of tumor growth in SCID mice. Statistical analysis was performed at the last time point when data in both control groups were available, using Kruskal-Wallis test with $\alpha=0.05$.

FIG. 12. Efficacy Study of H16-7.8 compared to H16-7.8mcMMAF in subcutaneously established human renal cancer SKRC-01 in SCID Mice. Human renal cancer cells SKRC-01 ($0.8 \times 10^6$ cells per mouse) were injected into the flanks of individual mice. Tumors were allowed to grow untreated until they reached an approximate volume of 100 $mm^3$. On day 0 when tumors reach 100 $mm^3$, animals were randomly assigned to the following cohorts: an H16-7.8mcMMAF treated group, an H16-7.8 treated group and a 5% Dextrose control. H16-7.8mcMMAF and H16-7.8 were dosed at 4 mg/kg every four days for a total of four doses by intravenous bolus injection. The amount of H16-7.8mcMMAF and H16-7.8 administered was based on the individual body weight of each animal obtained immediately prior to dosing. The 5% Dextrose control was dosed at 150 μL per animal. Tumor growth was monitored using caliper measurements every 3 to 4 days. Tumor volume was calculated as $Width^2 \times Length/2$, where width is the smallest dimension and length is the largest.

The results show that the ADC H16-7.8mcMMAF significantly inhibited the growth of SKRC-01 tumor formation while the naked MAb H16-7.8 had no effect. Thus, the ADC H16-7.8mcMMAF had a significantly more prominent effect that the naked antibody H16-7.8.

FIG. 13. Efficacy Study of H16-7.8mcMMAF compared to other 161P2F10B Antibody Drug Conjugates (ADCs) in subcutaneous established UG-K3 in SCID mice. In another experiment, human renal cancer cells UG-K3 ($1.5 \times 10^6$ cells per mouse) were injected into the flanks of individual mice. Tumors were allowed to grow untreated until they reached an approximate volume of 100 mm$^3$. On day 0 when tumors reach 100 mm$^3$, animals were randomly assigned to the following cohorts: an H16-7.8mcMMAF, an H16-7.8vcMMAE, and H16-1.11mcMMAF, and H16-1.11vcMMAE, a PBS control, and a control MAb-vcMMAE treated group. All antibody drug conjugates (ADCs) were dosed at 10 mg/kg once on day 0. The amount of each ADC administered was based on the individual body weight of each animal obtained immediately prior to dosing. The PBS control was dosed at 150 µ/L per animal. Tumor growth was monitored using caliper measurements every 3 to 4 days. Tumor volume was calculated as Width$^2$×Length/2, where width is the smallest dimension and length is the largest.

The results show that the ADCs H16-7.8vcMMAE and H16-1.11vcMMAE did not inhibit tumor formation growth. Additionally, both the H16-7.8mcMMAF and H16-1.11mcMMAF significantly inhibited the growth of UG-K3 tumor formation during the first thirty (30) days. After day thirty (30) the H16-7.8mcMMAF had a significantly more prominent effect when compared to H16-1.11mcMMAF.

FIG. 14. Peptide maps of H16-7.8mcMMAF and H16-7.8. The obtained H16-7.8mcMMAF and H16-7.8 were treated with dithiothreitol (DTT) to reduce disulfide bonds, followed by alkylation of the resulting free cysteines. Guanidine was used in this step to ensure complete denaturation of the protein. After dialysis to remove the guanidine, the samples were digested with a specific endoproteinase, Lys-C. Lys-C cleaves peptide bonds on the C-terminal side of lysine residues. The resulting peptides were analyzed by reversed phase chromatography coupled to mass spectrometry. The reversed phase retention times and the observed mass to charge ratios of the peaks were compared between H16-7.8mcMMAF and H16-7.8. LC-MS (liquid chromatography-mass spectrometry) analysis was carried out using a WATERS Acquity UPLC coupled to a WATERS Q-TOFp mass spectrometer. The digested sample was applied to YMC C18 column and eluted with an acetonitrile gradient containing trifluoroacetic acid. The results show, peak intensities indicated by asterisk were reduced in the conjugated antibody compared to the native antibody. The peaks marked with an arrow represent new peaks that appeared on the conjugated antibody peptide map. Specifically, the peaks marked with either an asterisk or with an arrow are believed to be a peptide destined for conjugation and the resulting conjugated peptide, respectively.

FIG. 15. Mass spectra of the (*) peak. The results show a portion of the mass spectra of the peak marked with an asterisk in FIG. 14. The mass value of the signal that changed during conjugation is indicated by the "plus" sign. This peptide with an approximate m/z of 970.4 (+3 charge state) was identified as C225-K250 that originated from the hinge region of the heavy chain and contains the expected conjugation sites.

FIG. 16. Extracted ion chromatograms (XIC) of MSE on peptide maps for H16-7.8mcMMAF and H16-7.8 at 619.4 m/z. In order to identify the newly appeared peaks which are believed to be conjugated peptide in FIG. 14 above, LC-MS analysis was conducted using the elevated-energy (MSE) data acquisition technique. This Figure shows the extracted ion chromatograms (XIC) for peptide maps of H16-7.8mcMMAF and H16-7.8 using the m/z of 619.4. This ion corresponds to a fragment ion of the drug moiety. Peaks observed in XIC at 619.4 are almost identical to the peaks marked with an arrow in FIG. 14. Furthermore, no such peaks were detected in the chromatogram of the native antibody. These observations suggest that the detected peaks in the XIC at m/z of 619.4 were apparently drug conjugated peptides and are identified by its intact mass values. The result was summarized in Table V. These results suggest that in case of the conjugate, predominant peptides are those conjugated to 2 drugs on the hinge region of heavy chain. These data are consistent with the data obtained by the other orthogonal such as a DAR analysis.

FIG. 17. Example Spectra showing mass profiles of deglycosylated H16-7.8mcMMAF ADC. The full mass of the deglycosylated H16-7.8mcMMAF was determined by electrospray ionization time-of-flight (ESI-TOF) mass spectrometry. Test samples were diluted by 250 mM sodium phosphate buffer, pH 7.5 and then incubated overnight at 37° C. with glycopeptidase F. The samples were injected onto a PLRPTM column (Varian Technology), equilibrated at 90° C., and eluted with an acetonitrile/water gradient. The sample peaks were analyzed by an Acquity UPLC system coupled to a WATERS Synapt mass spectrometer (Waters) and masses were reconstructed from the raw data by a MaxEnt1 software. An example mass spectral profile for the deglycosylated H16-7.8mcMMAF is shown. The predominant drug conjugated antibody was a 4-drug loading species. This observation including an abundance of the unconjugated antibody in H16-7.8mcMMAF was consistent with the results obtained by the other orthogonal methods, such as DAR by RP-HPLC, peptide mapping, and HIC assay.

FIG. 18. Drug Antibody Ratio (DAR) profile of H16-7.8mcMMAF. DAR analysis was conducted for quantitative HPLC determination of the relative amount of drug loading in each Light chain and Heavy chain. DAR analyses were carried out using a PLRP-S analytical column, 2.1 mm×50 mm, with mobile phase A consisting of 2.0% formic acid and mobile phase B consisting of 2.0% formic acid plus 90% acetonitrile. A representative DAR profile for H16-7.8mcMMAF is shown. DAR value is 4.0. The sample was subjected to LC-MS analysis using same HPLC conditions of this method to identify the observed peak. Results are summarized in Table VI. The peak identification of the DAR results obtained during the qualification of this method has been confirmed orthogonally by LC-MS.

DETAILED DESCRIPTION OF THE INVENTION

Outline of Sections
I.) Definitions
II.) 161P2F10B Antibodies
III.) Antibody Drug Conjugates Generally
    III(A). Auristatins and Dolostatins
IV.) Antibody Drug Conjugates which Bind 161P2F10B
V.) Linker Units
VI.) The Stretcher Unit
VII.) The Amino Acid Unit
VIII.) The Spacer Unit
IX.) The Drug Unit
X.) Drug Loading
XI.) Methods of Determining Cytotoxic effect of ADCs
XII.) Treatment of Cancer(s)
XIII.) 161P2F10B as a Target for Antibody-based Therapy
XIV.) 161P2F10B ADC Cocktails
XV.) Combination Therapy
XVI.) KITS/Articles of Manufacture
I.) Definitions:
Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook, et al., *Molecular Cloning: A Laboratory Manual* 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

The abbreviation "AFP" refers to dimethylvaline-valine-dolaisoleuine-dolaproine-phenylalanine-p-phenylenediamine (see Formula XVI infra).

The abbreviation "MMAE" refers to monomethyl auristatin E (see Formula XI infra).

The abbreviation "AEB" refers to an ester produced by reacting auristatin E with paraacetyl benzoic acid (see Formula XX infra).

The abbreviation "AEVB" refers to an ester produced by reacting auristatin E with benzoylvaleric acid (see Formula XXI infra).

The abbreviation "MMAF" refers to dovaline-valine-dolaisoleuine-dolaproine-phenylalanine (see Formula XVIV infra).

Unless otherwise noted, the term "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, iso-propyl, n-butyl, iso-butyl, sec-butyl, Cert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl, and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more groups including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the terms "alkenyl" and "alkynyl" refer to straight and branched carbon chains having from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetylenyl, propynyl, -1-butynyl, -2-butynyl, -1-pentynyl, -2-pentynyl, and -3-methyl-1 butynyl.

Alkenyl and alkynyl groups, whether alone or as part of another group, can be optionally substituted with one or more groups, preferably 1 to 3 groups (and any additional substituents selected from halogen), including but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the term "alkylene" refers to a saturated branched or straight chain hydrocarbon radical having from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like. Alkylene groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH₂, —NH(R'), —N(R')₂ and —CN, where each R' is independently selected from —H, —C₁-C₈ alkyl, —C₂-C₈ alkenyl, —C₂-C₈ alkynyl, or -aryl and wherein said —O—(C₁-C₈ alkyl), —O—(C₂-C₈ alkenyl), —O—(C₂-C₈ alkynyl), -aryl, —C₁-C₈ alkyl, —C₂-C₈ alkenyl, and —C₂-C₈ alkynyl groups can be further optionally substituted with one or more substituents including, but not limited to, —C₁-C₈ alkyl, —C₂-C₈ alkenyl, —C₂-C₈ alkynyl, -halogen, —O—(C₁-C₈ alkyl), —O—(C₂-C₈ alkenyl), —O—(C₂-C₈ alkynyl), -aryl, —C(O)R", —OC(O)R", —C(O)OR", —C(O)NH₂, —C(O)NHR", —C(O)N(R")₂, —NHC(O)R", —SR", —SO₃R", —S(O)₂R", —S(O)R", —OH, —N₃, —NH₂, —NH(R"), —N(R")₂ and —CN, where each R" is independently selected from —H, —C₁-C₈ alkyl, —C₂-C₈ alkenyl, —C₂-C₈ alkynyl, or -aryl.

Unless otherwise noted, the term "alkenylene" refers to an optionally substituted alkylene group containing at least one carbon-carbon double bond. Exemplary alkenylene groups include, for example, ethenylene (—CH═CH—) and propenylene (—CH═CHCH₂—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH₂C≡C—), and 4-pentynyl (—CH₂CH₂CH₂C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, -halogen, —C₁-C₈ alkyl, —C₂-C₈ alkenyl, —C₂-C₈ alkynyl, —O—(C₁-C₈ alkyl), —O—(C₂-C₈ alkenyl), —O—(C₂-C₈ alkynyl), -aryl, —C(O)R', —OC(O)R', —C(O)OR', —C(O)NH₂, —C(O)NHR', —C(O)N(R')₂, —NHC(O)R', —SR', —SO₃R', —S(O)₂R', —S(O)R', —OH, —NO₂, —N₃, —NH₂, —NH(R'), —N(R')₂ and —CN, where each R' is independently selected from —H, —C₁-C₈ alkyl, —C₂-C₈ alkenyl, —C₂-C₈ alkynyl, or -aryl and wherein said —C₁-C₈ alkyl, —C₂-C₈ alkenyl, —C₂-C₈ alkynyl, O—(C₁-C₈ alkyl), —O—(C₂-C₈ alkenyl), —O—(C₂-C₈ alkynyl), and -aryl groups can be further optionally substituted with one or more substituents including, but not limited to, —C₁-C₈ alkyl, —C₂-C₈ alkenyl, —C₂-C₈ alkynyl, -halogen, —O—(C₁-C₈ alkyl), —O—(C₂-C₈ alkenyl), —O—(C₂-C₈ alkynyl), -aryl, —C(O)R", —OC(O)R", —C(O)OR", —C(O)NH₂, —C(O)NHR", —C(O)N(R")₂, —NHC(O)R", —SR", —SO₃R", —S(O)₂R", —S(O)R", —OH, —N₃, —NH₂, —NH(R"), —N(R")₂ and —CN, where each R" is independently selected from —H, —C₁-C₈ alkyl, —C₂-C₈ alkenyl, —C₂-C₈ alkynyl, or -aryl.

Unless otherwise noted, the term "arylene" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group.

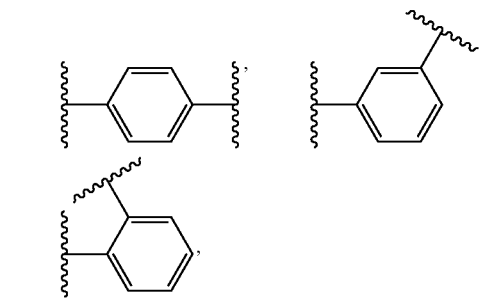

Typical "—(C₁-C₈ alkylene)aryl," "—(C₂-C₈ alkenylene)aryl", and —(C₂-C₈ alkynylene)aryl" groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and sub-combinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocyclic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "*Principles of Modern Heterocyclic Chemistry*" (W. A. Benjamin, New York, 1968), particularly Chapters 1, 3, 4, 6, 7, and 9; "*The Chemistry of Heterocyclic Compounds, A series of Monographs*" (John Wiley & Sons, New York, 1950 to present), in particular Volumes 13, 14, 16, 19, and 28; and *J. Am. Chem. Soc.* 82:5566 (1960).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

A heterocycle group, whether alone or as part of another group, can be optionally substituted with one or more groups, preferably 1 to 2 groups, including but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), —$C_1$-$C_8$ alkyl, —$C_2$-$C_8$ alkenyl, —$C_2$-$C_8$ alkynyl, and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo [4,5], [5,5], [5,6] or [6,6] system, or 9 or 10 ring atoms arranged as a bicyclo [5,6] or [6,6] system. The term "carbocycle" includes, for example, a monocyclic carbocycle ring fused to an aryl ring (e.g., a monocyclic carbocycle ring fused to a benzene ring). Carbocyles preferably have 3 to 8 carbon ring atoms.

Carbocycle groups, whether alone or as part of another group, can be optionally substituted with, for example, one or more groups, preferably 1 or 2 groups (and any additional substituents selected from halogen), including, but not limited to, -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Examples of monocyclic carbocylic substituents include -cyclopropyl, -cyclobutyl, -cyclopentyl, -1-cyclopent-1-enyl, -1-cyclopent-2-enyl, -1-cyclopent-3-enyl, cyclohexyl, -1-cyclohex-1-enyl, -1-cyclohex-2-enyl, -1-cyclohex-3-enyl, -cycloheptyl, -cyclooctyl, -1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

Unless otherwise indicated by context, a hyphen (-) designates the point of attachment to the pendant molecule. Accordingly, the term "—($C_1$-$C_8$ alkylene)aryl" or "—$C_1$-$C_8$ alkylene(aryl)" refers to a $C_1$-$C_8$ alkylene radical as defined herein wherein the alkylene radical is attached to the pendant molecule at any of the carbon atoms of the alkylene radical and one of the hydrogen atoms bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen. Groups that are substituted are so indicated.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Protective groups as used herein refer to groups which selectively block, either temporarily or permanently, one reactive site in a multifunctional compound. Suitable hydroxy-protecting groups for use in the present invention are pharmaceutically acceptable and may or may not need to be cleaved from the parent compound after administration to a subject in order for the compound to be active. Cleavage is through normal metabolic processes within the body. Hydroxy protecting groups are well known in the art, see, *Protective Groups in Organic Synthesis* by T. W. Greene and P. G. M. Wuts (John Wiley & sons, 3$^{rd}$ Edition) incorporated herein by reference in its entirety and for all purposes and include, for example, ether (e.g., alkyl ethers and silyl ethers including, for example, dialkylsilylether, trialkylsilylether, dialkylalkoxysilylether), ester, carbonate, carbamates, sulfonate, and phosphate protecting groups. Examples of hydroxy protecting groups include, but are not limited to, methyl ether; methoxymethyl ether, methylthiomethyl ether, (phenyldimethylsilyl)methoxymethyl ether, benzyloxymethyl ether, p-methoxybenzyloxymethyl ether, p-nitrobenzyloxymethyl ether, o-nitrobenzyloxymethyl ether, (4-methoxyphenoxy)methyl ether, guaiacolmethyl ether, t-butoxymethyl ether, 4-pentenyloxymethyl ether, siloxymethyl ether, 2-methoxyethoxymethyl ether, 2,2,2-trichloroethoxymethyl ether, bis(2-chloroethoxy)methyl ether, 2-(trimethylsilyl)ethoxymethyl ether, menthoxymethyl ether, tetrahydropyranyl ether, 1-methoxycylcohexyl ether, 4-methoxytetrahydrothiopyranyl ether, 4-methoxytetrahydrothiopyranyl ether S,S-Dioxide, 1-R2-choro-4-methyl)phenyl]-4-methoxypiperidin-4-yl ether, 1-(2-fluorophneyl)-4-methoxypiperidin-4-yl ether, 1,4-dioxan-2-yl ether, tetrahydrofuranyl ether, tetrahydrothiofuranyl ether; substituted ethyl ethers such as 1-ethoxyethyl ether, 1-(2-chloroethoxy)ethyl ether, 1-[2-(trimethylsilyl)ethoxy]ethyl ether, 1-methyl-1-methoxyethyl ether, 1-methyl-1-benzyloxyethyl ether, 1-methyl-1-benzyloxy-2-fluoroethyl ether, 1-methyl-1phenoxyethyl ether, 2-trimethylsilyl ether, t-butyl ether, allyl ether, propargyl ethers, p-chlorophenyl ether, p-methoxyphenyl ether, benzyl ether, p-methoxybenzyl ether 3,4-dimethoxybenzyl ether, trimethylsilyl ether, triethylsilyl ether, tripropylsilylether, dimethylisopropylsilyl ether, diethylisopropylsilyl ether, dimethylhexylsilyl ether, t-butyldimethylsilyl ether, diphenylmethylsilyl ether, benzoylformate ester, acetate ester, chloroacetate ester, dichloroacetate ester, trichloroacetate ester, trifluoroacetate ester, methoxyacetate ester, triphneylmethoxyacetate ester, phenylacetate ester, benzoate ester, alkyl methyl carbonate, alkyl 9-fluorenylmethyl carbonate, alkyl ethyl carbonate, alkyl 2,2,2,-trichloroethyl carbonate, 1,1-dimethyl-2,2,2-trichloroethyl carbonate, alkylsulfonate, methanesulfonate, benzylsulfonate, tosylate, methylene acetal, ethylidene acetal, and t-butylmethylidene ketal. Preferred protecting groups are represented by the formulas —R$^a$, —Si(R$^a$)(R$^a$)(R$^a$), —C(O)R$^a$, —C(O)OR$^a$, —C(O)NH(R$^a$), —S(O)$_2$R$^a$, —S(O)$_2$OH, P(O)(OH)$_2$, and —P(O)(OH)OR$^a$, wherein R$^a$ is C$_1$-C$_{20}$ alkyl, C$_2$-C$_{20}$ alkenyl, C$_2$-C$_{20}$ alkynyl, —C$_1$-C$_{20}$ alkylene(carbocycle), —C$_2$-C$_{20}$ alkenylene(carbocycle), —C$_2$-C$_{20}$ alkynylene(carbocycle), —C$_6$-C$_{10}$ aryl, —C$_1$-C$_{20}$ alkylene(aryl), —C$_2$-C$_{20}$ alkenylene(aryl), —C$_2$-C$_{20}$ alkynylene(aryl), —C$_1$-C$_{20}$ alkylene(heterocycle), —C$_2$-C$_{20}$ alkenylene(heterocycle), or —C$_2$-C$_{20}$ alkynylene(heterocycle) wherein said alkyl, alkenyl, alkynyl, alkylene, alkenylene, alkynylene, aryl, carbocycle, and heterocycle radicals whether alone or as part of another group are optionally substituted.

"Altering the native glycosylation pattern" is intended for purposes herein to mean deleting one or more carbohydrate moieties found in native sequence 161P2F10B (either by removing the underlying glycosylation site or by deleting the glycosylation by chemical and/or enzymatic means), and/or adding one or more glycosylation sites that are not present in the native sequence 161P2F10B. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g., a 161P2F10B-related protein). For example, an analog of a 161P2F10B protein can be specifically bound by an antibody or T cell that specifically binds to 161P2F10B.

The term "antibody" is used in the broadest sense unless clearly indicated otherwise. Therefore, an "antibody" can be naturally occurring or man-made such as monoclonal antibodies produced by conventional hybridoma technology. 161P2F10B antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds 161P2F10B and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind 161P2F10B and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a IgG1, IgG2, IgG3, or IgG4 antibody. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition). An antibody of the present invention can be modified by recombinant means to increase efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., *Mol. Immunol.* 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective 161P2F10B. See e.g., *Antibody Engineering: A Practical Approach* (Oxford University Press, 1996). Suitable antibodies with the desired biologic activities can be identified the following in vitro assays including but not limited to: proliferation, migration, adhesion, soft agar growth, angiogenesis, cell-cell communication, apoptosis, transport, signal transduction, liternalization, antibody mediated secondary killing, and the following in vivo assays such as the inhibition of tumor growth. The antibody provided herein can be useful as an intermediate of ADC. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the 161P2F10B or its receptor.

The term "antigen-binding portion" or "antibody fragment" of an antibody (or simply "antibody portion"), as used herein, refers to one or more fragments of a 161P2F10B antibody that retain the ability to specifically bind to an antigen (e.g., 161P2F10B; FIG. 1). It has been shown that the antigen-binding function of an antibody can be performed by fragments of a full-length antibody. Examples of binding fragments encompassed within the term "antigen-binding portion" of an antibody include (i) an Fab fragment, a monovalent fragment consisting of the $V_L$, $V_H$, $C_L$ and $C_{H1}$ domains; (ii) an F(ab')$_2$ fragment, a bivalent fragment comprising two Fab fragments linked by a disulfide bridge at the hinge region; (iii) an Fd fragment consisting of the $V_H$ and $C_{H1}$ domains; (iv) an Fv fragment consisting of the $V_L$ and $V_H$ domains of a single arm of an antibody, (v) a dAb fragment (Ward, et al. (1989) *Nature* 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird, et al. (1988) *Science* 242:423-426; and Huston, et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

As used herein, any form of the "antigen" can be used to generate an antibody that is specific for 161P2F10B. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e g , immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the 161P2F10B of interest.

The antibodies or antigen binding fragments thereof provided herein may be conjugated to a "bioactive agent." As used herein, the term "bioactive agent" refers to any synthetic or naturally occurring compound that binds the antigen and/or enhances or mediates a desired biological effect to enhance cell-killing toxins. In one embodiment, the binding fragments useful in the present invention are biologically active fragments. As used herein, the term "biologically active" refers to an antibody or antibody fragment that is capable of binding the desired antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison, et al., *Proc. Natl. Acad. Sci. USA* 81: 6851-6855 (1984)).

The term "Chemotherapeutic Agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites, for example, folic acid, purine or pyrimidine antagonists; mitotic inhibitors, for example, anti-tubulin agents such as vinca alkaloids, auristatins and derivatives of podophyllotoxin; cytotoxic antibiotics; compounds that damage or interfere with DNA expression or replication, for example, DNA minor groove binders; and growth factor receptor antagonists. In addition, chemotherapeutic agents include cytotoxic agents (as defined herein), antibodies, biological molecules and small molecules.

The term "compound" refers to and encompasses the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc., forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates, however, this reference is for emphasis only, and is not to be construed as excluding other of the above forms as identified above.

The term "cytotoxic agent" refers to a substance that inhibits or prevents the expression activity of cells, function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to auristatins (e.g., auristatin e, auristatin f, MMAE and MMAF), auromycins, maytansinoids, ricin, ricin A-chain, combretastatin, duocarmycins, dolastatins, doxorubicin, daunorubicin, taxols, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, restrictocin, phenomycin, enomycin, curicin, crotin, calicheamicin, Saponaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive isotopes of Lu including $Lu^{177}$. Antibodies may also be conjugated to an anti-cancer pro-drug activating enzyme capable of converting the pro-drug to its active form.

The term "deplete," in the context of the effect of a 161P2F10B binding agent on 161P2F10B-expressing cells, refers to a reduction in the number of or elimination of the 161P2F10B-expressing cells.

The "gene product" is used herein to indicate a peptide/protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 1. The cancer protein can be a fragment, or alternatively, be the full-length protein encoded by nucleic acids of FIG. 1. In one embodiment, a cancer amino acid sequence is used to determine sequence identity or similarity. In another embodiment, the sequences are naturally occurring allelic variants of a protein encoded by a nucleic acid of FIG. 1. In another embodiment, the sequences are sequence variants as further described herein.

"Heteroconjugate" antibodies are useful in the present methods and compositions. As used herein, the term "heteroconjugate antibody" refers to two covalently joined antibodies. Such antibodies can be prepared using known methods in synthetic protein chemistry, including using crosslinking agents. See, e.g., U.S. Pat. No. 4,676,980.

The term "homolog" refers to a molecule which exhibits homology to another molecule, by for example, having sequences of chemical residues that are the same or similar at corresponding positions.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., Kozbor, et al., *Immunol. Today* 4: 72 (1983), EBV transformation technique (see, e.g., Cole, et al. *Monoclonal Antibodies And Cancer Therapy* 77-96 (1985)), or using phage display (see, e.g., Marks, et al., *J. Mol. Biol.* 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569,825; 5,625,126; 5,633,425; 5,661,016; and 5,545,806; and Jakobovits, *Adv. Drug Del. Rev.* 31:33-42 (1998); Green, et al., *J. Exp. Med.* 188:483-95 (1998).

The terms "inhibit" or "inhibition of" as used herein means to reduce by a measurable amount, or to prevent entirely.

Suitable "labels" include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. In addition, the antibodies provided herein can be useful as the antigen-binding component of fluorobodies. See e.g., Zeytun, et al., *Nat. Biotechnol.* 21:1473-79 (2003).

The terms "metastatic cancer" and "metastatic disease" mean cancers that have spread to regional lymph nodes or to distant sites, and are meant to include stage D disease under the AUA system and stage T×N×M+ under the TNM system.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g., to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates, or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson, et al., Nature 352: 624-628 (1991) and Marks, et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 1, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

A "recombinant" DNA or RNA molecule is a DNA or RNA molecule that has been subjected to molecular manipulation in vitro.

As used herein, the terms "specific", "specifically binds" and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that binds the 161P2F10B-related antigen (particularly 161P2F10B), but does not bind to the irrelevant antigen.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred out albeit not a requirement for a treatment act.

The "161P2F10B-related proteins" include those specifically identified herein (see, FIG. 1), as well as allelic variants, conservative substitution variants, analogs and homologs that can be isolated/generated and characterized without undue experimentation following the methods outlined herein or readily available in the art. Fusion proteins that combine parts of different 161P2F10B proteins or fragments thereof, as well as fusion proteins of a 161P2F10B protein and a heterologous polypeptide are also included. Such 161P2F10B proteins are collectively referred to as the 161P2F10B-related proteins, the proteins of the invention, or 161P2F10B. The term "161P2F10B-related protein" refers to a polypeptide fragment or a 161P2F10B protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 330, 335, 339 or more amino acids.

II.) 161P2F10B Antibodies

Antibodies for ADCs of the invention specifically bind to a 161P2F10B protein and do not bind (or bind weakly) to peptides or proteins that are not 161P2F10B-related proteins under physiological conditions.

Various methods for the preparation of antibodies, specifically monoclonal antibodies, are well known in the art. For example, antibodies can be prepared by immunizing a suitable mammalian host using a 161P2F10B-related protein, peptide, or fragment thereof, in isolated or immunoconjugated form (Antibodies: *A Laboratory Manual*, CSH Press, Eds., Harlow, and Lane (1988); Harlow, *Antibodies*, Cold Spring Harbor Press, NY (1989)). In addition, fusion proteins of 161P2F10B can also be used, such as a 161P2F10B GST-fusion protein. In a particular embodiment, a GST fusion protein comprising all or most of the amino acid sequence of FIG. 1 is produced, and then used as an immunogen to generate appropriate antibodies. In another embodiment, a 161P2F10B-related protein is synthesized and used as an immunogen.

In addition, naked DNA immunization techniques known in the art are used (with or without purified 161P2F10B-related protein or 161P2F10B expressing cells) to generate an immune response to the encoded immunogen (for review, see Donnelly, et al., 1997, *Ann. Rev. Immunol.* 15: 617-648).

The amino acid sequence of a 161P2F10B protein as shown in FIG. 1 can be analyzed to select specific regions of the 161P2F10B protein for generating antibodies. For example, hydrophobicity and hydrophilicity analyses of a 161P2F10B amino acid sequence are used to identify hydrophilic regions in the 161P2F10B structure. Regions of a 161P2F10B protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, *Proc. Natl. Acad. Sci. U.S.A.* 78:3824-3828. Hydropathicity profiles can be generated using the method of Kyte, J. and Doolittle, R. F., 1982, *J. Mol. Biol.* 157:105-132. Percent (%) Accessible Residues profiles can be generated using the method of Janin J., 1979, *Nature* 277:491-492. Average Flexibility profiles can be generated using the method of Bhaskaran R., Ponnuswamy P. K., 1988, *Int. J. Pept. Protein Res.* 32:242-255. Beta-turn profiles can be generated using the method of Deleage, G., Roux B., 1987, *Protein Engineering* 1:289-294. Thus, each region identified by any of these programs or methods is within the scope of the present invention. Preferred methods for the generation of 161P2F10B antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 161P2F10B immunogen is often conducted by injection over a suitable time period and with use of a suitable adjuvant, as is understood in the art. During the immunization schedule, titers of antibodies can be taken to determine adequacy of antibody formation.

In a preferred embodiment, a 161P2F10B MAb for ADCs of the invention comprises heavy and light chain variable regions of an antibody designated H16-7.8 (See, FIG. 3), or heavy and light variable regions comprising amino acid sequences that are homologous to the amino acid sequences of the heavy and light chain variable regions of H16-7.8, and wherein the antibodies retain the desired functional properties (particularly binding activity to 161P2F10B) of the 161P2F10B MAbs of the invention. The heavy chain variable region of H16-7.8 consists of the amino acid sequence ranging from $20^{th}$ Q residue to the $142^{nd}$ S residue of SEQ ID NO:7, and the light chain variable region of H16-7.8 consists of the amino acid sequence ranging from $20^{th}$ E residue to the $127^{th}$ R residue of SEQ ID NO:8. As the constant region of the antibody of the invention, any subclass of constant region can be chosen. Preferably, human IgG2 constant region as the heavy chain constant region and human Ig kappa constant region as the light chain constant region can be used. Reactivity (binding activity) of 161P2F10B MAbs with a 161P2F10B protein can be established by a number of well known means, including Western blot, immunoprecipitation, ELISA, and FACS analyses using 161P2F10B proteins, 161P2F10B-expressing cells or extracts thereof.

In one embodiment, the hinge region of CH1 is modified such that the number of cysteine residues in the hinge region is altered, e.g., increased or decreased. This approach is described further in U.S. Pat. No. 5,677,425 by Bodmer, et al. The number of cysteine residues in the hinge region of CH1 is altered to, for example, facilitate assembly of the light and heavy chains or to increase or decrease the stability of the 161P2F10B MAb.

In another embodiment, the Fc hinge region of an antibody is mutated to decrease the biological half life of the 161P2F10B MAb. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward, et al.

In another embodiment, the 161P2F10B MAb is modified to increase its biological half life. Various approaches are possible. For example, mutations can be introduced as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta, et al.

In yet other embodiments, the Fc region is altered by replacing at least one amino acid residue with a different amino acid residue to alter the effector function(s) of the 161P2F10B MAb. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter, et al.

In one embodiment, the antibody for ADC of the present invention is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, ANTIBODY PRODUCTION: ESSENTIAL TECHNIQUES (Wiley, 1997); Shephard, et al., Monoclonal Antibodies (Oxford University Press, 2000); Goding, Monoclonal Antibodies: Principles And Practice (Academic Press, 1993); Current Protocols In Immunology (John Wiley & Sons, most recent edition).

The antibody for ADC of the present invention can easily be prepared by those skilled in the art on the basis of the sequence information on the heavy-chain variable region and light-chain variable region thereof disclosed herein, using a method commonly known in the art. Specifically, a heavy-chain variable region gene fragment having a base sequence that encodes the heavy-chain variable region amino acid of the antibody for ADC of the present invention (SEQ ID NO:7, from 20 to 142), and a light-chain variable region gene fragment having a base sequence that encodes the light-chain variable region amino acid of the antibody for ADC of the present invention (SEQ ID NO:8, from 20 to 127) are prepared. Then, the variable region genes are joined to a constant region gene in an appropriate class of human antibody to prepare an antibody gene. Next, this antibody gene is joined to an appropriate expression vector, and introduced to a cultured cell. Finally, this cultured cell is cultured, whereby the antibody can be obtained from the culture supernatant.

Each of the above-described variable region gene fragments that encode the heavy-chain and light-chain variable region amino acids of the antibody of the present invention (SEQ ID NO:7, from 20 to 142 and SEQ ID NO:8, from 20 to 127) can be prepared by on the basis of base sequences designed on the basis of the amino acid sequences of the heavy-chain and light-chain variable regions (SEQ ID NO:7, from 20 to 142 and SEQ ID NO:8, from 20 to 127), or on the basis of the base sequences of the heavy-chain and light-chain variable regions of the antibody of the present invention, shown by SEQ ID NO:4, from 91 to 459 and SEQ ID NO:6, from 100 to 423, using a method of gene synthesis commonly known in the art. As such a method of gene synthesis, various methods obvious to those skilled in the art, such as the antibody gene synthesis method described in WO90/07861, can be used. Next, the above-described variable region gene fragments and the constant region gene of the human antibody are joined to prepare an antibody gene. Although any subclass of constant region can be chosen as the constant region of the human antibody used, human Ig[gamma]2 as the heavy-chain constant region, and human Ig[kappa] as the light-chain constant region, can be preferably used.

As the preferable antibody heavy-chain gene of the antibody for ADC of present invention, obtained by joining the heavy-chain variable region gene shown by SEQ ID NO:7, from 20 to 142 and the human Ig[gamma]2 heavy-chain constant region gene, a gene comprising a base sequence that encodes the amino acid sequence shown by SEQ ID NO:7, from 20 to 468, more preferably a gene comprising the base sequence shown by SEQ ID NO:4, from 91 to 1437, can be mentioned. As the preferable antibody light-chain gene of the antibody for ADC of present invention, obtained by joining the light-chain variable region gene shown by SEQ ID NO:8, from 20 to 127 and the human Ig[kappa] light-chain constant region gene, a gene comprising a base sequence that encodes the amino acid sequence shown by SEQ ID NO:8, from 20 to 233, more preferably a gene comprising the base sequence shown by SEQ ID NO:6, from 100 to 741, can be mentioned. As the antibody for ADC of the present invention, encoded by a heavy-chain gene comprising the base sequence shown by SEQ ID NO:4, from 91 to 1437 and a light-chain gene comprising the base sequence shown by SEQ ID NO:6, from 100 to 741, H16-7.8, described in an Example below, can be mentioned.

Subsequent to the preparation of this antibody gene, introduction of the antibody gene to an expression vector, introduction of the expression vector to cultured cells, cultivation of the cultured cells, purification of the antibody and the like can be performed by using various methods commonly known in the art. The expression vector is not subject to limitation, as long as it is capable of expressing the antibody gene. It is preferable to utilize an expression vector already having a human Ig constant region gene such as AG-[gamma]2 or AG-[kappa], because it would become an expression vector having the antibody gene simply when the antibody variable region gene is inserted thereto.

The above-described expression vector is introduced to cultured cells by, for example, the calcium phosphate method and the like. As examples of the cultured cells to which the expression vector is introduced, cultured cells such as CHO cells can be used, and they may be cultured by a conventional method. After the above-described cultivation, the antibody accumulated in the culture supernatant can be purified by, for example, various chromatographies using a Protein A column.

Reactivity(binding activity) of 161P2F10B antibodies thus obtained with a 161P2F10B protein can be established by a number of well known means, including Western blot, immunoprecipitation, ELISA, and FACS analyses using, as appropriate, 161P2F10B protein, 161P2F10B-expressing cells or extracts thereof. The antibody thus obtained or an antibody fragment retaining an activity due to the antibody after being further purified as required, can be prepared as an antibody for ADC. A 161P2F10B antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 161P2F10B epitopes are generated using methods generally known in the art. Homodimeric antibodies can also be generated by cross-linking techniques known in the art (e.g., Wolff, et al., *Cancer Res.* 53: 2560-2565).

In yet another preferred embodiment, the 161P2F10B MAb for ADCs of the invention is an antibody comprising heavy and light chain of an antibody designated H16-7.8. The heavy chain of H16-7.8 consists of the amino acid sequence ranging from $20^{th}$ Q residue to the $468^{th}$ K residue of SEQ ID NO:7 and the light chain of H16-7.8 consists of amino acid sequence ranging from $20^{th}$ E residue to the $233^{rd}$ C residue of SEQ ID NO:8 sequence. The sequence of which is set forth in FIG. 2 and FIG. 3. In a preferred embodiment, H16-7.8 is conjugated to a cytotoxic agent.

III.) Antibody-Drug Conjugates Generally

In another aspect, the invention provides antibody-drug conjugates (ADCs), comprising an antibody conjugated to a cytotoxic agent such as MMAF. In another aspect, the invention further provides methods of using the ADCs. In one aspect, an ADC comprises any of the above 161P2F10B MAbs covalently attached to a cytotoxic agent.

The use of antibody-drug conjugates for the local delivery of cytotoxic or cytostatic agents, i.e., drugs to kill or inhibit tumor cells in the treatment of cancer (Syrigos and Epenetos (1999) *Anticancer Research* 19:605-614; Niculescu-Duvaz and Springer (1997) *Adv. Drg Del. Rev.* 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin, et al., (1986) *Lancet* pp. (Mar. 15, 1986):603-05; Thorpe, (1985)

"Antibody Carriers Of Cytotoxic Agents In Cancer Therapy: A Review," in *Monoclonal Antibodies '84: Biological And Clinical Applications*, A. Pinchera, et al. (ed.s), pp. 475-506). Maximal efficacy with minimal toxicity is sought thereby. Both polyclonal antibodies and monoclonal antibodies have been reported as useful in these strategies (Rowland, et al. (1986) *Cancer Immunol. Immunother.*, 21:183-87). Drugs used in these methods include daunomycin, doxorubicin, methotrexate, and vindesine (Rowland, et al., (1986) supra). Toxins used in antibody-toxin conjugates include bacterial toxins such as diphtheria toxin, plant toxins such as ricin, small molecule toxins such as geldanamycin (Mandler, et al. (2000) *Jour. of the Nat. Cancer Inst.* 92(19):1573-1581; Mandler, et al. (2000) *Bioorganic & Med. Chem. Letters* 10:1025-1028; Mandler, et al. (2002) *Bioconjugate Chem.* 13:786-791), maytansinoids (EP 1391213; Liu, et al. (1996) *Proc. Natl. Acad. Sci. USA* 93:8618-8623), and calicheamicin (Lode, et al. (1998) *Cancer Res.* 58:2928; Hinman, et al. (1993) *Cancer Res.* 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Examples of antibody drug conjugates are, ZEVALIN® (ibritumomab tiuxetan, Biogen/Idec) which is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman, et al. (2000) *Eur. Jour. Nucl. Med.* 27(7): 766-77; Wiseman, et al. (2002) Blood 99(12):4336-42; Witzig, et al. (2002) *J. Clin. Oncol.* 20(10):2453-63; Witzig, et al. (2002) *J. Clin. Oncol.* 20(15):3262-69).

Additionally, MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (*Drugs of the Future* (2000) 25(7):686; U.S. Pat. Nos. 4,970,198; 5,079,233; 5,585,089; 5,606,040; 5,693,762; 5,739,116; 5,767,285; and 5,773,001).

In addition, Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others.

Additionally, MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors.

Finally, the auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronin, et al. (2003) *Nature Biotechnology* 21(7):778-784) and are under therapeutic development.

III (A). Auristatins and Dolostatins

Dolastatins and auristatins have been shown to interfere with microtubule dynamics, GTP hydrolysis, and nuclear and cellular division (Woyke, et al. (2001) *Antimicrob. Agents and Chemother.* 45(12):3580-3584) and have anticancer (U.S. Pat. No. 5,663,149) and antifungal activity (Pettit, et al. (1998) *Antimicrob. Agents Chemother.* 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in Senter, et al, "Proceedings of the American Association for Cancer Research," Volume 45, Abstract Number 623, and presented Mar. 28, 2004, the disclosure of which is expressly incorporated by reference in its entirety.

An exemplary auristatin embodiment is MMAE (wherein the wavy line indicates the covalent attachment to a linker (L) of an antibody drug conjugate).

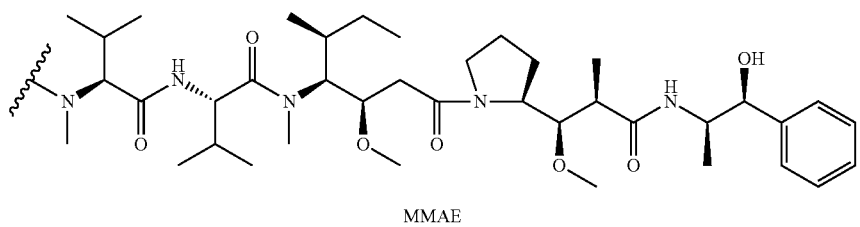 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

Another exemplary auristatin embodiment is MMAF, wherein the wavy line indicates the covalent attachment to a linker (L) of an antibody drug conjugate (US 2005/0238649):

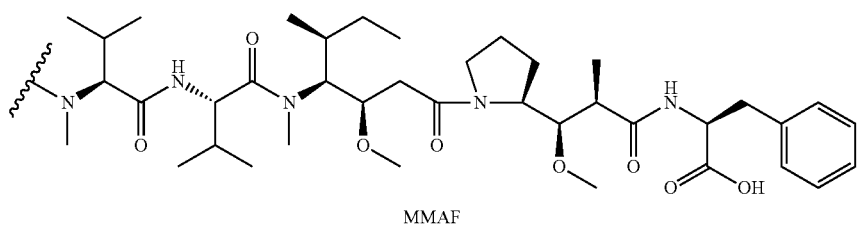

MMAF

Additional exemplary embodiments comprising MMAE or MMAF and various linker components (described further herein) have the following structures and abbreviations (wherein Ab means antibody and p is 1 to about 12):

activity against cells expressing 161P2F10B. The antibody-drug conjugate compounds comprise an Antibody unit covalently linked to at least one Drug unit. The Drug units can be covalently linked directly or via a Linker unit (-LU-).

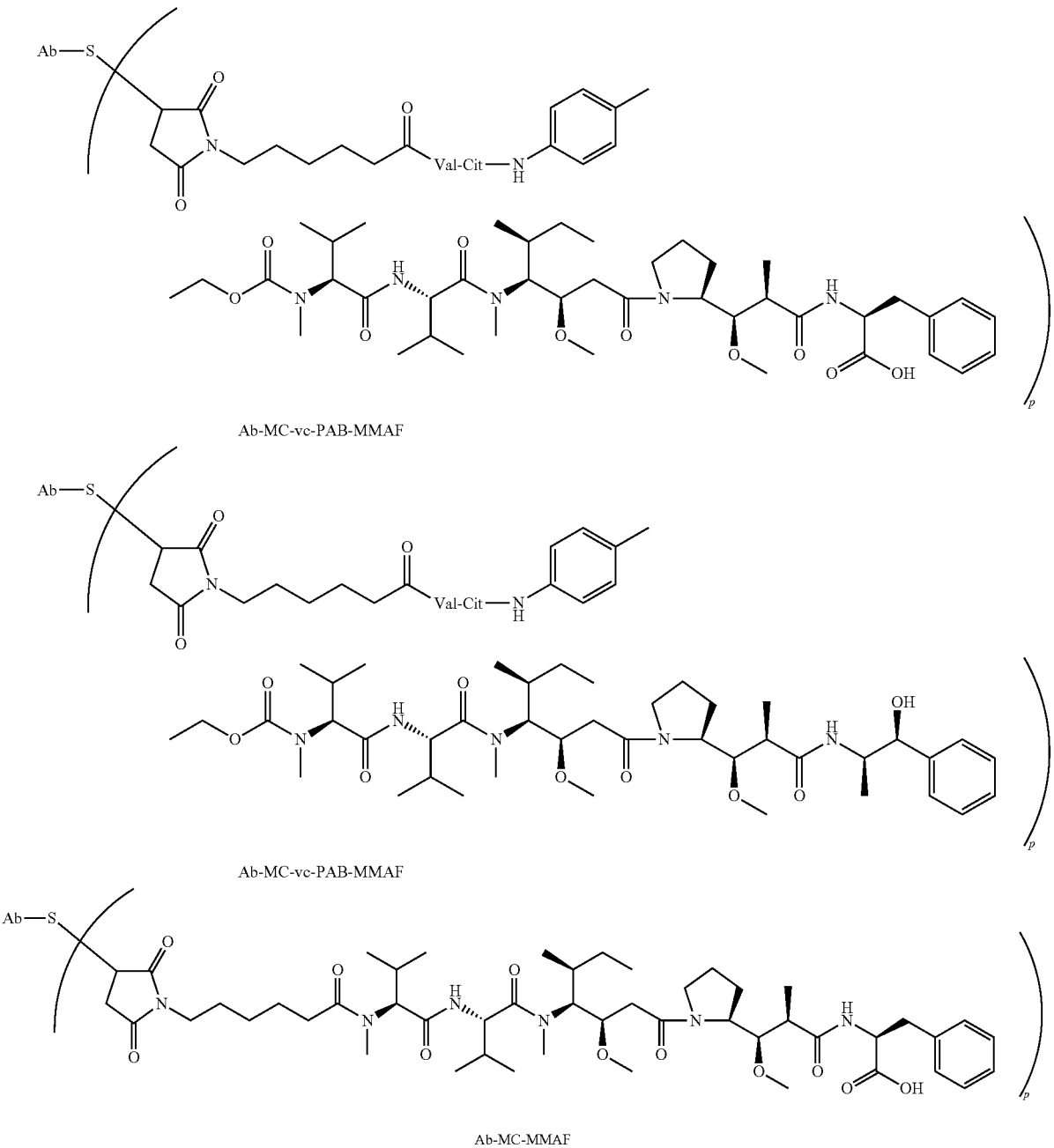

ADC of the present invention include MMAF. The preferred embodiment, the ADC of the present invention include maleimidocaproyl (mc) as a linker and MMAF as a drug.

IV.) Antibody-Drug Conjugate Compounds which Bind 161P2F10B

The present invention provides, inter alia, antibody-drug conjugate compounds for targeted delivery of drugs. The inventors have made the discovery that the antibody-drug conjugate compounds have potent cytotoxic and/or cytostatic In some embodiments, the antibody drug conjugate compound has the following formula:

$$L\text{-}(LU\text{-}D)_p \quad (I)$$

or a pharmaceutically acceptable salt or solvate thereof; wherein:
L is the Antibody unit, e.g., 161P2F10B MAb of the present invention, and
(LU-D) is a Linker unit-Drug unit moiety, wherein:
LU- is a Linker unit, and -D is a drug unit having cytostatic or cytotoxic activity against a target cell; and p is an integer from 1 to 20.

In some embodiments, p ranges from 1 to 12, 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6. In some embodiments, p is 2 or 4.

In some embodiments, the antibody drug conjugate compound has the following formula:

$$L\text{-}(A_a\text{-}W_w\text{-}Y_y\text{-}D)_p \quad (II)$$

or a pharmaceutically acceptable salt or solvate thereof, wherein:

L is the Antibody unit, e.g., 161P2F10B MAb; and
$-A_a\text{-}W_w\text{-}Y_y\text{-}$ is a Linker unit (LU), wherein:
-A- is a Stretcher unit,
a is 0 or 1,
each -W- is independently an Amino Acid unit,
w is an integer ranging from 0 to 12,
-Y- is a self-immolative spacer unit,
y is 0, 1 or 2;
-D is a drug units having cytostatic or cytotoxic activity against the target cell; and
p is an integer from 1 to 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 12, 1 to 10, 1 to 9, 1 to 8, 1 to 7, 1 to 6, 1 to 5, 1 to 4, 1 to 3, or 1 to 2. In some embodiments, p ranges from 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

For compositions comprising a plurality of antibodies, the drug loading is represented by p, the average number of drug molecules per Antibody. Drug loading may range from 1 to 12 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is from 2 to 8.

The generation of Antibody-drug conjugate compounds can be accomplished by any technique known to the skilled artisan. Briefly, the Antibody-drug conjugate compounds comprise 161P2F10B MAb as the Antibody unit, a drug, and optionally a linker that joins the drug and the binding agent. In a preferred embodiment, the Antibody is 161P2F10B MAb comprising heavy and light chain variable regions of an antibody designated H16-7.8 described above. In more preferred embodiment, the Antibody is 161P2F10B MAb comprising heavy and light chain of an antibody designated H16-7.8 described above. A number of different reactions are available for covalent attachment of drugs and/or linkers to binding agents. This is often accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the 161P2F10B MAb under appropriate conditions.

Each of the particular units of the Antibody-drug conjugate compounds is described in more detail herein. The synthesis and structure of exemplary linker units, stretcher units, amino acid units, self-immolative spacer unit, and drug units are also described in U.S. Patent Application Publication Nos. 2003-0083263, 2005-0238649 and 2005-0009751, each if which is incorporated herein by reference in its entirety and for all purposes.

V.) Linker Units

Typically, the antibody-drug conjugate compounds comprise a linker region between the drug unit and the antibody unit. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, *Pharm. Therapeutics* 83:67-123). Most typical are peptidyl linkers that are cleavable by enzymes that are present in 161P2F10B-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO:9). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville, et al., 1989, *Biol. Chem.* 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe, et al., 1987, *Cancer Res.* 47:5924-5931; Wawrzynczak, et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson, et al., 1995, *Anticancer Res.* 15:1387-93), a maleimidobenzoyl linker (Lau, et al., 1995, *Bioorg-Med-Chem.* 3(10):1299-1304), or a 3'-N-amide analog (Lau, et al., 1995, *Bioorg-Med-Chem.* 3(10):1305-12).

In yet other embodiments, the linker unit is not cleavable and the drug is released by antibody degradation. (See U.S. Publication No. 2005/0238649 incorporated by reference herein in its entirety and for all purposes). In preferred embodiment, linker unit is maleimidocaproyl (mc).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound presents in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the antibody-drug conjugate compound as described herein). In yet other embodiments, the linker promotes cellular internalization when conjugated to both the auristatin compound and the 161P2F10B MAb.

A variety of exemplary linkers that can be used with the present compositions and methods are described in WO2004-010957, U.S. Publication No. 20060074008, U.S. Publication No. 20050238649, and U.S. Publication No. 20060024317 (each of which is incorporated by reference herein in its entirety and for all purposes).

A "Linker unit" (LU) is a bifunctional compound that can be used to link a Drug unit and a Antibody unit to form an antibody-drug conjugate compound. In some embodiments, the Linker unit has the formula:

wherein: -A- is a Stretcher unit,
a is 0 or 1,
each -W- is independently an Amino Acid unit,
w is an integer ranging from 0 to 12,
-Y- is a self-immolative Spacer unit, and
y is 0, 1 or 2.

In some embodiments, a is 0 or 1, w is 0 or 1, and y is 0, 1 or 2. In some embodiments, a is 0 or 1, w is 0 or 1, and y is 0 or 1. In some embodiments, when w is 1 to 12, y is 1 or 2. In some embodiments, w is 2 to 12 and y is 1 or 2. In some embodiments, a is 1 and w and y are 0.

VI.) The Stretcher Unit

The Stretcher unit (A), when present, is capable of linking an Antibody unit to an Amino Acid unit (-W-), if present, to a Spacer unit (-Y-), if present; or to a Drug unit (-D). Useful functional groups that can be present on a 161P2F10B MAb (e.g., H16-7.8), either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of a 161P2F10B MAb. In another embodiment, sulfhydryl groups can be generated by reaction of an amino group of a lysine moiety of a 161P2F10B MAb with 2-iminothiolane (Traut's reagent) or other sulfhydryl generating reagents. In certain embodiments, the 161P2F10B MAb is a recombinant antibody and is engineered to carry one or more lysines. In certain other embodiments, the recombinant 161P2F10B MAb is engineered to carry additional sulfhydryl groups, e.g., additional cysteines.

In one embodiment, the Stretcher unit forms a bond with a sulfur atom of the Antibody unit. The sulfur atom can be derived from a sulfhydryl group of an antibody. Representative Stretcher units of this embodiment are depicted within the square brackets of Formulas IIIa and IIIb, wherein L-, -W-, -Y-, -D, w and y are as defined above, and $R^{17}$ is selected from —$C_1$-$C_{10}$ alkylene-, —$C_1$-$C_{10}$ alkenylene-, —$C_1$-$C_{10}$ alkynylene-, -carbocyclo-, —O—($C_1$-$C_8$ alkylene)-, O—($C_1$-$C_8$ alkenylene)-, —O—($C_1$-$C_8$ alkynylene)-, -arylene-, —$C_1$-$C_{10}$ alkylene-arylene-, —$C_2$-$C_{10}$ alkenylene-arylene, —$C_2$-$C_{10}$ alkynylene-arylene, -arylene-$C_1$-$C_{10}$ alkylene-, -arylene-$C_2$-$C_{10}$ alkenylene-, -arylene-$C_2$-$C_{10}$ alkynylene-, —$C_1$-$C_{10}$ alkylene-(carbocyclo)-, —$C_2$-$C_{10}$ alkenylene-(carbocyclo)-, —$C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, -heterocyclo-, —$C_1$-$C_{10}$ alkylene-(heterocyclo)-, —$C_2$-$C_{10}$ alkenylene-(heterocyclo)-, —$C_2$-$C_{10}$ alkynylene-(heterocyclo)-, -(heterocyclo)-$C_1$-$C_{10}$ alkylene-, -(heterocyclo)-$C_2$-$C_{10}$ alkenylene-, -(heterocyclo)-$C_1$-$C_{10}$ alkynylene-, —($CH_2CH_2O)_r$—, or —($CH_2CH_2O)_r$—$CH_2$—, and r is an integer ranging from 1-10, wherein said alkyl, alkenyl, alkynyl, alkylene, alkenylene, alkynyklene, aryl, carbocycle, carbocyclo, heterocyclo, and arylene radicals, whether alone or as part of another group, are optionally substituted. In some embodiments, said alkyl, alkenyl, alkynyl, alkylene, alkenylene, alkynyklene, aryl, carbocyle, carbocyclo, heterocyclo, and arylene radicals, whether alone or as part of another group, are unsubstituted. In some embodiments, $R^{17}$ is selected from —$C_1$-$C_{10}$ alkylene-, -carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-(carbocyclo)-, -(carbocyclo)-$C_1$-$C_{10}$ alkylene-, —$C_3$-$C_8$ heterocyclo-, —$C_1$-$C_{10}$ alkylene-(heterocyclo)-, -(heterocyclo)-$C_1$-$C_{10}$ alkylene-, —($CH_2CH_2O$)$_r$—, and —($CH_2CH_2O$)$_r$—$CH_2$—; and r is an integer ranging from 1-10, wherein said alkylene groups are unsubstituted and the remainder of the groups are optionally substituted.

It is to be understood from all the exemplary embodiments that even where not denoted expressly, from 1 to 12 drug moieties can be linked to an Antibody (p=1-12).

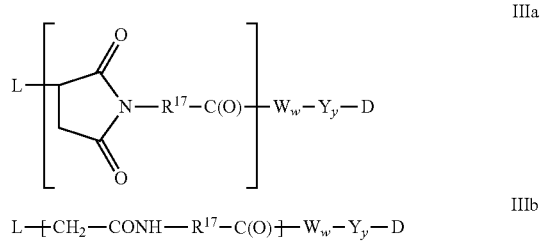

IIIa

IIIb

An illustrative Stretcher unit is that of Formula Ma wherein $R^{17}$ is —($CH_2$)$_5$—:

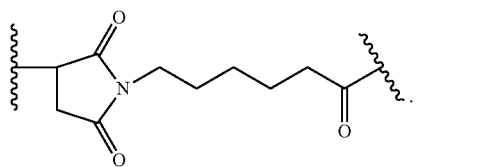 [SMILES: *C(=O)CCCCCN1C(=O)CC(*)C1=O]

Another illustrative Stretcher unit is that of Formula IIIa wherein $R^{17}$ is —($CH_2CH_2O$)$_r$—$CH_2$—; and r is 2:

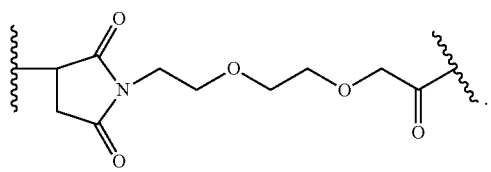 [SMILES: *C(=O)COCCOCCN1C(=O)CC(*)C1=O]

An illustrative Stretcher unit is that of Formula Ma wherein $R^{17}$ is -arylene- or arylene-$C_1$-$C_{10}$ alkylene-. In some embodiments, the aryl group is an unsubstituted phenyl group.

Still another illustrative Stretcher unit is that of Formula IIIb wherein $R^{17}$ is —($CH_2$)$_5$—:

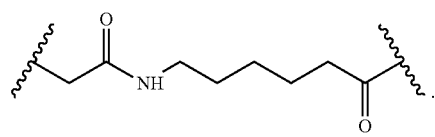 [SMILES: *CC(=O)NCCCCCC(*)=O]

In certain embodiments, the Stretcher unit is linked to the Antibody unit via a disulfide bond between a sulfur atom of the Antibody unit and a sulfur atom of the Stretcher unit. A representative Stretcher unit of this embodiment is depicted within the square brackets of Formula IV, wherein $R^{17}$, L-, -W-, -Y-, -D, w and y are as defined above.

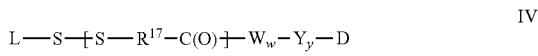

IV

It should be noted that throughout this application, the S moiety in the formula below refers to a sulfur atom of the Antibody unit, unless otherwise indicated by context.

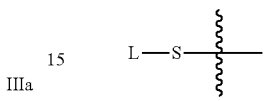

In yet other embodiments, the Stretcher contains a reactive site that can form a bond with a primary or secondary amino group of an Antibody. Examples of these reactive sites include, but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, L-, -W-, -Y-, -D, w and y are as defined above;

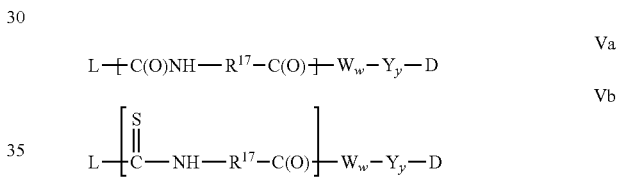

Va

Vb

In some embodiments, the Stretcher contains a reactive site that is reactive to a modified carbohydrate's (—CHO) group that can be present on an Antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko, et al., 1991, *Bioconjugate Chem.* 2:133-41. Representative Stretcher units of this embodiment are depicted within the square brackets of Formulas VIa, VIb, and VIc, wherein —$R^{17}$—, L-, -W-, -Y-, -D, w and y are as defined as above.

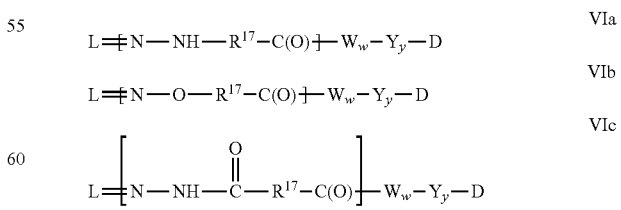

VIa

VIb

VIc

VII.) The Amino Acid Unit

The Amino Acid unit (-W-), when present, links the Stretcher unit to the Spacer unit if the Spacer unit is present, links the Stretcher unit to the Drug moiety if the Spacer unit is absent, and links the Antibody unit to the Drug unit if the Stretcher unit and Spacer unit are absent.

$W_w$- can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each -W- unit independently has the formula denoted below in the square brackets, and w is an integer ranging from 0 to 12:

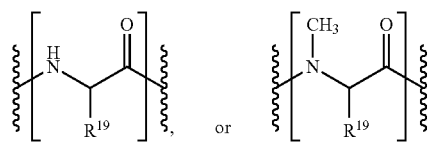

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

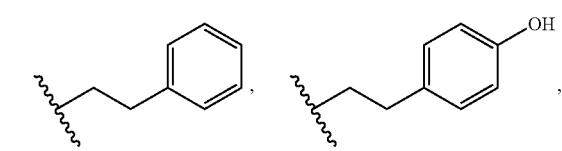

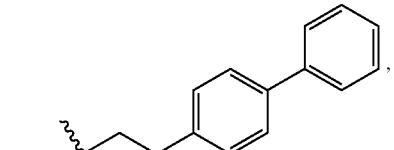

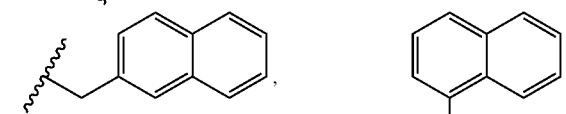

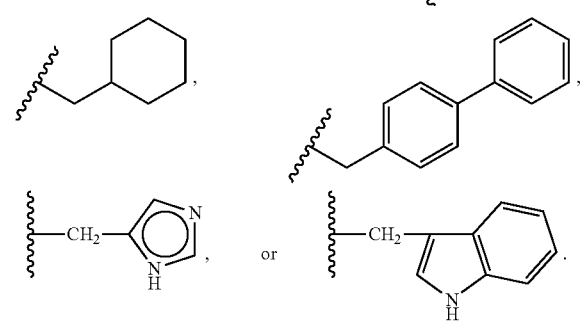

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In certain embodiments, the Amino Acid unit can comprise natural amino acids. In other embodiments, the Amino Acid unit can comprise non-natural amino acids. Illustrative Ww units are represented by formulas (VII)-(IX):

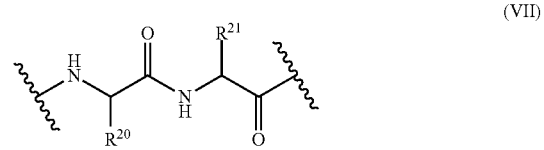

(VII)

wherein $R^{20}$ and $R^{21}$ are as follows:

| $R^{20}$ | $R^{21}$ |
|---|---|
| Benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| 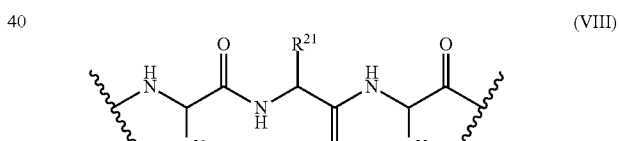 | $(CH_2)_3NHCONH_2$; |
| benzyl | methyl; |
| benzyl | $(CH_2)_3NHC(=NH)NH_2$; |

(VIII)

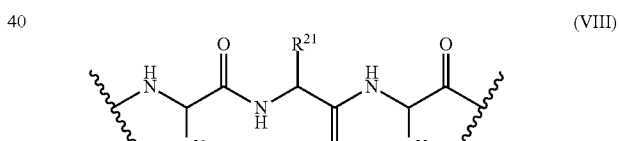

wherein $R^{20}$, $R^{21}$ and $R^{22}$ are as follows:

| $R^{20}$ | $R^{21}$ | $R^{22}$ |
|---|---|---|
| benzyl | benzyl | $(CH_2)_4NH_2$; |
| isopropyl | benzyl | $(CH_2)_4NH_2$; and |
| H | benzyl | $(CH_2)_4NH_2$; |

(IX)

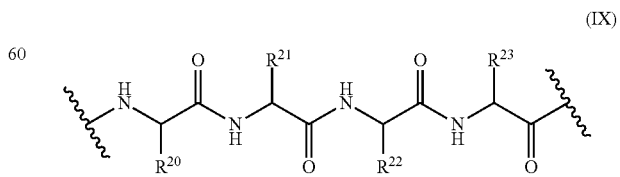

wherein $R^{20}$, $R^{21}$, $R^{22}$ and $R^{23}$ are as follows:

| $R^{20}$ | $R^{21}$ | $R^{22}$ | $R^{23}$ |
|---|---|---|---|
| H | benzyl | isobutyl | H; and |
| methyl | isobutyl | methyl | isobutyl. |

Exemplary Amino Acid units include, but are not limited to, units of formula VII where: $R^{20}$ is benzyl and $R^{21}$ is —$(CH_2)_4NH_2$; $R^{20}$ is isopropyl and $R^{21}$ is —$(CH_2)_4NH_2$; or $R^{20}$ is isopropyl and $R^{21}$ is —$(CH_2)_3NHCONH_2$. Another exemplary Amino Acid unit is a unit of formula VIII wherein $R^{20}$ is benzyl, $R^{21}$ is benzyl, and $R^{22}$ is —$(CH_2)_4NH_2$.

Useful -$W_w$- units can be designed and optimized in their selectivity for enzymatic cleavage by a particular enzyme, for example, a tumor-associated protease. In one embodiment, a -$W_w$- unit is that whose cleavage is catalyzed by cathepsin B, C and D, or a plasmin protease.

In one embodiment, -$W_w$- is a dipeptide, tripeptide, tetrapeptide or pentapeptide. When $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral.

Each carbon atom to which $R^{19}$, $R^{20}$, $R^{21}$, $R^{22}$ or $R^{23}$ is attached is independently in the (S) or (R) configuration.

In one aspect of the Amino Acid unit, the Amino Acid unit is valine-citrulline (vc or val-cit). In another aspect, the Amino Acid unit is phenylalanine-lysine (i.e., fk). In yet another aspect of the Amino Acid unit, the Amino Acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isopecotic acid lysine, beta-alanine lysine, glycine serine valine glutamine and isonepecotic acid.

VIII.) The Spacer Unit

The Spacer unit (-Y-), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the Antibody unit when both the Amino Acid unit and Stretcher unit are absent.

Spacer units are of two general types: non self-immolative or self-immolative. A non self-immolative Spacer unit is one in which part or all of the Spacer unit remains bound to the Drug moiety after cleavage, particularly enzymatic, of an Amino Acid unit from the antibody-drug conjugate. Examples of a non self-immolative Spacer unit include, but are not limited to a (glycine-glycine) Spacer unit and a glycine Spacer unit (both depicted in Scheme 1) (infra). When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Drug moiety or a glycine-Drug moiety is cleaved from L-Aa-Ww-. In one embodiment, an independent hydrolysis reaction takes place within the target cell, cleaving the glycine-Drug moiety bond and liberating the Drug.

Scheme 1

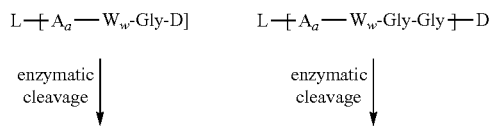

In some embodiments, a non self-immolative Spacer unit (-Y-) is -Gly-. In some embodiments, a non self-immolative Spacer unit (-Y-) is -Gly-Gly-.

In one embodiment, a Drug-Linker conjugate is provided in which the Spacer unit is absent (y=0), or a pharmaceutically acceptable salt or solvate thereof.

Alternatively, a conjugate containing a self-immolative Spacer unit can release -D. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, -$Y_y$- is a p-aminobenzyl alcohol (PAB) unit (see Schemes 2 and 3) whose phenylene portion is substituted with $Q_m$ wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

In some embodiments, -Y- is a PAB group that is linked to -$W_w$- via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to -D via a carbamate or carbonate group as described by Toki et al., 2002, *J. Org. Chem.* 67:1866-1872.

Scheme 2

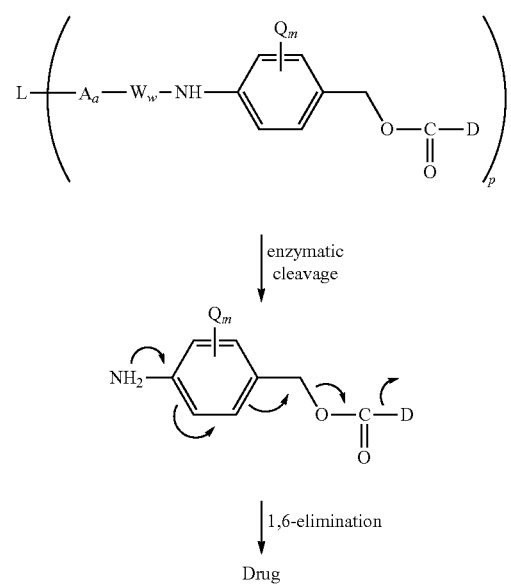

In Scheme 2, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 12. The alkyl, alkenyl and alkynyl groups, whether alone or as part of another group, can be optionally substituted.

Without being bound by any particular theory or mechanism, Scheme 3 depicts a possible mechanism of Drug release of a PAB group which is attached directly to -D via an ether or amine linkage, wherein D includes the oxygen or nitrogen group that is part of the Drug unit.

Scheme 3

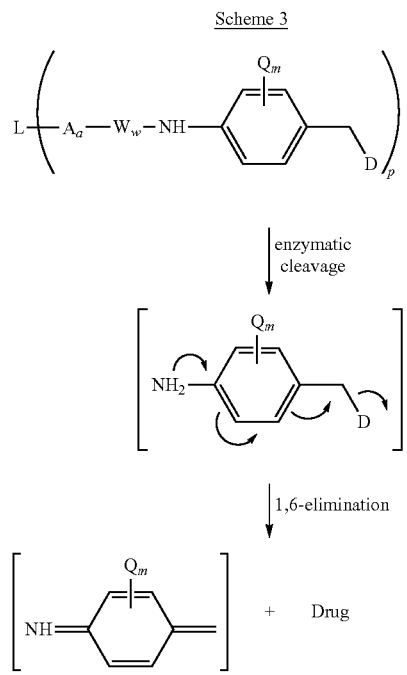

In Scheme 3, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 12. The alkyl, alkenyl and alkynyl groups, whether alone or as part of another group, can be optionally substituted.

Other examples of self-immolative spacers include, but are not limited to, aromatic compounds that are electronically similar to the PAB group such as 2-aminoimidazol-5-methanol derivatives (Hay, et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues, et al., 1995, *Chemistry Biology* 2:223), appropriately substituted bicyclo[2.2.1] and bicyclo[2.2.2] ring systems (Storm, et al., 1972, *J. Amer. Chem. Soc.* 94:5815) and 2-aminophenylpropionic acid amides (Amsberry, et al., 1990, *J. Org. Chem.* 55:5867). Elimination of amine-containing drugs that are substituted at the α-position of glycine (Kingsbury et al., 1984, *J. Med. Chem.* 27:1447) are also examples of self-immolative spacers.

In one embodiment, the Spacer unit is a branched bis (hydroxymethyl)-styrene (BHMS) unit as depicted in Scheme 4, which can be used to incorporate and release multiple drugs.

Scheme 4

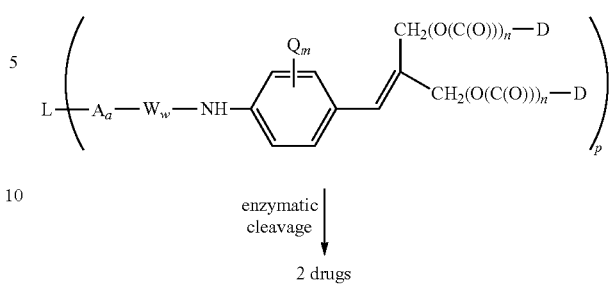

In Scheme 4, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; n is 0 or 1; and p ranges raging from 1 to about 12. The alkyl, alkenyl and alkynyl groups, whether alone or as part of another group, can be optionally substituted.

In some embodiments, the -D moieties are the same. In yet another embodiment, the -D moieties are different.

In one aspect, Spacer units (—$Y_y$—) are represented by Formulas (X)-(XII):

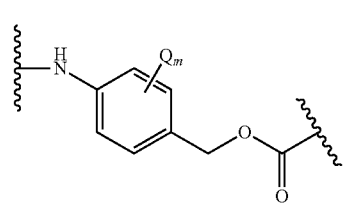

X wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

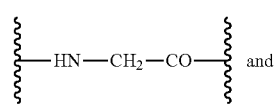

XI

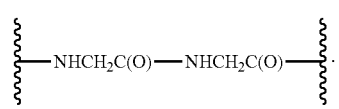

XII

Embodiments of the Formula I and II comprising antibody-drug conjugate compounds can include:

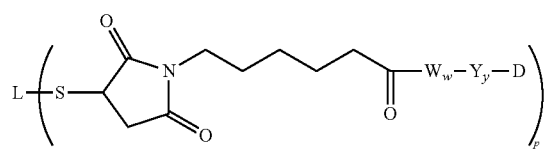

wherein w and y are each 0, 1 or 2, and,

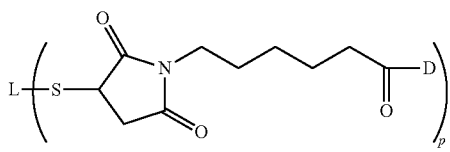

wherein w and y are each 0,

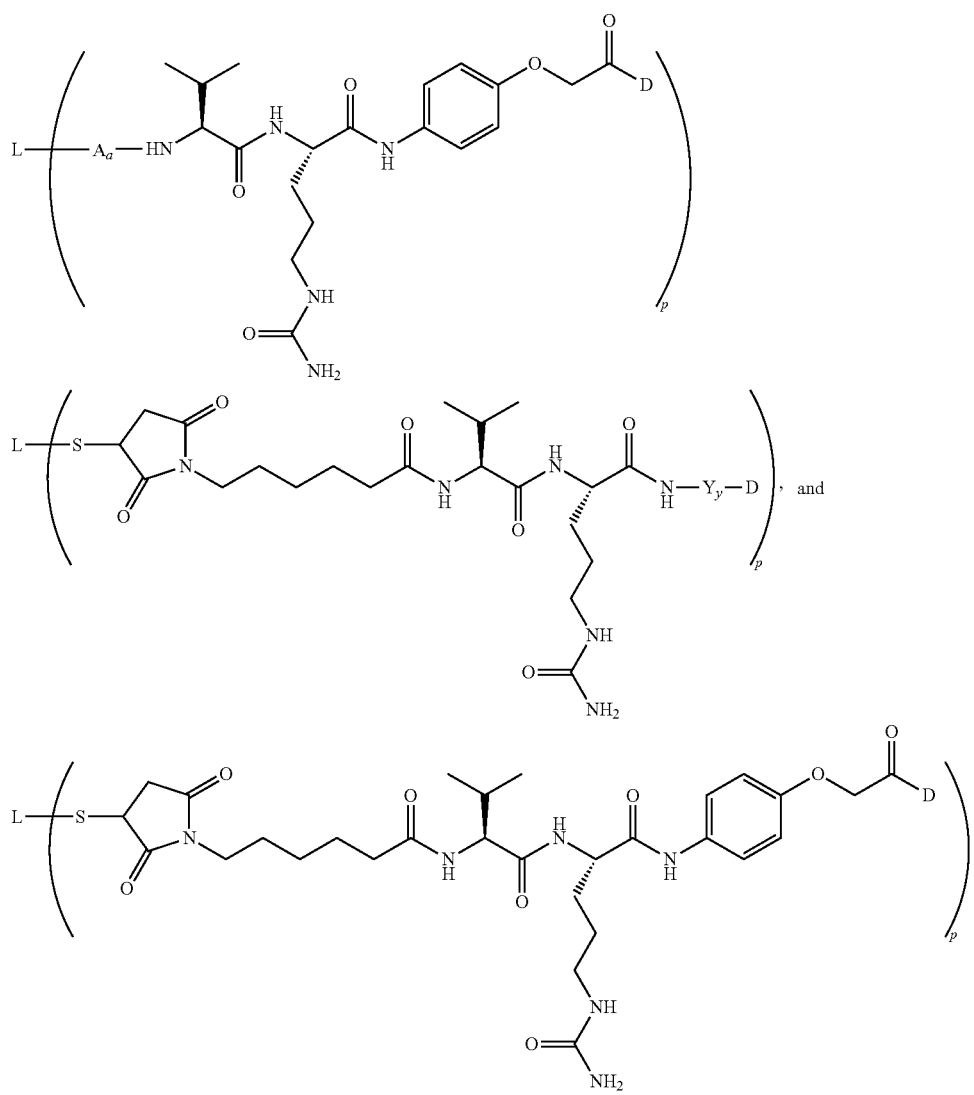

and

IX.) The Drug Unit

The Drug moiety (D) can be any cytotoxic, cytostatic or immunomodulatory (e.g., immunosuppressive) or drug. D is a Drug unit (moiety) having an atom that can form a bond with the Spacer unit, with the Amino Acid unit, with the Stretcher unit or with the Antibody unit. In some embodiments, the Drug unit D has a nitrogen atom that can form a bond with the Spacer unit. As used herein, the terms "drug unit" and "drug moiety" are synonymous and used interchangeably.

Useful classes of cytotoxic or immunomodulatory agents include, for example, antitubulin agents, DNA minor groove binders, DNA replication inhibitors, and alkylating agents.

In some embodiments, the Drug is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of exemplary auristatins are described in U.S. Patent Application Publication Nos. 2003-0083263, 2005-0238649 and 2005-0009751; International Patent Publication No. WO04/010957, International Patent Publication No. WO02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety and for all purposes.

Auristatins have been shown to interfere with microtubule dynamics and nuclear and cellular division and have anticancer activity. MMAF bind tubulin and can exert a cytotoxic or cytostatic effect on a 161P2F10B-expressing cell. There are a number of different assays, known in the art, which can be used for determining whether an auristatin or resultant antibody-drug conjugate exerts a cytostatic or cytotoxic effect on a desired cell line.

Methods for determining whether a compound binds tubulin are known in the art. See, for example, Muller, et al., *Anal. Chem* 2006, 78, 4390-4397; Hamel, et al., *Molecular Pharmacology*, 1995 47: 965-976; and Hamel, et al., *The Journal of Biological Chemistry*, 1990 265:28, 17141-17149. For purposes of the present invention, the relative affinity of a compound to tubulin can be determined Some preferred auristatins of the present invention bind tubulin with an affinity ranging from 10 fold lower (weaker affinity) than the binding affinity of MMAE to tubulin to 10 fold, 20 fold or even 100 fold higher (higher affinity) than the binding affinity of MMAE to tublin.

In some embodiments, -D is an auristatin of the formula $D_E$ or $D_F$:

(carbocycle), -aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

each $R^8$ is independently —H, —OH, —$C_1$-$C_{20}$ alkyl, —$C_2$-$C_{20}$ alkenyl, —$C_2$-$C_{20}$ alkynyl, —O—($C_1$-$C_{20}$ alkyl), —O—($C_2$-$C_{20}$ alkenyl), —O—($C_1$-$C_{20}$ alkynyl), or -carbocycle;

$R^9$ is —H, —$C_1$-$C_{20}$ alkyl, —$C_2$-$C_{20}$ alkenyl, or —$C_2$-$C_{20}$ alkynyl;

$R^{24}$ is -aryl, -heterocycle, or -carbocycle;

$R^{25}$ is —H, $C_1$-$C_{20}$ alkyl, —$C_2$-$C_{20}$ alkenyl, —$C_2$-$C_{20}$ alkynyl, -carbocycle, —O—($C_1$-$C_{20}$ alkyl), —O—($C_2$-$C_{20}$ alkenyl), —O—($C_2$-$C_{20}$ alkynyl), or $OR^{18}$ wherein $R^{18}$ is —H, a hydroxyl protecting group, or a direct bond where $OR^{18}$ represents =O;

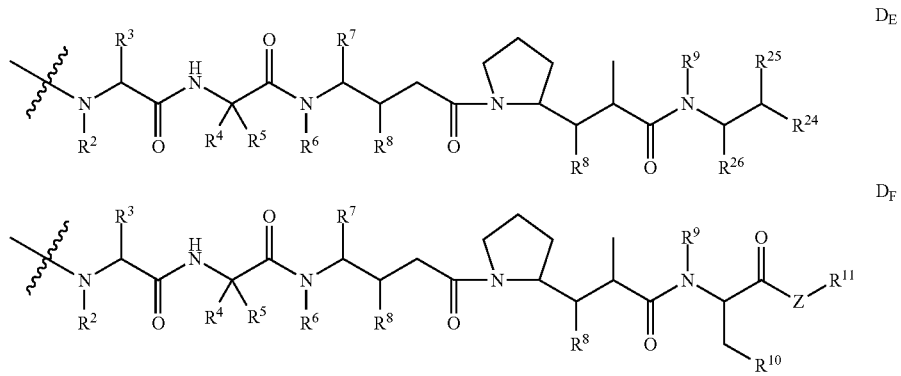

or a pharmaceutically acceptable salt or solvate form thereof;

wherein, independently at each location:

the wavy line indicates a bond;

$R^2$ is —$C_1$-$C_{20}$ alkyl, —$C_2$-$C_{20}$ alkenyl, or —$C_2$-$C_{20}$ alkynyl;

$R^3$ is —H, —$C_1$-$C_{20}$ alkyl, —$C_2$-$C_{20}$ alkenyl, —$C_2$-$C_{20}$ alkynyl, -carbocycle, —$C_1$-$C_{20}$ alkylene (carbocycle), —$C_2$-$C_{20}$ alkenylene(carbocycle), —$C_2$-$C_{20}$ alkynylene (carbocycle), -aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^4$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alyklene (carbocycle), —$C_2$-$C_{20}$ alkenylene(carbocycle), —$C_2$-$C_{20}$ alkynylene (carbocycle), aryl, —$C_1$-$C_{20}$ alkylene(aryl), —$C_2$-$C_{20}$ alkenylene(aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^5$ is —H or —$C_1$-$C_8$ alkyl;

or $R^4$ and $R^5$ jointly form a carbocyclic ring and have the formula —$(CR^aR^b)_s$— wherein $R^a$ and $R^b$ are independently —H, —$C_1$-$C_{20}$ alkyl, —$C_2$-$C_{20}$ alkenyl, —$C_2$-$C_{20}$ alkynyl, or -carbocycle and s is 2, 3, 4, 5 or 6, $R^6$ is —H, —$C_1$-$C_{20}$ alkyl, —$C_2$-$C_{20}$ alkenyl, or —$C_2$-$C_{20}$ alkynyl;

$R^7$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene $R^{26}$ is —H, —$C_1$-$C_{20}$ alkyl, —$C_2$-$C_{20}$ alkenyl, or -$C_2$-$C_{20}$ alkynyl, -aryl, -heterocycle, or -carbocycle;

$R^{10}$ is -aryl or -heterocycle;

Z is —O—, —S—, —NH—, or —$NR^{12}$, wherein $R^{12}$ is —$C_1$-$C_{20}$ alkyl, —$C_2$-$C_{20}$ alkenyl, or —$C_2$-$C_{20}$ alkynyl;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$;

m is an integer ranging from 1-1000;

$R^{13}$ is —$C_2$-$C_{20}$ alkylene, -$C_2$-$C_{20}$ alkenylene, or —$C_2$-$C_{20}$ alkynylene;

$R^{14}$ is —H, —$C_1$-$C_{20}$ alkyl, —$C_2$-$C_{20}$ alkenyl, or —$C_2$-$C_{20}$ alkynyl;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH; and n is an integer ranging from 0 to 6;

wherein said alkyl, alkenyl, alkynyl, alkylene, alkenylene, alkynyklene, aryl, carbocyle, and heterocycle radicals, whether alone or as part of another group, are optionally substituted.

Auristatins of the formula $D_E$ include those wherein said alkyl, alkenyl, alkynyl, alkylene, alkenylene, alkynyklene, aryl, carbocyle, and heterocycle radicals are unsubstituted.

Auristatins of the formula $D_E$ include those wherein the groups of $R^2$, $R^3$, $R^4$, $R^5$, $R^6$, $R^7$, $R^8$, and $R^9$ are unsubstituted and the groups of $R^{19}$, $R^{20}$ and $R^{21}$ are optionally substituted as described herein.

Auristatins of the formula $D_E$ include those wherein $R^2$ is $C_1$-$C_8$ alkyl;

$R^3$, $R^4$ and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene (monocyclic $C_3$-$C_6$ carbocycle), —$C_2$-$C_{20}$ alkynylene (monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene (heterocycle), or —$C_2$-$C_{20}$ alkynylene(heterocycle); wherein said alkyl, alkenyl, alkynyl, alkylene, alkenylene, alkynylene, carbocycle, aryl and heterocycle radicals are optionally substituted;

$R^5$ is —H;

$R^6$ is —$C_1$-$C_8$ alkyl;

each $R^8$ is independently selected from —OH, —O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted;

$R^9$ is —H or —$C_1$-$C_8$ alkyl;

$R^{24}$ is optionally substituted -phenyl;

$R^{25}$ is —$OR^{18}$; wherein $R^{18}$ is H, a hydroxyl protecting group, or a direct bond where $OR^{18}$ represents =O;

$R^{26}$ is selected from —H, —$C_1$-$C_{20}$ alkyl, —$C_2$-$C_{20}$ alkenyl, —$C_2$-$C_{20}$ alkynyl, or -carbocycle; wherein said alkyl, alkenyl, alkynyl and carbocycle radicals are optionally substituted; or a pharmaceutically acceptable salt or solvate form thereof.

Auristatins of the formula $D_E$ include those wherein $R^2$ is methyl;

$R^3$ is —H, —$C_1$-$C_8$ alkyl, —$C_2$-$C_8$ alkenyl, or $C_2$-$C_8$ alkynyl, wherein said alkyl, alkenyl and alkynyl radicals are optionally substituted;

$R^4$ is —H, —$C_1$-$C_8$ alkyl, —$C_2$-$C_8$ alkenyl, —$C_2$-$C_8$ alkynyl, monocyclic $C_3$-$C_6$ carbocycle, —$C_6$-$C_{10}$ aryl, —$C_1$-$C_8$ alkylene($C_6$-$C_{10}$ aryl), —$C_2$-$C_8$ alkenylene ($C_6$-$C_{10}$ aryl), —$C_2$-$C_8$ alkynylene($C_6$-$C_{10}$ aryl), —$C_1$-$C_8$ alkylene (monocyclic $C_3$-$C_6$ carbocycle), —$C_2$-$C_8$ alkenylene (monocyclic $C_3$-$C_6$ carbocycle), —$C_2$-$C_8$ alkynylene(monocyclic $C_3$-$C_6$ carbocycle); wherein said alkyl, alkenyl, alkynyl, alkylene, alkenylene, alkynylene, aryl and carbocycle radicals whether alone or as part of another group are optionally substituted;

$R^5$ is —H;

$R^6$ is methyl;

$R^7$ is —$C_1$-$C_8$ alkyl, —$C_2$-$C_8$ alkenyl or —$C_2$-$C_8$ alkynyl;

each $R^8$ is methoxy;

$R^9$ is —H or —$C_1$-$C_8$ alkyl;

$R^{24}$ is -phenyl;

$R^{25}$ is —$OR^{18}$; wherein $R^{18}$ is H, a hydroxyl protecting group, or a direct bond where $OR^{18}$ represents =O;

$R^{26}$ is methyl;

or a pharmaceutically acceptable salt form thereof.

Auristatins of the formula $D_E$ include those wherein:

$R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ is isopropyl or sec-butyl; $R^8$ is methoxy; $R^9$ is —H or —$C_1$-$C_8$ alkyl; $R^{24}$ is phenyl; $R^{25}$ is —$OR^{18}$; wherein $R^{18}$ is —H, a hydroxyl protecting group, or a direct bond where $OR^{18}$ represents =O; and $R^{26}$ is methyl; or a pharmaceutically acceptable salt or solvate form thereof.

Auristatins of the formula $D_E$ include those wherein:

$R^2$ is methyl or $C_1$-$C_3$ alkyl, $R^3$ is —H or —$C_1$-$C_3$ alkyl;

$R^4$ is —$C_1$-$C_5$ alkyl;

$R^5$ is H;

$R^6$ is C1-C3 alkyl;

$R^7$ is —$C_1$-$C_5$ alkyl;

$R^8$ is —$C_1$-$C_3$ alkoxy;

$R^9$ is —H or —$C_1$-$C_8$ alkyl;

$R^{24}$ is phenyl;

$R^{25}$ is —$OR^{18}$; wherein $R^{18}$ is —H, a hydroxyl protecting group, or a direct bond where $OR^{18}$ represents =O; and $R^{26}$ is —$C_1$-$C_3$ alkyl;

or a pharmaceutically acceptable salt form thereof.

Auristatins of the formula $D_F$ include those wherein $R^2$ is methyl;

$R^3$, $R^4$, and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene (monocyclic $C_3$-$C_6$ carbocycle), —$C_2$-$C_{20}$ alkynylene (monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene (heterocycle), or —$C_2$-$C_{20}$ alkynylene(heterocycle); wherein said alkyl, alkenyl, alkynyl, alkylene, alkenylene, alkynylene, carbocycle, aryl and heterocycle radicals whether alone or as part of another group are optionally substituted;

$R^5$ is —H;

$R^6$ is methyl;

each $R^8$ is methoxy;

$R^9$ is —H, —$C_1$-$C_{20}$ alkyl, —$C_2$-$C_{20}$ alkenyl, or —$C_2$-$C_{20}$ alkynyl; wherein said alkyl, alkenyl and alkynyl radical are optionally substituted;

$R^{10}$ is optionally substituted aryl or optionally substituted heterocycle;

Z is —O—, —S—, —NH—, or —$NR^{12}$, wherein $R^{12}$ is —$C_1$-$C_{20}$ alkyl, —$C_2$-$C_{20}$ alkenyl, or —$C_2$-$C_{20}$ alkynyl, each of which is optionally substituted;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$, wherein said alkyl, alkenyl, alkynyl, aryl and heterocycle radicals are optionally substituted;

m is an integer ranging from 1-1000 or m=0;

$R^{13}$ is —$C_2$-$C_{20}$ alkylene, —$C_2$-$C_{20}$ alkenylene, or —$C_2$-$C_{20}$ alkynylene, each of which is optionally substituted;

$R^{14}$ is —H, —$C_1$-$C_{20}$ alkyl, —$C_2$-$C_{20}$ alkenyl, or —$C_2$-$C_{20}$ alkynyl wherein said alkyl, alkenyl and alkynyl radicals are optionally substituted;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl wherein said alkyl, alkenyl and alkynyl radicals are optionally substituted;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH wherein said alkyl, alkenyl and alkynyl radicals are optionally substituted;

n is an integer ranging from 0 to 6;

or a pharmaceutically acceptable salt thereof.

In certain of these embodiments, $R^{10}$ is optionally substituted phenyl.

Auristatins of the formula $D_F$ include those wherein the groups of $R^2$, $R^3$, $R^4$, $R^5$, $R^6$, $R^7$, $R^8$, and $R^9$ are unsubstituted and the groups of $R^{10}$ and $R^{11}$ are as described herein.

Auristatins of the formula $D_F$ include those wherein said alkyl, alkenyl, alkynyl, alkylene, alkenylene, alkynyklene, aryl, carbocyle, and heterocycle radicals are unsubstituted.

Auristatins of the formula $D_F$ include those wherein $R^2$ is —$C_1$-$C_3$ alkyl; $R^3$ is —H or —$C_1$-$C_3$ alkyl; $R^4$ is —$C_1$-$C_5$ alkyl; $R^5$ is —H; $R^6$ is —$C_1$-$C_3$ alkyl; $R^7$ is —$C_1$-$C_5$ alkyl; $R^8$ is —$C_1$-$C_3$ alkoxy; $R^9$ is —H or —$C_1$-$C_8$ alkyl; $R^{10}$ is optionally substituted phenyl; Z is —O—, —S—, or —NH—; $R^{11}$ is as defined herein; or a pharmaceutically acceptable salt thereof.

Auristatins of the formula $D_F$ include those wherein $R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ is isopropyl or sec-butyl; $R^8$ is methoxy; $R^9$ is —H or —$C_1$-$C_8$ alkyl; $R^{10}$ is optionally substituted phenyl; Z is —O—, —S—, or —NH—; and $R^{11}$ is as defined herein; or a pharmaceutically acceptable salt thereof.

Auristatins of the formula $D_F$ include those wherein $R^2$ is methyl; $R^3$ is —H or —$C_1$-$C_3$ alkyl; $R^4$ is —$C_1$-$C_5$ alkyl; $R^5$ is —H; $R^6$ is methyl; $R^7$ isopropyl or sec-butyl; $R^8$ is methoxy; $R^9$ is —H or $C_1$-$C_8$ alkyl; $R^{10}$ is phenyl; and Z is —O— or —NH— and $R^{11}$ is as defined herein, preferably hydrogen; or a pharmaceutically acceptable salt form thereof.

Auristatins of the formula $D_F$ include those wherein $R^2$ is —$C_1$-$C_3$ alkyl; $R^3$ is —H or —$C_1$-$C_3$ alkyl; $R^4$ is —$C_1$-$C_5$ alkyl; $R^5$ is —H; $R^6$ is —$C_1$-$C_3$ alkyl; $R^7$ is —$C_1$-$C_5$ alkyl; $R^8$ is —$C_1$-$C_3$ alkoxy; $R^9$ is —H or —$C_1$-$C_8$ alkyl; $R^{10}$ is phenyl; and Z is —O— or —NH— and $R^{11}$ is as defined herein, preferably hydrogen; or a pharmaceutically acceptable salt form thereof.

Auristatins of the formula $D_E$ or $D_F$ include those wherein $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl. The remainder of the substituents are as defined herein.

Auristatins of the formula $D_E$ or $D_F$ include those wherein $R^2$ and $R^6$ are each methyl, and $R^9$ is H. The remainder of the substituents are as defined herein.

Auristatins of the formula $D_E$ or $D_F$ include those wherein each occurrence of $R^8$ is —$OCH_3$. The remainder of the substituents are as defined herein.

Auristatins of the formula $D_E$ or $D_F$ include those wherein $R^3$ and $R^4$ are each isopropyl, $R^2$ and $R^6$ are each methyl, $R^5$ is H, $R^7$ is sec-butyl, each occurrence of $R^8$ is —$OCH_3$, and $R^9$ is H. The remainder of the substituents are as defined herein.

Auristatins of the formula $D_F$ include those wherein Z is —O— or —NH—. The remainder of the substituents are as defined herein.

Auristatins of the formula $D_F$ include those wherein $R^{10}$ is aryl. The remainder of the substituents are as defined herein.

Auristatins of the formula $D_F$ include those wherein $R^{10}$ is -phenyl. The remainder of the substituents are as defined herein.

Auristatins of the formula $D_F$ include those wherein Z is —O—, and $R^{11}$ is H, methyl or t-butyl. The remainder of the substituents are as defined herein.

Auristatins of the formula $D_F$ include those wherein, when Z is —NH—, $R^{11}$ is —$(O)_m$—$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH. The remainder of the substituents are as defined herein.

Auristatins of the formula $D_F$ include those wherein when Z is —NH—, $R^{11}$ is —$(R^{13}O)_m$—$CH(R^{15})_2$, wherein $R^{15}$ is —$(CH_2)_n$—$SO_3H$. The remainder of the substituents are as defined herein.

In preferred embodiments, when D is an auristatin of formula $D_E$, w is an integer ranging from 1 to 12, preferably 2 to 12, y is 1 or 2, and a is preferably 1.

In some embodiments, wherein D is an auristatin of formula $D_F$, a is 1 and w and y are 0.

Illustrative Drug units (-D) include the drug units having the following structures:

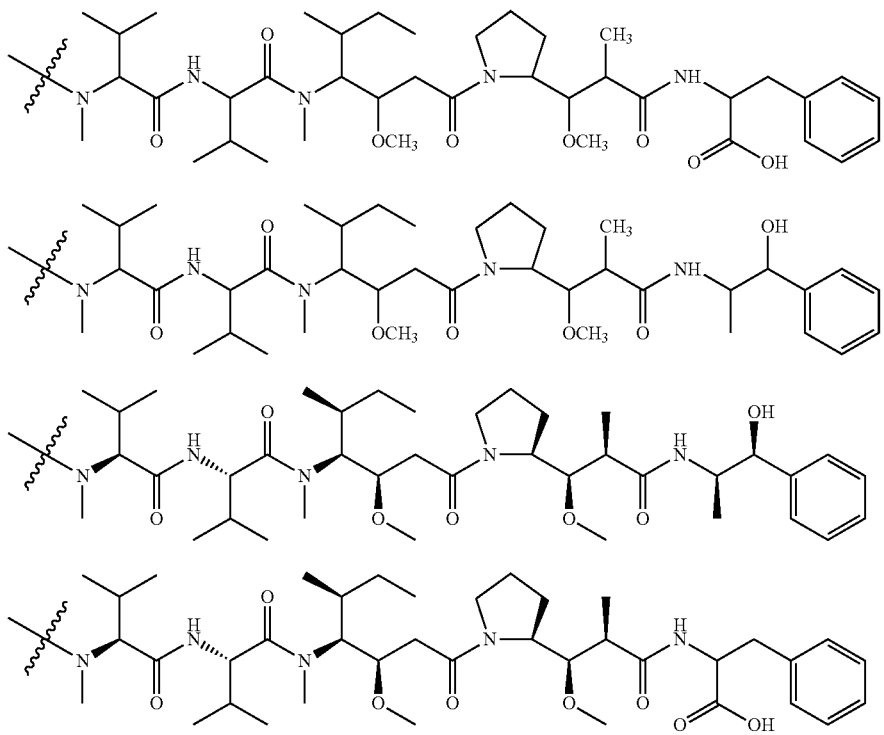

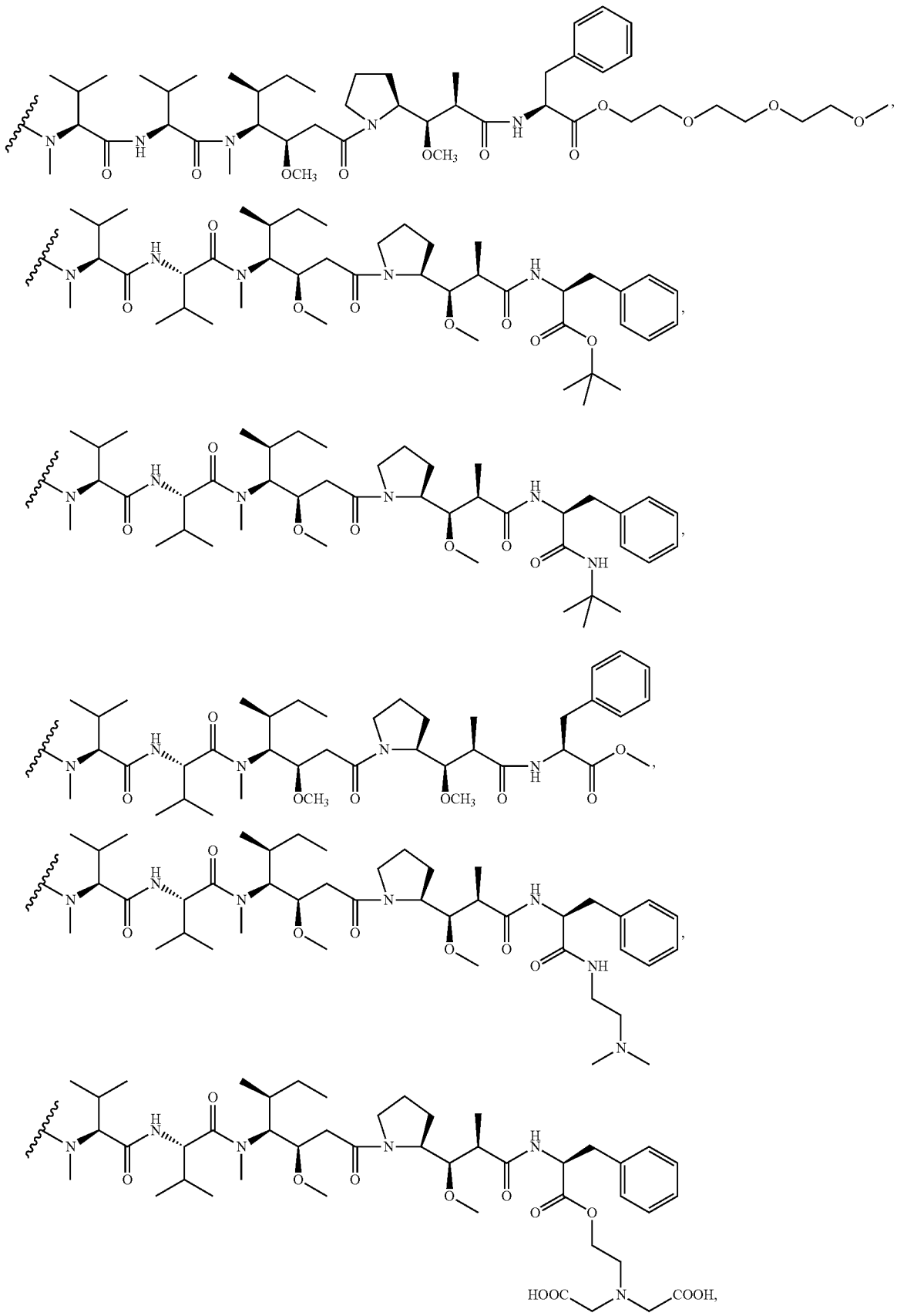

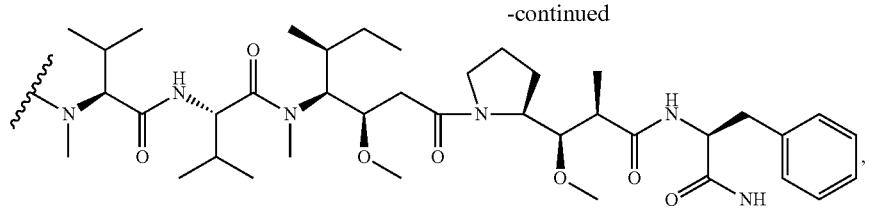

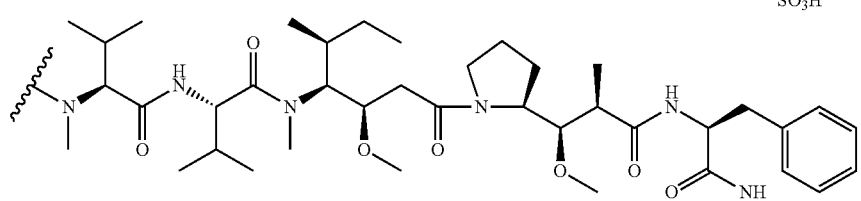

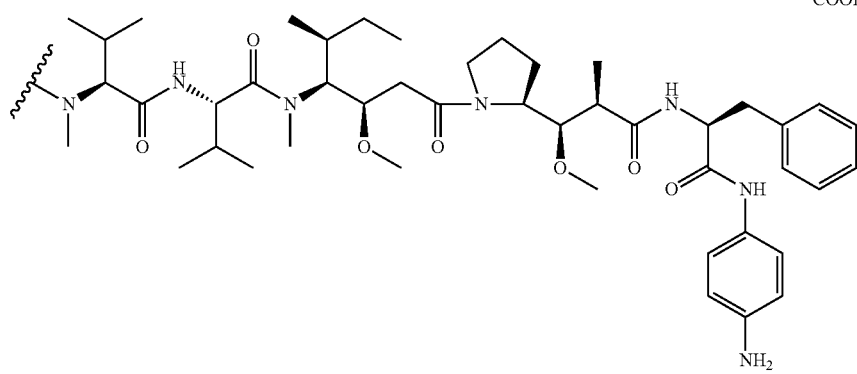

or pharmaceutically acceptable salts or solvates thereof.

In one aspect, hydrophilic groups, such as but not limited to triethylene glycol esters (TEG) can be attached to the Drug Unit at $R^{11}$. Without being bound by theory, the hydrophilic groups assist in the internalization and non-agglomeration of the Drug Unit.

In some embodiments, the Drug unit is not TZT-1027. In some embodiments, the Drug unit is not auristatin E, dolastatin 10, or auristatin PE.

In preferred embodiment, antibody-drug conjugate compounds have the following structures wherein "L" or "mAb-s-" represents a 161P2F10B MAb designated H16-7.8 set forth herein:

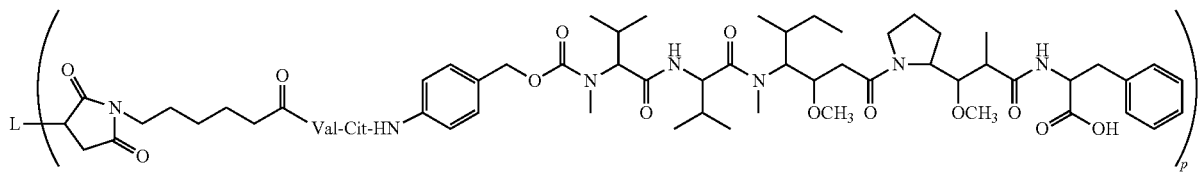

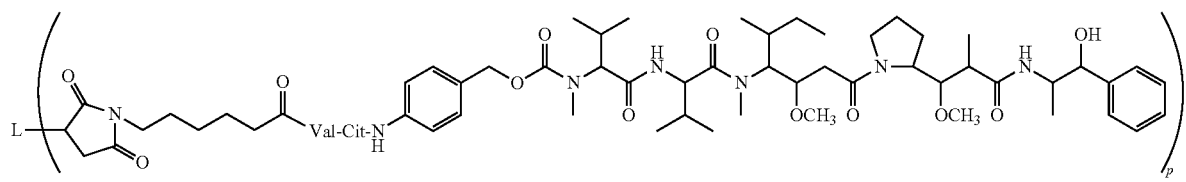

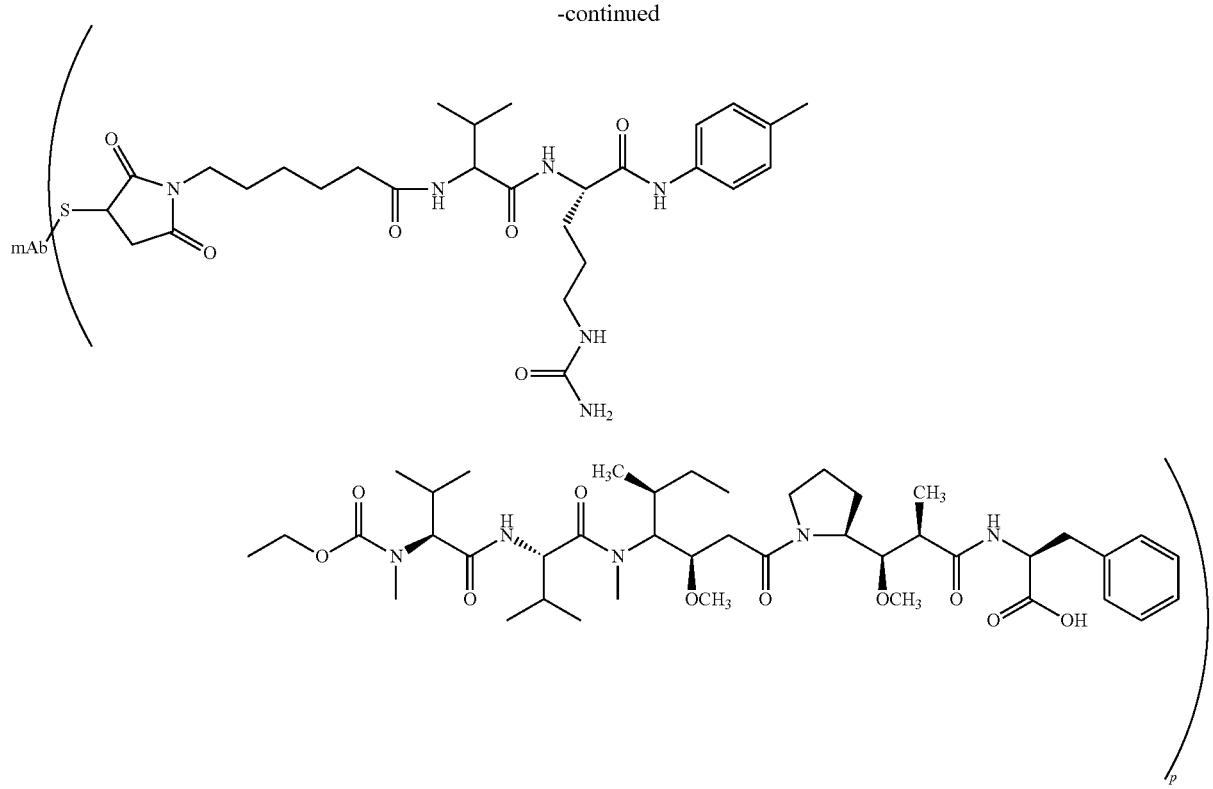

L-MC-vc-PAB-MMAF
or
Error! Objects cannot be created from editing field codes.
L-MC-vc-PAB-MMAE
or

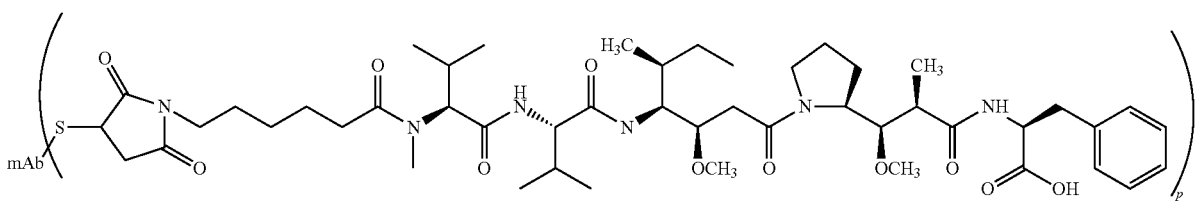

L-MC-MMAF
or pharmaceutically acceptable salt thereof.

In some embodiments, the Drug Unit is a calicheamicin, camptothecin, a maytansinoid, or an anthracycline. In some embodiments the drug is a taxane, a topoisomerase inhibitor, a vinca alkaloid, or the like.

In some typical embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, and vinca alkaloids. Other cytotoxic agents include, for example, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the Drug is an anti-tubulin agent. Examples of anti-tubulin agents include, auristatins, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131).

In certain embodiments, the cytotoxic or cytostatic agent is a dolastatin. In certain embodiments, the cytotoxic or cytostatic agent is of the auristatin class. Thus, in a specific embodiment, the cytotoxic or cytostatic agent is MMAE (Formula XI). In another specific embodiment, the cytotoxic or cytostatic agent is AFP (Formula XVI).

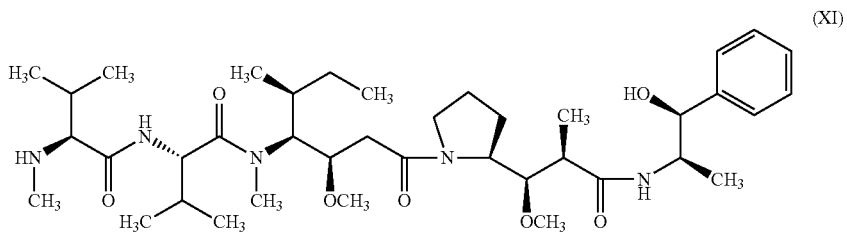 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]
(XI)
In certain embodiments, the cytotoxic or cytostatic agent is a compound of formulas XII-XXI or pharmaceutically acceptable salt thereof:
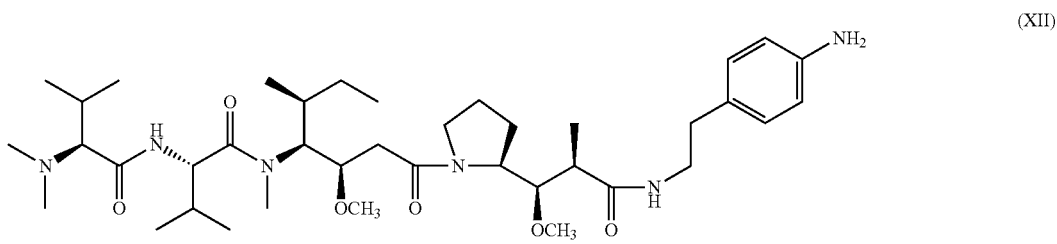
(XII)
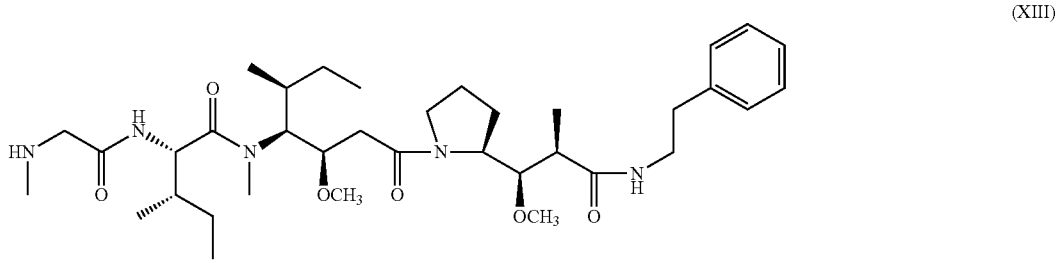
(XIII)
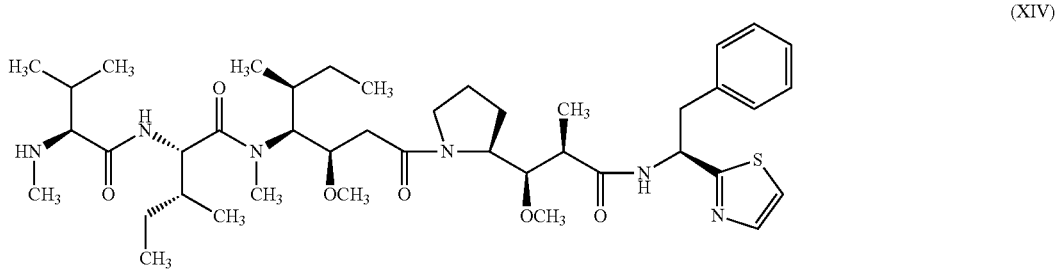
(XIV)
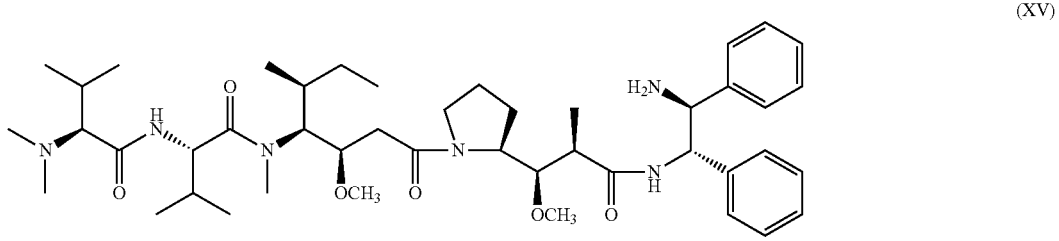
(XV)
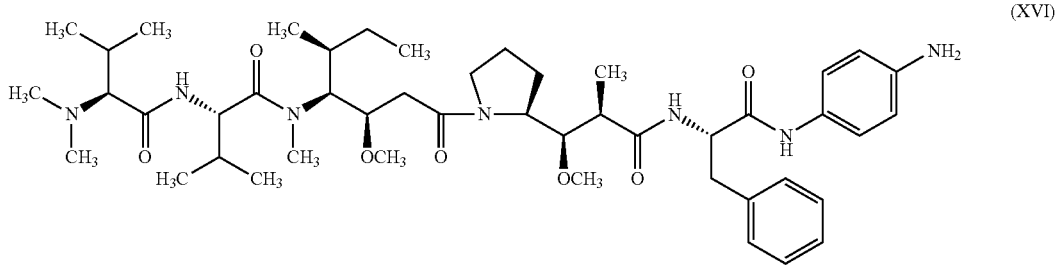
(XVI)

(XVII)
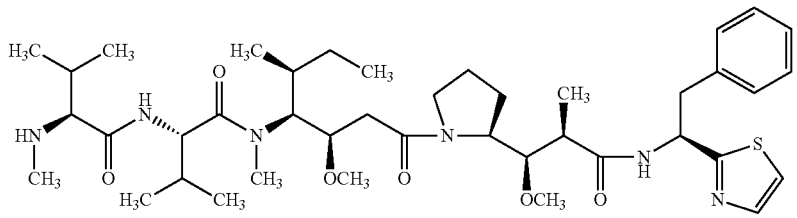
(XVIII)
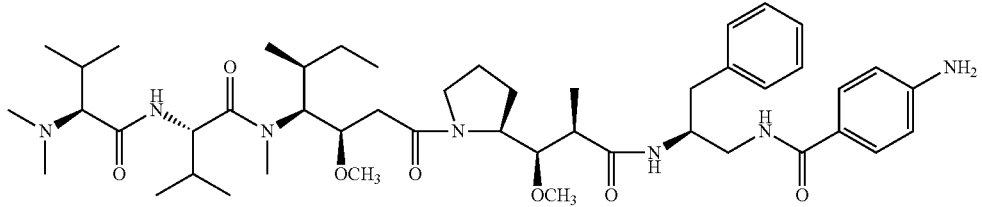
(XVIV)
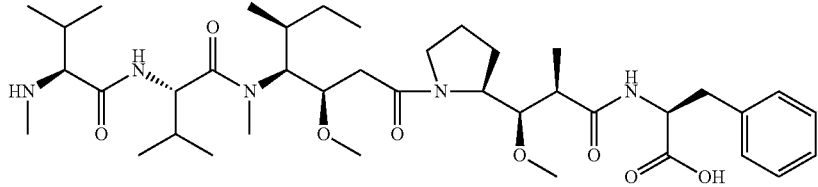
(XX)
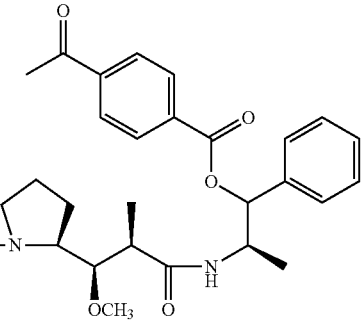
(XXI)
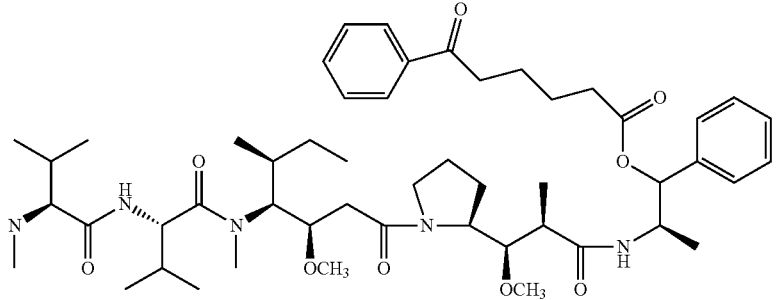
p is 1 to 12. In more preferred embodiment, antibody-drug conjugate compounds have the following structures wherein "mAb-s-" represents an 161P2F10B MAb designated H16-7.8 set forth herein, and p is 4:
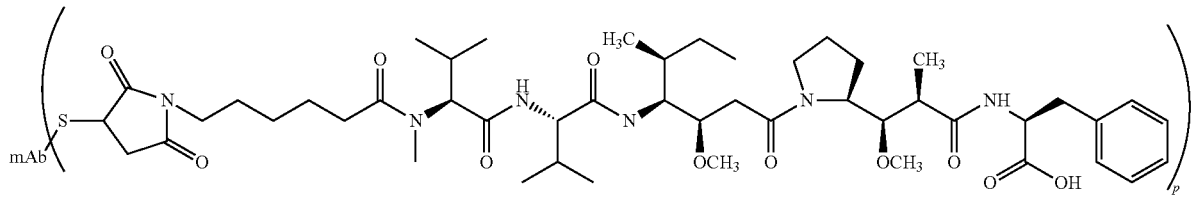

In a specific embodiment, the cytotoxic or cytostatic agent is MMAF (Formula XVIV).

X.) Drug Loading

Drug loading is represented by p and is the average number of drug moieties per antibody in a molecule. Drug loading may range from 1 to 20 drug moieties (D) per antibody. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay. The quantitative distribution of ADC in terms of p may also be determined In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g., p>5, may cause aggregation, insolubility, toxicity, or loss of cellular permeability of certain antibody-drug conjugates. In certain embodiments, the drug loading for an ADC of the invention ranges from 1 to about 12; from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g., hydrophobic interaction chromatography (see, e.g., Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, *Proceedings of the AACR*, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, *Proceedings of the AACR, Volume* 45, March 2004). In certain embodiments, a homogeneous ADC with a single loading value may be isolated from the conjugation mixture by electrophoresis or chromatography.

XI.) Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of a Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that a Antibody Drug conjugate is useful in the treatment of cancers.

Cell viability can be measured by determining in a cell the uptake of a dye such as neutral red, trypan blue, or ALAMAR™ blue (see, e.g., Page, et al., 1993, *Intl. J. Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity (Skehan, et al., 1990, *J. Natl. Cancer Inst.* 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, *J. Immunol. Methods* 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in *Biochemica*, 1999, No. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, *Current Protocols in Immunology* (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza, et al., 1995, *Cancer Research* 55:3110-16).

In vivo, the effect of a 161P2F10B therapeutic composition can be evaluated in a suitable animal model. For example, xenogenic cancer models can be used, wherein cancer explants or passaged xenograft tissues are introduced into immune compromised animals, such as nude or SCID mice (Klein, et al., 1997, *Nature Medicine* 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, *Remington's Pharmaceutical Sciences* 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XII.) Treatment of Cancer(s)

The identification of 161P2F10B as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

Expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensable, such as the prostate and ovary, can be removed without affecting mortality. Finally, some vital organs are not affected by normal organ expression because of an immunoprivilege Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a 161P2F10B protein are useful for patients suffering from a cancer that expresses 161P2F10B. These therapeutic approaches generally fall into three classes. The first class modulates 161P2F10B function as it relates to tumor cell growth leading to inhibition or retardation of tumor cell growth or inducing its killing. The second class comprises various methods for inhibiting the binding or association of a 161P2F10B protein with its binding partner or with other proteins. The third class comprises a variety of methods for inhibiting the transcription of a 161P2F10B gene or translation of 161P2F10B mRNA.

Accordingly, Cancer patients can be evaluated for the presence and level of 161P2F10B expression, preferably using immunohistochemical assessments of tumor tissue, quantitative 161P2F10B imaging, or other techniques that reliably indicate the presence and degree of 161P2F10B expression Immunohistochemical analysis of tumor biopsies or surgical specimens is preferred for this purpose. Methods for immunohistochemical analysis of tumor tissues are well known in the art.

XIII) 161P2F10B as a Target for Antibody-Based Therapy

161P2F10B is an attractive target for antibody-based therapeutic strategies. A number of antibody strategies are known in the art for targeting both extracellular and intracellular molecules (see, e.g., complement and ADCC mediated killing as well as the use of intrabodies). Because 161P2F10B is expressed by cancer cells of various lineages relative to corresponding normal cells, systemic administration of 161P2F10B-immunoreactive compositions are prepared that exhibit excellent sensitivity without toxic, non-specific and/ or non-target effects caused by binding of the immunoreactive composition to non-target organs and tissues. Antibodies specifically reactive with domains of 161P2F10B are useful to treat cancers (preferably cancer of Table I, more preferably kidney and/or liver cancer) systemically, preferably as antibody drug conjugates (i.e., ADCs) wherein the conjugate is with a toxin or therapeutic agent.

Those skilled in the art understand that antibodies can be used to specifically target and bind immunogenic molecules such as an immunogenic region of a 161P2F10B sequence shown in FIG. 1. In addition, skilled artisans understand that it is routine to conjugate antibodies to cytotoxic agents (see, e.g., Slevers, et al., *Blood* 93:11 3678-3684 (Jun. 1, 1999)). When cytotoxic and/or therapeutic agents are delivered directly to cells, such as by conjugating them to antibodies specific for a molecule expressed by that cell (e.g., 161P2F10B), the cytotoxic agent will exert its known biological effect (i.e., cytotoxicity) on those cells.

A wide variety of compositions and methods for using antibody-cytotoxic agent conjugates to kill cells are known in the art. In the context of cancers, typical methods entail administering to an mammal having a tumor a biologically effective amount of a conjugate comprising a selected cytotoxic and/or therapeutic agent linked to a targeting agent (e.g., a 161P2F10B MAb, preferably H16-7.8) that binds to an antigen (e.g., 161P2F10B) expressed, accessible to binding or localized on the cell surfaces. A typical embodiment is a method of delivering a cytotoxic and/or therapeutic agent to a cell expressing 161P2F10B, comprising conjugating the cytotoxic agent to an antibody that immunospecifically binds to a 161P2F10B epitope, and, exposing the cell to the antibody drug conjugate (ADC). Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using 161P2F10B antibodies can be done in accordance with various approaches that have been successfully employed in the treatment of other types of cancer, including but not limited to colon cancer (Arlen, et al., 1998, *Crit. Rev. Immunol.* 18:133-138), multiple myeloma (Ozaki, et al., 1997, *Blood* 90:3179-3186, Tsunenari, et al., 1997, *Blood* 90:2437-2444), gastric cancer (Kasprzyk, et al., 1992, *Cancer Res.* 52:2771-2776), B-cell lymphoma (Funakoshi, et al., 1996, *J. Immunother. Emphasis Tumor Immunol.* 19:93-101), leukemia (Zhong, et al., 1996, *Leuk. Res.* 20:581-589), colorectal cancer (Moun, et al., 1994, *Cancer Res.* 54:6160-6166; Velders, et al., 1995, *Cancer Res.* 55:4398-4403), and breast cancer (Shepard, et al., 1991, *J. Clin. Immunol.* 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™ Coulter Pharmaceuticals) respectively, while others involve co-administration of antibodies and other therapeutic agents, such as Herceptin™ (trastuzumab) with paclitaxel (Genentech, Inc.).

In a preferred embodiment, the antibodies will be conjugated a cytotoxic agent, supra, preferably an auristatin derivative designated MMAF (Seattle Genetics).

Preferred monoclonal antibodies used in the therapeutic methods of the invention are those that are either fully human and that bind specifically to the target 161P2F10B antigen with high affinity.

XIV.) 161P2F10B ADC Cocktails

Therapeutic methods of the invention contemplate the administration of single 161P2F10B ADCs as well as combinations, or cocktails, of different MAbs (i.e., 161P2F10B MAbs or Mabs that bind another protein). Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, 161P2F10B MAbs can be administered concomitantly with other therapeutic modalities, including but not limited to various chemotherapeutic and biologic agents, androgen-blockers, immune modulators (e.g., IL-2, GM-CSF), surgery or radiation. In a preferred embodiment, the 161P2F10B MAbs are administered in conjugated form.

161P2F10B ADC formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the 161P2F10B ADC preparation, via an acceptable route of administration such as intravenous injection (IV), typically at a dose in the range, including but not limited to, 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg MAb per week are effective and well tolerated.

Based on clinical experience with the Herceptin® (trastuzumab) in the treatment of metastatic breast cancer, an initial loading dose of approximately 4 mg/kg patient body weight IV, followed by weekly doses of about 2 mg/kg IV of the MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the MAbs used, the degree of 161P2F10B expression in the patient, the extent of circulating shed 161P2F10B antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 161P2F10B in a given sample (e.g., the levels of circulating 161P2F10B antigen and/or 161P2F10B expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

An object of the present invention is to provide 161P2F10B ADCs, which inhibit or retard the growth of tumor cells, preferably tumor cells of Table I. A further object of this invention is to provide methods to inhibit angiogenesis and other biological functions and thereby reduce tumor growth in mammals, preferably humans, using such 161P2F10B ADCs, and in particular using such 161P2F10B ADCs combined with other drugs or immunologically active treatments.

XV.) Combination Therapy

In one embodiment, there is synergy when tumors, including human tumors, are treated with 161P2F10B ADCs in conjunction with chemotherapeutic agents or radiation or combinations thereof. In other words, the inhibition of tumor growth by a 161P2F10B ADC is enhanced more than expected when combined with chemotherapeutic agents or radiation or combinations thereof. Synergy may be shown, for example, by greater inhibition of tumor growth with combined treatment than would be expected from a treatment of only 161P2F10B ADC or the additive effect of treatment with a 161P2F10B ADC and a chemotherapeutic agent or radiation. Preferably, synergy is demonstrated by remission of the cancer where remission is not expected from treatment either from a 161P2F10B ADC or with treatment using an additive combination of a 161P2F10B ADC and a chemotherapeutic agent or radiation.

The method for inhibiting growth of tumor cells using a 161P2F10B ADC and a combination of chemotherapy or radiation or both comprises administering the 161P2F10B ADC before, during, or after commencing chemotherapy or radiation therapy, as well as any combination thereof (i.e., before and during, before and after, during and after, or before, during, and after commencing the chemotherapy and/or radiation therapy). For example, the 161P2F10B ADC is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the 161P2F10B ADCs and the chemotherapeutic agent are administered as separate molecules. Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

The source of radiation, used in combination with a 161P2F10B ADC, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g., Anti-CTLA-4 antibodies as described in WO2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl) propionanilide may be used.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

XVI.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise an antibody that is or can be detectably labeled. Kits can comprise a container comprising a Drug Unit. The kit can include all or part of the amino acid sequences in FIG. 2, or FIG. 3 or analogs thereof, or a nucleic acid molecule that encodes such amino acid sequences.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer of a tissue set forth in Table I.

The terms "kit" and "article of manufacture" can be used as synonyms.

In another embodiment of the invention, an article(s) of manufacture containing compositions, such as antibody drug conjugates (ADCs), e.g., materials useful for the diagnosis, prognosis, prophylaxis and/or treatment of cancers of tissues such as those set forth in Table I is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In another embodiment a container also comprises an antibody, binding fragment thereof or specific binding protein for use in evaluating protein expression of 161P2F10B in cells and tissues, or for relevant laboratory, prognostic, diagnostic, prophylactic and therapeutic purposes; indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody drug conjugate specifically binding to 161P2F10B.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

The 161P2F10B Antigen

The 161P2F10B gene sequence was discovered using Suppression Subtractive Hybridization (SSH) methods known in the art. The 161P2F10B SSH sequence of 182 by was identified from cDNA derived from kidney cancer patients using standard methods. A full length cDNA clone for 161P2F10B was isolated from kidney cancer patient specimens. The cDNA is 3858 by in length and encodes a 875 amino acid ORF (See, FIG. 1). 161P2F10B showed homology to ENPP3 (See, Buhring, et. al., *Blood* 97:3303-3305 (2001). 161P2F10B maps to chromosome 6q22 using standard methods known in the art. For further reference see, U.S. Pat. No. 7,279,556 (Agensys, Inc., Santa Monica, Calif.), U.S. Pat. No. 7,405,290 (Agensys, Inc., Santa Monica, Calif.), U.S. Pat. No. 7,067,130 (Agensys, Inc., Santa Monica, Calif.), and U.S. Pat. No. 7,226,594 (Agensys, Inc., Santa Monica, Calif.).

Example 2

Generation of 161P2F10B Monoclonal Antibodies (MAbs)

In one embodiment, therapeutic Monoclonal Antibodies ("MAbs") to 161P2F10B comprise those that react with epitopes specific for protein that would bind, internalize, disrupt or modulate the biological function of 161P2F10B, for example, those that would disrupt the interaction with ligands, substrates, and binding partners Immunogens for generation of such MAbs include those designed to encode or contain the extracellular domains or the entire 161P2F10B protein sequence, and regions predicted to contain functional motifs predicted to be antigenic from computer analysis of the amino acid sequence Immunogens include peptides and recombinant proteins such as tag5-161P2F10B, a purified mammalian cell derived His tagged protein. In addition, cells engineered through retroviral transduction to express high levels of 161P2F10B, such as RAT1-161P2F10B, are used to immunize mice.

MAbs to 161P2F10B were generated using XenoMouse® technology (Amgen Fremont) wherein the murine heavy and kappa light chain loci have been inactivated and a majority of the human heavy and kappa light chain immunoglobulin loci have been inserted. The MAb designated H16-7.8 was generated from immunization with human γ2 producing XenoMice with TagS-161P2F10B cells.

The 161P2F10B MAb H16-7.8 specifically binds to recombinant 161P2F10B (SEQ ID NO:2) expressing cells and endogenous cell surface 161P2F10B expressed in cancer xenograft cells.

DNA coding sequences for 161P2F10B MAb H16-7.8 were determined after isolating mRNA from the respective hybridoma cells with TRIzol® reagent (Life Technologies, Gibco BRL).

Anti-161P2F10B H16-7.8 heavy and light chain variable nucleic acid sequences were sequenced from the hybridoma cells using the following protocol. H16-7.8 secreting hybridoma cells were lysed with TRIzol® reagent (Life Technologies, Gibco BRL). Total RNA was purified and quantified. First strand cDNAs was generated from total RNA with oligo (dT)12-18 priming using the Gibco®-BRL Superscript Preamplification system. First strand cDNA was amplified using human immunoglobulin variable heavy chain primers, and human immunoglobulin variable light chain primers. PCR products were sequenced and the variable heavy and light chain regions determined The nucleic acid and amino acid sequences of the variable heavy and light chain regions are listed in FIG. 2 and FIG. 3. The heavy chain variable region of H16-7.8 consists of the amino acid sequence ranging from $20^{th}$ Q residue to the $142^{nd}$ S residue of SEQ ID NO:7, and the light chain variable region of H16-7.8 consists of the amino acid sequence ranging from $20^{th}$ E residue to the $127^{th}$ R residue of SEQ ID NO:8. The heavy chain of H16-7.8 consists of the amino acid sequence ranging from $20^{th}$ Q residue to the $468^{th}$ K residue of SEQ ID NO:7 and the light chain of H16-7.8 consists of amino acid sequence ranging from $20^{th}$ E residue to the $233^{th}$ C residue of SEQ ID NO:8. Alignment of H16-7.8 to human VH4-31/D5-12/JH6 germline and human A26/JK1 germline is set forth in FIG. 4A-4B.

Example 3

Expression of H16-7.8 Using Recombinant DNA Methods

To express H16-7.8 recombinantly in transfected cells, H16-7.8 heavy and light chain sequences (SEQ ID NO:7, from 20 to 468 and the light chain of SEQ ID NO:8, from 20 to 233) were cloned into expression vectors. The complete H16-7.8 human heavy chain and light chain cassettes were cloned downstream of the CMV promoter/enhancer in a cloning vector. A polyadenylation site was included downstream of the MAb coding sequence. The recombinant H16-7.8 expressing constructs were transfected into CHO cells and recombinant H16-7.8 were secreted from CHO cells. IgG titers were measured by ELISA. Results confirmed IgG and expression and good co-expression of the heavy and light chains. Recombinant H16-7.8 were evaluated for binding to cell surface 161P2F10B by flow cytometry (FIG. 5). 3T3-control and 3T3-161P2F10B cells were stained with recombinant H16-7.8 from either hybridoma or from CHO cells transfected with H16-7.8 heavy and light chain vector constructs.

Binding was detected by flow cytometry. Results show that the recombinantly expressed H16-7.8 in CHO cells is secreted and binds specifically to cell surface 161P2F10B. (FIG. 5).

Recombinant H16-7.8 was characterized with respect to its peptide sequence. The peptide mapping analysis of H16-7.8 confirmed that the deduced amino acid sequence of H16-7.8 is correct versus the sequence determined using Lys-C digestion with LC-MS/MS, Asp-N digestion with LC-MS/MS, and N-terminal sequence by Edman degradation.

Example 4

Antibody Drug Conjugation of H16-7.8

The H16-7.8 (FIG. 2) was conjugated to a dolavaline-valine-dolaisoleucine-dolaproine-phenylalanine (aurastatin derivative) designated MMAF (Formula XVIV; monomethyl auristatin F) using a maleimidocaproyl (mc) non-cleavble linker set forth below:

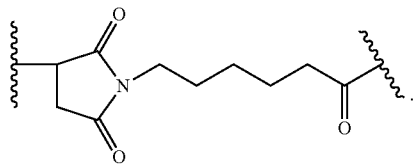 [SMILES: *C(=O)CCCCCN1C(=O)CC(*)C1=O]

The synthesis of the maleimidocaproyl (mc) non-cleavable linker to the MMAF (Seattle Genetics, Seattle, Wash.) was completed (SAFC, Madison, Wis.) using the synthesis method set forth in Table VI to create the cytotoxic mcMMAF.

Then, the antibody drug conjugate (ADC) of the invention designated H16-7.8mcMMAF was made using the following protocols.

Briefly, a 10 mg/mL solution of the H16-7.8 in 10 mM succinate, at pH 4.5 was buffer exchanged by diafiltration. The purpose of the buffer exchange is to remove H16-7.8 formulation buffer components and replace it with a more compatible buffer that is optimized for the subsequent "reduction" step. The antibody was diafiltered against 6 diavolumes (DV) of sodium borate buffer and concentrated to 10±1 mg/ml, flushed from the system, diluted to 7.5 mg/ml and 0.2 µm filtered.

Subsequently, EDTA was added to 5 mM final concentration in the reaction mixture. Next, the disulfide bonds of the H16-7.8 were partially reduced with tris-(2-carboxyethyl)-phosphine hydrochloride (TCEP) to form free thiols (SH). This process is performed at 37° C. EDTA was present at 5 mM concentration during this reaction to chelate any divalent metal cations that could cause unwanted SH re-oxidation. At the end of the reduction step the temperature of the reaction solution was lowered to 20° C. and analyzed to determine the molar ratio of free SH and to ensure that ≥3.9 SH per MAb had been generated. For conjugation, the drug-linker mcMMAF was weighed out in the isolator and dissolved in DMSO to a concentration of 5.5 mg/ml.

The SH groups on the partially reduced H16-7.8 were reacted with drug-linker mcMMAF to form the conjugate, H16-7.8mcMMAF. The mcMMAF in DMSO was added at a set molar equivalent of drug to antibody. This step was performed at 20° C. After 1 h incubation period any excess of the drug-linker in the reaction was quenched with N-Acetyl-cystein, thus eliminating any reactive drug-linker and turning it into and adduct that is easier to remove and to detect by analytical methods. The mixture is then stirred for fifteen (15) additional minutes following the addition of one (1) molar equivalents of N-Acetyl-Cysteine relative to mcMMAF.

Next, ultrafiltration/dialfiltration is performed in order to remove DMSO, process impurities, and buffer exchange the ADC into formulation buffer.

Excess quenched mcMMAF are thus removed by ultrafiltration/diafiltration of the antibody drug conjugate (ADC) with 8 diavolumes of 20 mM histidine, pH 5.2 formulation buffer. After the completion of the 8th diavolume, the solution is recirculated and assayed for protein concentration.

The conjugate is adjusted to six (6)±0.5 mg/ml with 20 mM Histidine, 10% trehalose, pH 5.2 buffer. Polysorbate 20 is then added, mixed to homogeneity, and aseptically filtered through a 0.2 µm filter.

The resulting antibody drug conjugate (ADC) is designated H16-7.8mcMMAF and has the following formula:

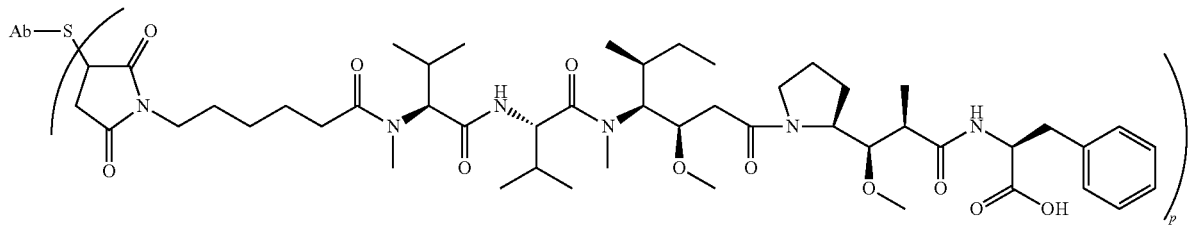

wherein MAb is H16-7.8 (FIG. 2 and FIG. 3) and p is from 1 to 12.

Example 5

Characterization of H16-7.8 and H16-7.8mcMMAF

The H16-7.8 was generated using the procedures set forth in the example entitled Example 2 "Generation of 161P2F10B Monoclonal Antibodies (MAbs)". Additionally, the Antibody Drug Conjugates that bind 161P2F10B were generated using the procedures set forth in the example entitled "Antibody Drug Conjugation of H16-7.8". The H16-7.8 and H16-7.8mcMMAF ADC were screened, identified, and characterized using a combination of assays known in the art.

A. Cell Binding and Affinity Determination by FACS

H16-7.8 and H16-7.8mcMMAF were tested for the binding affinity to 161P2F10B endogenously expressed on Ku812 cells. Briefly, eleven (11) dilutions of H16-7.8 or H16-7.8mc- MMAF are incubated with Ku812 cells (50,000 cells per well) overnight at 4° C. at a final concentration of 160 nM to 0.0001 nM. At the end of the incubation, cells are washed and incubated with anti-hIgG-PE detection antibody for 45 min at 4° C. After washing the unbound detection antibodies, the cells are analyzed by FACS. Mean Florescence Intensity (MFI) values are obtained (See, Table IV). MFI values were entered into Graphpad Prisim software and analyzed using the one site binding (hyperbola) equation of $Y=Bmax*X/(Kd+X)$ to generate H16-7.8 or H16-7.8mcMMAF saturation curves shown in FIG. 6. Bmax is the MFI value at maximal binding of H16-7.8 or H16-7.8mcMMAF to 161P2F10B; Kd is H16-7.8 or H16-7.8mcMMAF binding affinity which is the concentration of H16-7.8 or H16-7.8mcMMAF required to reach half-maximal binding.

The calculated affinity (Kd) of H16-7.8 and H16-7.8mcMMAF is 0.06 nM and 0.19 nM, respectively on 161P2F10B-related protein endogenously expressed on the surface of Ku812 cells.

To determine binding of H16-7.8 and H16-7.8mcMMAF to endogenous 161P2F10B-related protein expressed on the surface of renal cancer cells human UGK-3 cells (patient derived clear cell renal cancer) and RXF-393 cells (clear cell renal cancer) were stained with 10 μg/ml of native H16-7.8, H16-7.8mcMMAF, or an isotype control human IgG2 and evaluated by FACS.

The results in FIG. 7 (left panels) demonstrate strong staining of the two different renal tumor cells with H16-7.8 (gray lines), but not with the control MAb (filled histograms). The panels on the right demonstrate a similar strong staining of the same renal tumor cells with H16-7.8mcMMAF (gray lines). (FIG. 7; right panels). These results show that both H16-7.8 and H16-7.8mcMMAF bind native 161P2F10B antigen expressed on the surface of human cancer cells. Conjugation of native H16-7.8 to generate the H16-7.8mcMMAF did not alter its cell surface binding to native 161P2F10B antigen expressed on human cancer cells.

Example 6

Cell Cytotoxicity Mediated by H16-7.8mcMMAF

The ability of H16-7.8mcMMAF to mediate 161P2F10B-dependent cytotoxicity was evaluated in KU812 cells engineered to express 161P2F10B. For this assay 2000 viable KU812 cells were plated in triplicate on Day 0 and allowed to recover overnight. The next day, serial 1:4 dilutions of different lots of H16-7.8mcMMAF or a control MAb conjugated with mcMMAF was added to yield the final concentrations indicated in FIG. 8. The cells were allowed to incubate for six (6) days at which time 20 μl of Alamar blue was added to each well. The plates were incubated for an additional four (4) hours and the fluorescence intensity read on a fluorescent plate reader using an excitation wavelength of 540 nM and an emission wavelength of 620 nM.

The results in FIG. 8 show that both lots of H16-7.8mcMMAF potently inhibited the proliferation of KU812 cells. The IC 50 was determined to be 0.2 nM and 0.1 nM for Lot (1) and Lot (2) respectively. A fully human Control MAb that does not bind KU812 cells was conjugated with mcMMAF to yield a DAR of 3.9 (+/−0.2). The Control ADC did not inhibit KU812 cell proliferation further demonstrating the specificity of cytotoxicity. Thus, these results indicate that H16-7.8mcMMAF can selectively deliver a cytotoxic drug to 161P2F10B expressing cells leading to their killing.

Example 7

H16-7.8mcMMAF Inhibit Growth of Tumors In Vivo

The significant expression of 161P2F10B on the cell surface of tumor tissues, together with its restrictive expression in normal tissues makes 161P2F10B a good target for antibody therapy and similarly, therapy via ADC. Thus, the therapeutic efficacy of H16-7.8mcMMAF in human kidney cancer xenograft mouse models is evaluated.

Antibody drug conjugate efficacy on tumor growth and metastasis formation is studied in mouse cancer xenograft models (e.g., subcutaneous and orthotopically).

Subcutaneous (s.c.) tumors are generated by injection of $5\times10^4$-$10^6$ cancer cells mixed at a 1:1 dilution with Matrigel (Collaborative Research) in the right flank of male SCID mice. To test ADC efficacy on tumor formation, i.e., ADC injections are started on the same day as tumor-cell injections. As a control, mice are injected with either purified human IgG or PBS; or a purified MAb that recognizes an irrelevant antigen not expressed in human cells. In preliminary studies, no difference is found between control IgG or PBS on tumor growth. Tumor sizes are determined by caliper measurements, and the tumor volume is calculated as length×width× height. Mice with subcutaneous tumors greater than 1.5 cm in diameter are sacrificed.

Growth of kidney tumors in mice are performed by injection of 1.5 million to 2 million cells implanted subcutaneously into male SCID mice. Mice are monitored for general health, physical activity, and appearance until they become moribund. At the time of sacrifice, the mice can be examined to determine tumor burden and other organs harvested to evaluate metastasis to distant sites. Alternatively, death can be used as an endpoint. The mice are then segregated into groups for the appropriate treatments, with 161P2F10B or control MAbs being administered via i.v. injection.

An advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff, et al., *Clin Cancer Res.* (2001) 7:2870; Solesvik, et al., *Eur J Cancer Clin Oncol.* (1984) 20:1295). The effect of antibody and small molecule on neovascularization is studied in accordance with procedures known in the art, such as by IHC analysis of tumor tissues and their surrounding microenvironment.

H16-7.8mcMMAF inhibits formation of kidney cancer xenografts. These results indicate the utility of H16-7.8mcMMAF in the treatment of local and advanced stages of cancer and preferably those cancers set forth in Table I.

161P2F10B ADCs:

Monoclonal antibodies were raised against 161P2F10B as described in the Example entitled "Generation of 161P2F10B Monoclonal Antibodies (MAbs)." Further the MAbs are conjugated to a toxin as described in the Example entitled "Antibody Drug Conjugation of H16-7.8" to form H16-7.8mcMMAF. The H16-7.8mcMMAF is characterized by FACS, and other methods known in the art to determine its capacity to bind 161P2F10B.

Cell Lines and Xenografts:

The RFX-393 cells are maintained in RPMI, supplemented with L-glutamine and 10% FBS. UG-K3 and SKRC-01 xenografts are maintained by serial propagation in SCID mice.

Efficacy of H16-7.8mcMMAF in Subcutaneously Established Human Renal Cancer Xenograft UG-K3 in SCID Mice.

In this experiment, patient-derived human renal cancer xenograft UG-K3 was maintained by serial passages in SCID mice. Stock tumors were harvested sterilely and minced to small pieces. The tumor pieces were enzymatically digested to single cell suspensions using Liberase Blendzyme (Roche Applied Science, Indianapolis, Ind.). $1.5 \times 10^6$ cells were injected into the flanks of individual SCID mice and tumors were allowed to grow untreated until they reached an approximate volume of 100 mm$^3$ Animals were randomly assigned to the following cohorts: an H16-7.8mcMMAF treated group, an H16-7.8 control and a 5% Dextrose control. H16-7.8mcMMAF and H16-7.8 were dosed at 10 mg/kg once on day 0 by intravenous bolus injection. The amount of H16-7.8mcMMAF and H16-7.8 administered was based on the individual body weight of each animal obtained immediately prior to dosing. The 5% Dextrose control was dosed at 150 µL per animal. Tumor growth was monitored using caliper measurements every 3 to 4 days until the end of the study. Tumor volume is calculated as Width×Length/2, where width is the smallest dimension and length is the largest. Animals in control groups were humanely euthanized when tumors reached approximately 1000 mm$^3$. Animals in H16-7.8mcMMAF treated group were monitored for an additional two weeks before sacrifice. Statistical analysis was performed at the last time point when data for both control groups were available, using Kruskal-Wallis test with a=0.05.

The results demonstrated that treatment of UG-K3 renal clear cell xenograft tumors with H16-7.8mcMMAF at all doses and schedules examined resulted in significant inhibition of tumor growth in SCID mice. (FIG. 9).

Growth Inhibition of Established Orthotopic UG-K3 Xenografts by H16-7.8mcMMAF

In this experiment, the ability of H16-7.8mcMMAF to inhibit the growth of established renal tumors grown orthotopically was evaluated using patient-derived, UG-K3 tumor xenografts. Briefly, stocks of UG-K3 tumors were digested enzymatically and 1.5 million viable cells were surgically implanted into the kidneys of male SCID mice on Day 0. The tumors were allowed to grow for 7 days at which time animals were randomized to 4 different treatment groups (n=10 per group). Animals randomized to Group A received Control ADC at 5 mpk, Group B received H16-7.8mcMMAF at 3 mg/kg and Group C received H16-7.8mcMMAF at 5 mg/kg administered every 4 days for a total of 4 doses. Group D received H16-7.8mcMMAF at 10 mg/kg one time. At the end of the study (Day 41) the animals were sacrificed and the right and left kidneys weighed on an electronic balance. The tumor weights plotted on the graph were determined by subtracting the weight of the tumor-free contralateral kidney from the weight of the tumor-bearing right kidney.

The results demonstrated that treatment of UG-K3 renal clear cell xenograft tumors with H16-7.8mcMMAF at all doses and schedules examined resulted in dramatic inhibition of tumor growth (FIG. 10). Tumor weights in all H16-7.8mcMMAF treatment groups (B, C, and D) were less than 1% of the tumor weights in the Control treated group. These differences were highly statistically significant (p<0.0001, ANOVA).

Efficacy of H16-7.8mcMMAF in Subcutaneously Established Human Renal Cancer Xenograft RXF-393 in SCID Mice.

In this experiment, human renal cancer cells RXF-393 ($0.5 \times 10^6$ cells per mouse) were injected into the flanks of individual mice and tumors were allowed to grow untreated until they reached an approximate volume of 100 mm$^3$ Animals were then randomly assigned to the following cohorts: an H16-7.8mcMMAF treated group, an H16-7.8 treated group and a 5% Dextrose control. H16-7.8mcMMAF and H16-7.8 were dosed at 10 mg/kg once a week for a total of two doses by intravenous bolus injection. The amount of H16-7.8mcMMAF and H16-7.8 administered was based on the individual body weight of each animal obtained immediately prior to dosing. The 5% Dextrose control was dosed at 150 µL per animal. Tumor growth was monitored using caliper measurements every 3 to 4 days until the end of the study. Tumor volume is calculated as Width$^2$×Length/2, where width is the smallest dimension and length is the largest. Animals in control groups were humanely euthanized when tumors reached approximately 1000 mm$^3$. Animals in H16-7.8mcMMAF treated group were monitored for an additional two weeks before sacrifice.

The results demonstrated that treatment of RFX-393 human renal cancer xenograft tumors with H16-7.8mcMMAF at all doses and schedules examined (including single dose) resulted in significant inhibition of tumor growth in SCID mice. Statistical analysis was performed at the last time point when data in both control groups were available, using Kruskal-Wallis test with $\alpha$=0.05. (FIG. 11).

Efficacy Study of H16-7.8 Compared to H16-7.8mcMMAF in Subcutaneously Established Human Renal Cancer SKRC-01 in SCID Mice In another experiment, human renal cancer cells SKRC-01 ($0.8 \times 10^6$ cells per mouse) were injected into the flanks of individual mice. Tumors were allowed to grow untreated until they reached an approximate volume of 100 mm$^3$. On day 0 when tumors reach 100 mm$^3$, animals were randomly assigned to the following cohorts: an H16-7.8mcMMAF treated group, an H16-7.8 treated group and a 5% Dextrose control. H16-7.8mcMMAF and H16-7.8 were dosed at 4 mg/kg every four days for a total of four doses by intravenous bolus injection. The amount of H16-7.8mcMMAF and H16-7.8 administered was based on the individual body weight of each animal obtained immediately prior to dosing. The 5% Dextrose control was dosed at 150 µL per animal. Tumor growth was monitored using caliper measurements every 3 to 4 days. Tumor volume was calculated as Width$^2$×Length/2, where width is the smallest dimension and length is the largest.

The results show that the ADC H16-7.8mcMMAF significantly inhibited the growth of SKRC-01 tumor formation at all doses (including single dose), while the naked MAb H16-7.8 had no effect. Thus, the ADC H16-7.8mcMMAF had a significantly more prominent effect that the naked antibody H16-7.8. (FIG. 12).

Efficacy Study of H16-7.8mcMMAF compared to other 161P2F10B Antibody Drug Conjugates (ADCs) in Subcutaneous Established UG-K3 in SCID Mice In another experiment, human renal cancer cells UG-K3 ($1.5 \times 10^6$ cells per mouse) were injected into the flanks of individual mice. Tumors were allowed to grow untreated until they reached an approximate volume of 100 mm$^3$ On day 0 when tumors reach 100 mm$^3$, animals were randomly assigned to the following cohorts: an H16-7.8mcMMAF, an H16-7.8vcMMAE, and H16-1.11mcMMAF, and H16-1.11vcMMAE, a PBS control, and a control MAb-vcMMAE treated group. All antibody drug conjugates (ADCs) were dosed at 10 mg/kg once on day 0. The amount of each ADC administered was based on the individual body weight of each animal obtained immediately prior to dosing. The PBS control was dosed at 150 µ/L per animal. Tumor growth was monitored using caliper measurements every 3 to 4 days.

Tumor volume was calculated as Width×Length/2, where width is the smallest dimension and length is the largest.

The results show that the ADCs H16-7.8vcMMAE and H16-1.11vcMMAE did not inhibit tumor formation growth. Additionally, both the H16-7.8mcMMAF and H16-1.11mc-MMAF significantly inhibited the growth of UG-K3 tumor formation during the first thirty (30) days. After day thirty (30) the H16-7.8mcMMAF had a significantly more prominent effect when compared to H16-1.11mcMMAF. (FIG. 13).

Example 8

Human Clinical Trials for the Treatment and Diagnosis of Human Carcinomas Through Use of 161P2F10B ADCs 161P2F10B ADCs are used in accordance with the present invention which specifically bind to 161P2F10B, and are used in the treatment of certain tumors, preferably those listed in Table I. In connection with each of these indications, two clinical approaches are successfully pursued.

I.) Adjunctive therapy: In adjunctive therapy, patients are treated with 161P2F10B ADCs in combination with a chemotherapeutic or anti-neoplastic agent and/or radiation therapy or a combination thereof. Primary cancer targets, such as those listed in Table I, are treated under standard protocols by the addition of 161P2F10B ADCs to standard first and second line therapy. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent. 161P2F10B ADCs are utilized in several adjunctive clinical trials in combination with the chemotherapeutic or anti-neoplastic agents.

II.) Monotherapy: In connection with the use of the 161P2F10B ADCs in monotherapy of tumors, the 161P2F10B ADCs are administered to patients without a chemotherapeutic or anti-neoplastic agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody and the particular therapeutic or prophylactic effect to be achieved, and (b) the limitations inherent in the art of compounding such an active compound for the treatment of sensitivity in individuals.

An exemplary, non limiting range for a therapeutically effective amount of an 161P2F10B ADC administered in combination according to the invention is about 0.5 to about 10 mg/kg, about 1 to about 5 mg/kg, at least 1 mg/kg, at least 2 mg/kg, at least 3 mg/kg, or at least 4 mg/kg. Other exemplary non-limiting ranges are for example about 0.5 to about 5 mg/kg, or for example about 0.8 to about 5 mg/kg, or for example about 1 to about 7.5 mg/kg. The high dose embodiment of the invention relates to a dosage of more than 10 mg/kg. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Clinical Development Plan (CDP)

The CDP follows and develops treatments of 161P2F10B ADCs in connection with adjunctive therapy or monotherapy. Initially, Pre-clinical toxicology studies are performed in non-human subjects (e.g., mice, monkeys, etc.) using standard protocols known in the art. The H16-7.8mcMMAF was demonstrated to be well-tolerated in the non-human toxicology studies. The human Clinical Trials initially demonstrate safety and thereafter confirm efficacy in repeat doses. Trials are open label comparing standard chemotherapy with standard therapy plus 161P2F10B ADCs. As will be appreciated, one non-limiting criteria that can be utilized in connection with enrollment of patients is 161P2F10B expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 161P2F10B. Standard tests and follow-up are utilized to monitor each of these safety concerns. 161P2F10B MAbs are found to be safe upon human administration.

Example 9

Antibody Drug Conjugation of H16-7.8 MAb Characterization

I) Peptide Mapping by Mass Spectrometry

Peptide mapping analysis was conducted. This method is used to confirm the identity of H16-7.8mcMMAF and distinguishes native antibody (H16-7.8). The obtained H16-7.8mc-MMAF and H16-7.8 were treated with dithiothreitol (DTT) to reduce disulfide bonds, followed by alkylation of the resulting free cysteines. Guanidine was used in this step to ensure complete denaturation of the protein. After dialysis to remove the guanidine, the samples were digested with a specific endoproteinase, Lys-C. Lys-C cleaves peptide bonds on the C-terminal side of lysine residues. The resulting peptides were analyzed by reversed phase chromatography coupled to mass spectrometry. The reversed phase retention times and the observed mass to charge ratios of the peaks were compared between H16-7.8mcMMAF and H16-7.8. LC-MS (liquid chromatography-mass spectrometry) analysis was carried out using a WATERS Acquity UPLC coupled to a WATERS Q-TOFp mass spectrometer. The digested sample was applied to YMC C18 column and eluted with an acetonitrile gradient containing trifluoroacetic acid. Representative peptide maps for H16-7.8mcMMAF and H16-7.8 are shown in FIG. 14.

All three chromatograms in FIG. 14 seems to be identical except for the peaks indicated by asterisk and arrow. As can be seen in the Figure, peak intensities indicated by asterisk were reduced in the conjugated antibody compared to the native antibody. The peaks marked with an arrow represent new peaks that appeared on the conjugated antibody peptide map. Specifically, the peaks marked with either an asterisk or with an arrow are believed to be a peptide destined for conjugation and the resulting conjugated peptide, respectively. FIG. 15 shows a portion of the mass spectra of the peak marked with an asterisk. The mass value of the signal that changed during conjugation is indicated by the "plus" sign. This peptide with an approximate m/z of 970.4 (+3 charge state) was identified as C225-K250 that originated from the hinge region of the heavy chain and contains the expected conjugation sites.

In order to identify the newly appeared peaks which are believed to be conjugated peptide in FIG. 14, LC-MS analysis was conducted using the elevated-energy (MSE) data acquisition technique. FIG. 16 shows the extracted ion chromatograms (XIC) for peptide maps of H16-7.8mcMMAF and H16-7.8 using the m/z of 619.4. This ion corresponds to a fragment ion of the drug moiety. Peaks observed in XIC at 619.4 are almost identical to the peaks marked with an arrow in FIG. 14. Furthermore, no such peaks were detected in the chromatogram of the native antibody. These observations suggest that the detected peaks in the XIC at m/z of 619.4 were apparently drug conjugated peptides and are identified by its intact mass values. The result was summarized in Table V. These results suggest that in case of the conjugate, predominant peptides are those conjugated to 2 drugs on the hinge region of heavy chain. These data are consistent with the data obtained by the other orthogonal such as a DAR analysis.

II) Intact Mass Analysis by LC-MS

The full mass of the deglycosylated H16-7.8mcMMAF was determined by electrospray ionization time-of-flight (ESI-TOF) mass spectrometry. This technique provides direct information about the drug-to-antibody ratio (DAR) value. Test samples were diluted by 250 mM sodium phosphate buffer, pH 7.5 and then incubated overnight at 37° C. with Glycopeptidase F. The samples were injected onto a PLRPTM column (Varian Technology), equilibrated at 90° C., and eluted with an acetonitrile/water gradient. The sample peaks were analyzed by an Acquity UPLC system coupled to an WATERS Synapt mass spectrometer (Waters) and masses were reconstructed from the raw data by an MaxEnt1 software. An example mass spectral profile for the deglycosylated H16-7.8mcMMAF is shown in FIG. 17. The predominant drug conjugated antibody was a 4-drug loading species. This observation including an abundance of the unconjugated antibody in H16-7.8mcMMAF was consistent with the results obtained by the other orthogonal methods, such as DAR by RP-HPLC, peptide mapping and HIC assay.

III) Drug to Antibody Ratio (DAR) Analysis by RP-HPLC

Drug to Antibody Ratio (DAR) analysis was conducted for quantitative HPLC determination of the relative amount of drug loading in each Light chain and Heavy chain. DAR analyses were carried out using a PLRP-S analytical column, 2.1 mm×50 mm, with mobile phase A consisting of 2.0% formic acid and mobile phase B consisting of 2.0% formic acid plus 90% acetonitrile. For sample preparation, the drug conjugated antibody was completely reduced by DTT and then separated to the L chain, the drug conjugated L chain, the H chain and the drug conjugated H chains based on the drug loading amount. 50 μg of sample was eluted using a flow rate of 0.5 ml/min, with detection at 280 nm. The molar ratio of drug to antibody ratio (DAR) is defined by the following equation.

$$DAR = \left( \sum_{n=0}^{1} \left( \frac{AUC_{Light,n}}{AUC_{Total,Light}} \times n \right) + \sum_{n=0}^{5} \left( \frac{AUC_{Heavy,n}}{AUC_{Total,Heavy}} \times n \right) \right) \times 2$$

Where
DAR—drug to antibody molar ratio
n—number of mcMMAF drugs per Ab chain
AUCLight,n, AUCHeavy,n—area under curve for the light or heavy antibody chain with n drugs, respectively;
AUCTotal, Light(Heavy)—peak area under curve of the light or heavy chain.

This method has been qualified using material from H16-7.8mcMMAF. Parameters evaluated included specificity, accuracy, repeatability, intermediate precision. A representative DAR profile for H16-7.8mcMMAF is shown in FIG. 18. DAR value is 4.0. Sample was subjected to LC-MS analysis using same HPLC conditions of this method to identify the observed peak. Results are summarized in Table VI. The peak identification of the DAR results obtained during the qualification of this method has been confirmed orthogonally by LC-MS.

IV) Binding Affinity

H16-7.8 and H16-7.8mcMMAF were tested for their binding affinity to 161P2F10B expressed on KU812 cells (human chronic myelogenous leukemia cells, ATCC). Briefly, twelve (12) dilutions of H16-7.8 or H16-7.8mcMMAF were incubated with KU812 cells (50,000 cells per well) overnight at 4° C. at a final concentration of 160 nM to 0.004 nM. At the end of the incubation, cells are washed and incubated with anti-hIgG-PE detection antibody for 45 min at 4° C. After washing the unbound detection antibodies, the cells are analyzed by FACS.

MFI values were entered into Graphpad Prisim software and analyzed using the one site binding (hyperbola) equation of Y=Bmax*X/(Kd+X) to generate H16-7.8 and H16-7.8mcMMAF saturation curves. Bmax is the MFI value at maximal binding of H16-7.8 or H16-7.8mcMMAF to KU812; Kd is H16-7.8 or H16-7.8mcMMAF binding affinity which are the concentration of H16-7.8 or H16-7.8mcMMAF required to reach halfmaximal binding. The calculated affinity (Kd) of H16-7.8 and H16-7.8mcMMAF is 0.08 nM and 0.25 nM on 161P2F10B expressed on the surface of KU812 cells, respectively. (n=4).

V) Cytotoxicity

The H16-7.8, H16-7.8mcMMAF and a negative control ADC were separately serially diluted and added to a 96-well plate containing KU812 cells, which endogenously express 161P2F10B on the cell surface. After six days of incubation, Alamar Blue® reagent is added to the antibody-cell mixture. AlamarBlue® is a cell viability indicator that uses the natural reducing power of living cells to convert resazurin to the fluorescent molecule, resorufin. Resazurin is reduced to resorufin, which produces very bright red fluorescence. Viable cells continuously convert resazurin to resorufin, thereby generating a quantitative measure of viability—and cytotoxicity. The percent cytotoxicity of H16-7.8mcMMAF is evaluated using fluorescence units obtained spectrophotometrically using the Synergy 4 Hybrid Multi-Mode Microplate reader (540/35, 620/40 nm). The linear range of the assay is approximately 3.9 to 1000 ng/ml. There are 9 points in the standard curve: the highest concentration of H16-7.8mcMMAF is 1000 ng/ml followed by eight serial 1 to 2 dilutions and a blank (0).

Calculate % Survival using formula below:

% Survival=(X−Blank)/(No treated−Blank)×100

Specific cytotoxicity activity of H16-7.8mcMMAF on KU812 cells: IC50 0.15 nM.

H16-7.8 and ADC control (antibody(non-anti-161P2F10B antibody)-mcMMAF) did not have cytotoxicity activity on KU812 cells.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues that express 161P2F10B when malignant.

Kidney
Colon
Lung
Ovary
Breast
Lymphoma
Bone
Uterus
Pancreas
Liver
Prostate

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|   | 9 | −3 | −4 | −2 | −3 | −3 | −1 | −3 | −1 | −1 | −3 | −3 | −3 | −3 | −1 | −1 | −1 | −2 | −2 | C |
|   |   | 6 | 2 | −3 | −1 | −1 | −3 | −1 | −4 | −3 | 1 | −1 | 0 | −2 | 0 | −1 | −3 | −4 | −3 | D |
|   |   |   | 5 | −3 | −2 | 0 | −3 | 1 | −3 | −2 | 0 | −1 | 2 | 0 | 0 | −1 | −2 | −3 | −2 | E |
|   |   |   |   | 6 | −3 | −1 | 0 | −3 | 0 | 0 | −3 | −4 | −3 | −3 | −2 | −2 | −1 | 1 | 3 | F |
|   |   |   |   |   | 6 | −2 | −4 | −2 | −4 | −3 | 0 | −2 | −2 | −2 | 0 | −2 | −3 | −2 | −3 | G |
|   |   |   |   |   |   | 8 | −3 | −1 | −3 | −2 | 1 | −2 | 0 | 0 | −1 | −2 | −3 | −2 | 2 | H |
|   |   |   |   |   |   |   | 4 | −3 | 2 | 1 | −3 | −3 | −3 | −3 | −2 | −1 | 3 | −3 | −1 | I |
|   |   |   |   |   |   |   |   | 5 | −2 | −1 | 0 | −1 | 1 | 2 | 0 | −1 | −2 | −3 | −2 | K |
|   |   |   |   |   |   |   |   |   | 4 | 2 | −3 | −3 | −2 | −2 | −2 | −1 | 1 | −2 | −1 | L |
|   |   |   |   |   |   |   |   |   |   | 5 | −2 | −2 | 0 | −1 | −1 | −1 | 1 | −1 | −1 | M |
|   |   |   |   |   |   |   |   |   |   |   | 6 | −2 | 0 | 0 | 1 | 0 | −3 | −4 | −2 | N |
|   |   |   |   |   |   |   |   |   |   |   |   | 7 | −1 | −2 | −1 | −1 | −2 | −4 | −3 | P |
|   |   |   |   |   |   |   |   |   |   |   |   |   | 5 | 1 | 0 | −1 | −2 | −2 | −1 | Q |

TABLE III-continued

Amino Acid Substitution Matrix

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
|   |   |   |   |   |   |   |   |   |   |   |   |   |   | 5 | −1 | −1 | −3 | −3 | −2 | R |
|   |   |   |   |   |   |   |   |   |   |   |   |   |   |   | 4 | 1 | −2 | −3 | −2 | S |
|   |   |   |   |   |   |   |   |   |   |   |   |   |   |   |   | 5 | 0 | −2 | −2 | T |
|   |   |   |   |   |   |   |   |   |   |   |   |   |   |   |   |   | 4 | −3 | −1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

Adapted from the GCG Software 9.0 BLOSUM62 amino acid substitution matrix (block substitution matrix). The higher the value, the more likely a substitution is found in related, natural proteins.

TABLE IV

FACS MFI Values on Ku812 cells

| nM | H16-7.8 | H16-7.8mcMMAF |
|---|---|---|
| 160 | 99 | 108 |
| 80 | 92 | 102 |
| 40 | 98 | 108 |
| 20 | 89 | 97 |
| 10 | 75 | 89 |
| 5 | 71 | 80 |
| 2.5 | 65 | 68 |
| 1.3 | 59 | 60 |
| 0.63 | 57 | 57 |
| 0.31 | 58 | 54 |
| 0.16 | 53 | 47 |
| 0.078 | 47 | 37 |
| 0.039 | 36 | 30 |
| 0.020 | 27 | 20 |
| 0.010 | 18 | 14 |
| 0.0049 | 13 | 11 |
| 0.0024 | 9 | 8 |
| 0.0012 | 7 | 7 |
| 0.0006 | 6 | 6 |
| 0.0003 | 6 | 6 |
| 0.0002 | 6 | 5 |
| 0.0001 | 5 | 5 |

TABLE V

Summary of the peak identification results on the drug conjugated peptides, potential conjugation sites (cystein residues) are set forth in bold type and underlined.

| Peak No. | Predominant observed mass | Calculate mass | Tentative Identification | Sequence Identification |
|---|---|---|---|---|
| 1 | 1754.81 | 1736.51 | $S_{208}$FNRGEC$_{214}$ + 1mcMMAF + $H_2O$, Light chain | SEQ ID NO: 9 |
| 2 | 1736.82 | 1736.51 | $S_{208}$FNRGEC$_{214}$ + 1mcMMAF, Light chain | SEQ ID NO: 9 |
| 3 | 4679.29 | 4643.72 | C$_{225}$CVECPPCPAPPVGPSVFLFPPKPK$_{249}$ + 2mcMMAF + $2H_2O$, Heavy chain | SEQ ID NO: 10 |
| 4 | 4661.29 | 4643.72 | C$_{225}$CVECPPCPAPPVGPSVFLFPPKPK$_{249}$ + 2mcMMAF + $H_2O$, Heavy chain | SEQ ID NO: 10 |
| 5 | 4643.20 | 4643.72 | C$_{225}$CVECPPCPAPPVGPSVFLEPPKPK$_{249}$ + 2mcMMAF, Heavy chain | SEQ ID NO: 10 |
| 6 | 4704.39 | 4643.72 | C$_{225}$CVECPPCPAPPVGPSVFLEPPKPK$_{249}$ + 2mcMMAF, Heavy chain | SEQ ID NO: 10 |
| 7 | 4644.38 | 4643.72 | C$_{225}$CVECPPCPAPPVGPSVFLFPPKPK$_{249}$ + 2mcMMAF, Heavy chain | SEQ ID NO: 10 |
| 8 | 4626.27 | 4643.72 | C$_{225}$CVECPPCPAPPVGPSVFLFPPKPK$_{249}$ + 2mcMMAF−$H_2O$, Heavy chain | SEQ ID NO: 10 |

TABLE VI

Peak identification results of DAR analysis by LC-MS

| Peak No | Observed mass | Mass difference from unconjugated peak | Assignments |
|---|---|---|---|
| L0 | 23596.1055 | N/A | Unconjugated L chain |
| L1 | 24521.7031 | 925.6 | 1 drug conjugated L chain |
| H0 | 50304.9102 | N/A | Unconjugated H chain |
| H1 | 51230.3984 | 925.5 | 1 drug conjugated H chain |
| H2 | 52155.9023 | 1851.0 | 2 drug conjugated H chain |
| H3 | 53085.2813 | 2780.4 | 3 drug conjugated H chain |
| H4 | 54006.7422 | 3701.8 | 4 drug conjugated H chain |
| H5 | 54929.6002 | 4624.7 | 5 drug conjugated H chain |

TABLE VII

Synthetic Scheme of mcMMAF

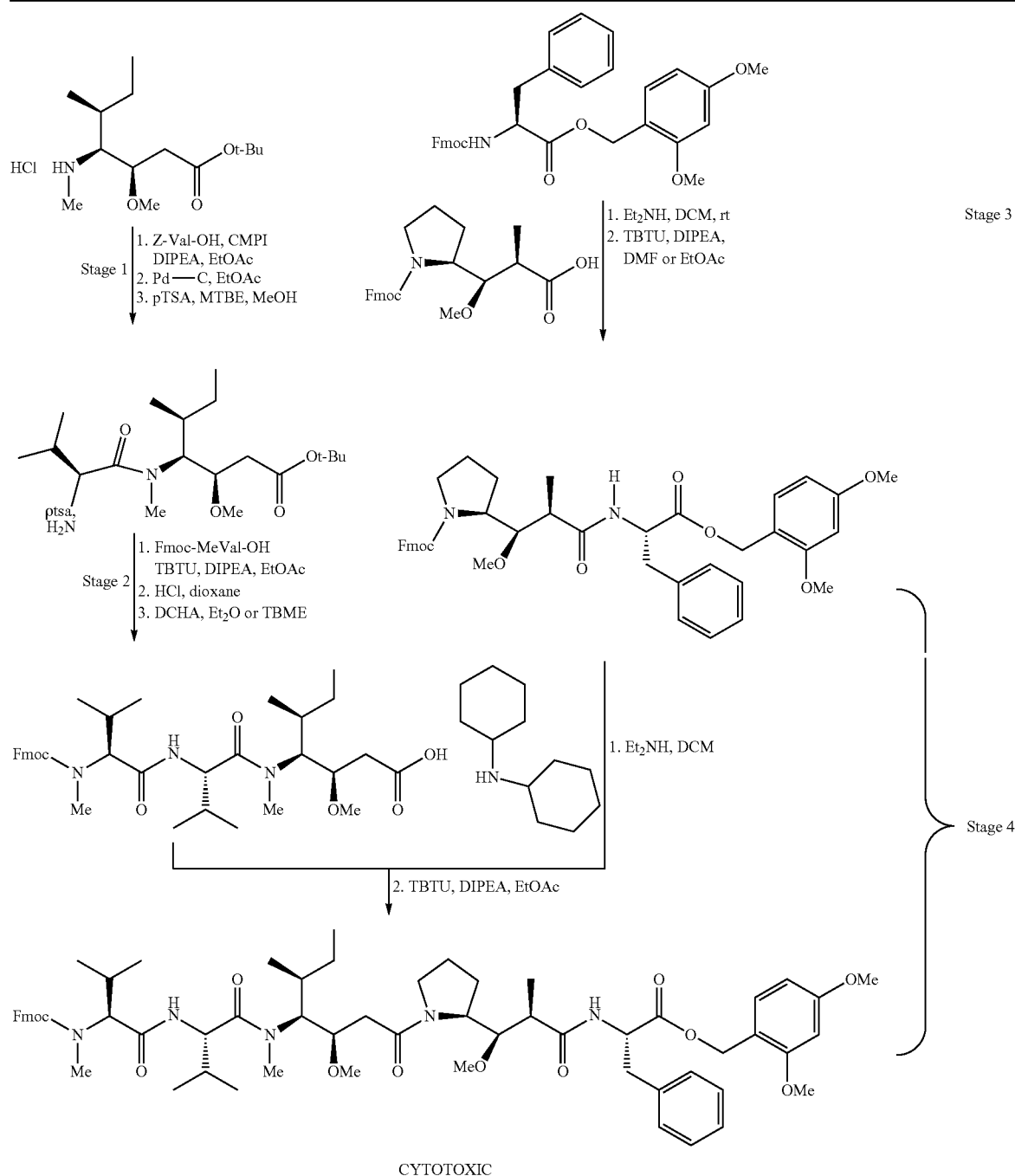

CYTOTOXIC

TABLE VII-continued

Synthetic Scheme of mcMMAF

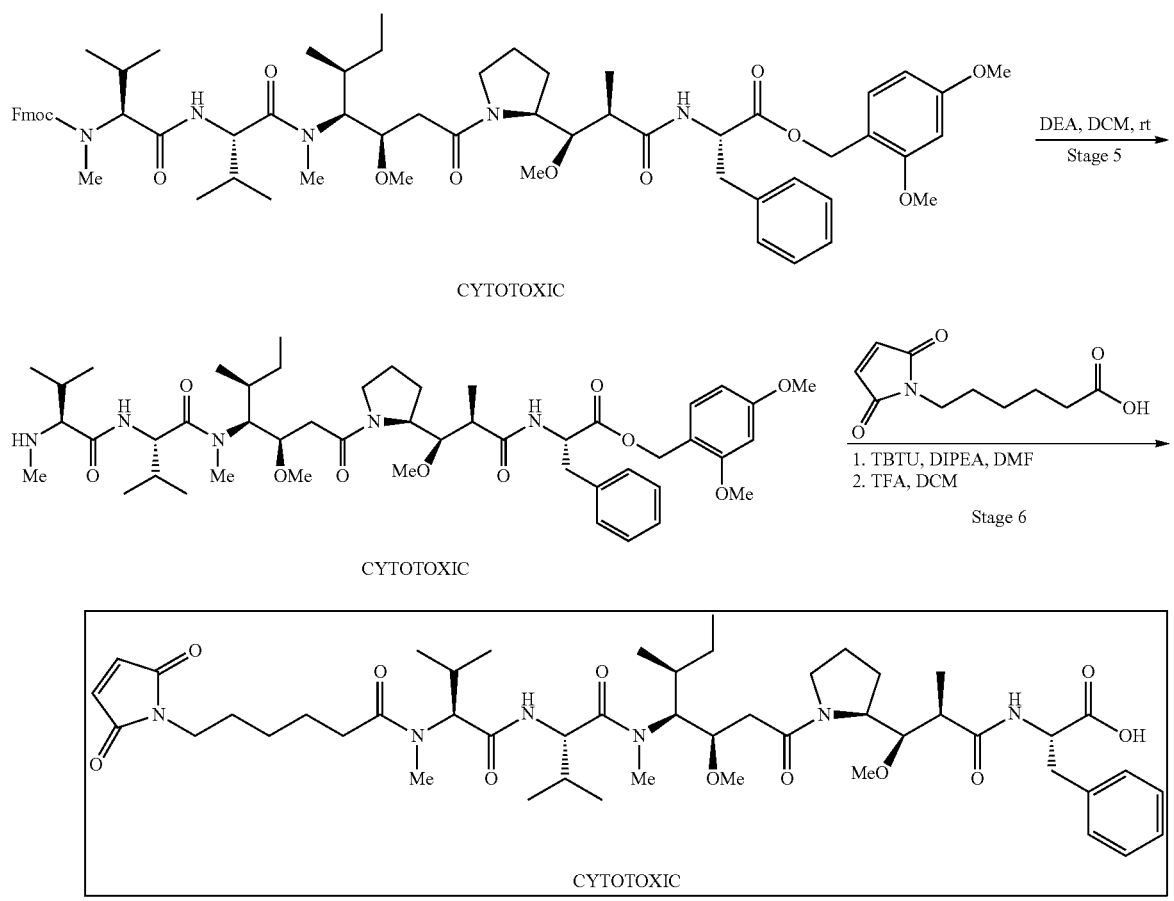

The invention claimed is:

1. An antibody drug conjugate, comprising an antibody or antigen binding fragment thereof that binds specifically to a 161P2F10B protein comprising the amino acid sequence of SEQ ID NO:2, wherein the antibody comprises the amino acid sequence of the $V_H$ region of SEQ ID NO:7, from 20 to 142, and the $V_L$, region of SEQ ID NO:8, from 20 to 127 and wherein said antibody is conjugated to monomethyl auristatin F (MMAF).

2. The antibody drug conjugate of claim 1, wherein the antigen binding fragment is an Fab, F(ab')$_2$ or Fv fragment.

3. The antibody drug conjugate of claim 1, wherein the antibody is a fully human antibody.

4. The antibody drug conjugate of claim 1, which is recombinantly produced.

5. A pharmaceutical composition that comprises the antibody drug conjugate of claim 1 in a human unit dose form.

* * * * *

SEQUENCE LISTING

<160> NUMBER OF SEQ ID NOS: 12

<210> SEQ ID NO 1
<211> LENGTH: 3858
<212> TYPE: DNA
<213> ORGANISM: Homo sapiens
<220> FEATURE:
<221> NAME/KEY: misc_feature
<222> LOCATION: (1)...(3858)
<223> OTHER INFORMATION: 161P2F10B variant 2
<220> FEATURE:
<221> NAME/KEY: CDS
<222> LOCATION: (44)...(2671)

<400> SEQUENCE: 1

```
ctactttatt ctgataaaac aggtctatgc agctaccagg aca atg gaa tct acg         55
                                              Met Glu Ser Thr
                                               1 ttg act tta gca acg gaa caa cct gtt aag aag aac act ctt aag aaa        103
Leu Thr Leu Ala Thr Glu Gln Pro Val Lys Lys Asn Thr Leu Lys Lys
 5               10                  15                  20 tat aaa ata gct tgc att gtt ctt ctt gct ttg ctg gtg atc atg tca        151
Tyr Lys Ile Ala Cys Ile Val Leu Leu Ala Leu Leu Val Ile Met Ser
            25                  30                  35
```

-continued

| | | | | | | | | | | | | | | | | |
|---|---|---|---|---|---|---|---|---|---|---|---|---|---|---|---|---|
| ctt | gga | tta | ggc | ctg | ggg | ctt | gga | ctc | agg | aaa | ctg | gaa | aag | caa | ggc | 199 |
| Leu | Gly | Leu | Gly | Leu | Gly | Leu | Gly | Leu | Arg | Lys | Leu | Glu | Lys | Gln | Gly | |
| | | | 40 | | | | | 45 | | | | | 50 | | | |

| agc | tgc | agg | aag | aag | tgc | ttt | gat | gca | tca | ttt | aga | gga | ctg | gag | aac | 247 |
|---|---|---|---|---|---|---|---|---|---|---|---|---|---|---|---|---|
| Ser | Cys | Arg | Lys | Lys | Cys | Phe | Asp | Ala | Ser | Phe | Arg | Gly | Leu | Glu | Asn | |
| | | 55 | | | | | 60 | | | | | 65 | | | | |

| tgc | cgg | tgt | gat | gtg | gca | tgt | aaa | gac | cga | ggt | gat | tgc | tgc | tgg | gat | 295 |
|---|---|---|---|---|---|---|---|---|---|---|---|---|---|---|---|---|
| Cys | Arg | Cys | Asp | Val | Ala | Cys | Lys | Asp | Arg | Gly | Asp | Cys | Cys | Trp | Asp | |
| | 70 | | | | | 75 | | | | | 80 | | | | | |

| ttt | gaa | gac | acc | tgt | gtg | gaa | tca | act | cga | ata | tgg | atg | tgc | aat | aaa | 343 |
|---|---|---|---|---|---|---|---|---|---|---|---|---|---|---|---|---|
| Phe | Glu | Asp | Thr | Cys | Val | Glu | Ser | Thr | Arg | Ile | Trp | Met | Cys | Asn | Lys | |
| 85 | | | | | 90 | | | | | 95 | | | | | 100 | |

| ttt | cgt | tgt | gga | gag | acc | aga | tta | gag | gcc | agc | ctt | tgc | tct | tgt | tca | 391 |
|---|---|---|---|---|---|---|---|---|---|---|---|---|---|---|---|---|
| Phe | Arg | Cys | Gly | Glu | Thr | Arg | Leu | Glu | Ala | Ser | Leu | Cys | Ser | Cys | Ser | |
| | | | | 105 | | | | | 110 | | | | | 115 | | |

| gat | gac | tgt | ttg | cag | agg | aaa | gat | tgc | tgt | gct | gac | tat | aag | agt | gtt | 439 |
|---|---|---|---|---|---|---|---|---|---|---|---|---|---|---|---|---|
| Asp | Asp | Cys | Leu | Gln | Arg | Lys | Asp | Cys | Cys | Ala | Asp | Tyr | Lys | Ser | Val | |
| | | | 120 | | | | | 125 | | | | | 130 | | | |

| tgc | caa | gga | gaa | acc | tca | tgg | ctg | gaa | gaa | aac | tgt | gac | aca | gcc | cag | 487 |
|---|---|---|---|---|---|---|---|---|---|---|---|---|---|---|---|---|
| Cys | Gln | Gly | Glu | Thr | Ser | Trp | Leu | Glu | Glu | Asn | Cys | Asp | Thr | Ala | Gln | |
| | | 135 | | | | | 140 | | | | | 145 | | | | |

| cag | tct | cag | tgc | cca | gaa | ggg | ttt | gac | ctg | cca | cca | gtt | atc | ttg | ttt | 535 |
|---|---|---|---|---|---|---|---|---|---|---|---|---|---|---|---|---|
| Gln | Ser | Gln | Cys | Pro | Glu | Gly | Phe | Asp | Leu | Pro | Pro | Val | Ile | Leu | Phe | |
| | 150 | | | | | 155 | | | | | 160 | | | | | |

| tct | atg | gat | gga | ttt | aga | gct | gaa | tat | tta | tac | aca | tgg | gat | act | tta | 583 |
|---|---|---|---|---|---|---|---|---|---|---|---|---|---|---|---|---|
| Ser | Met | Asp | Gly | Phe | Arg | Ala | Glu | Tyr | Leu | Tyr | Thr | Trp | Asp | Thr | Leu | |
| 165 | | | | | 170 | | | | | 175 | | | | | 180 | |

| atg | cca | aat | atc | aat | aaa | ctg | aaa | aca | tgt | gga | att | cat | tca | aaa | tac | 631 |
|---|---|---|---|---|---|---|---|---|---|---|---|---|---|---|---|---|
| Met | Pro | Asn | Ile | Asn | Lys | Leu | Lys | Thr | Cys | Gly | Ile | His | Ser | Lys | Tyr | |
| | | | | 185 | | | | | 190 | | | | | 195 | | |

| atg | aga | gct | atg | tat | cct | acc | aaa | acc | ttc | cca | aat | cat | tac | acc | att | 679 |
|---|---|---|---|---|---|---|---|---|---|---|---|---|---|---|---|---|
| Met | Arg | Ala | Met | Tyr | Pro | Thr | Lys | Thr | Phe | Pro | Asn | His | Tyr | Thr | Ile | |
| | | | 200 | | | | | 205 | | | | | 210 | | | |

| gtc | acg | ggc | ttg | tat | cca | gag | tca | cat | ggc | atc | att | gac | aat | aat | atg | 727 |
|---|---|---|---|---|---|---|---|---|---|---|---|---|---|---|---|---|
| Val | Thr | Gly | Leu | Tyr | Pro | Glu | Ser | His | Gly | Ile | Ile | Asp | Asn | Asn | Met | |
| | | 215 | | | | | 220 | | | | | 225 | | | | |

| tat | gat | gta | aat | ctc | aac | aag | aat | ttt | tca | ctt | tct | tca | aag | gaa | caa | 775 |
|---|---|---|---|---|---|---|---|---|---|---|---|---|---|---|---|---|
| Tyr | Asp | Val | Asn | Leu | Asn | Lys | Asn | Phe | Ser | Leu | Ser | Ser | Lys | Glu | Gln | |
| | 230 | | | | | 235 | | | | | 240 | | | | | |

| aat | aat | cca | gcc | tgg | tgg | cat | ggg | caa | cca | atg | tgg | ctg | aca | gca | atg | 823 |
|---|---|---|---|---|---|---|---|---|---|---|---|---|---|---|---|---|
| Asn | Asn | Pro | Ala | Trp | Trp | His | Gly | Gln | Pro | Met | Trp | Leu | Thr | Ala | Met | |
| 245 | | | | | 250 | | | | | 255 | | | | | 260 | |

| tat | caa | ggt | tta | aaa | gcc | gct | acc | tac | ttt | tgg | ccc | gga | tca | gaa | gtg | 871 |
|---|---|---|---|---|---|---|---|---|---|---|---|---|---|---|---|---|
| Tyr | Gln | Gly | Leu | Lys | Ala | Ala | Thr | Tyr | Phe | Trp | Pro | Gly | Ser | Glu | Val | |
| | | | | 265 | | | | | 270 | | | | | 275 | | |

| gct | ata | aat | ggc | tcc | ttt | cct | tcc | ata | tac | atg | cct | tac | aac | gga | agt | 919 |
|---|---|---|---|---|---|---|---|---|---|---|---|---|---|---|---|---|
| Ala | Ile | Asn | Gly | Ser | Phe | Pro | Ser | Ile | Tyr | Met | Pro | Tyr | Asn | Gly | Ser | |
| | | | 280 | | | | | 285 | | | | | 290 | | | |

| gtc | cca | ttt | gaa | gag | agg | att | tct | aca | ctg | tta | aaa | tgg | ctg | gac | ctg | 967 |
|---|---|---|---|---|---|---|---|---|---|---|---|---|---|---|---|---|
| Val | Pro | Phe | Glu | Glu | Arg | Ile | Ser | Thr | Leu | Leu | Lys | Trp | Leu | Asp | Leu | |
| | | 295 | | | | | 300 | | | | | 305 | | | | |

| ccc | aaa | gct | gaa | aga | ccc | agg | ttt | tat | acc | atg | tat | ttt | gaa | gaa | cct | 1015 |
|---|---|---|---|---|---|---|---|---|---|---|---|---|---|---|---|---|
| Pro | Lys | Ala | Glu | Arg | Pro | Arg | Phe | Tyr | Thr | Met | Tyr | Phe | Glu | Glu | Pro | |
| | 310 | | | | | 315 | | | | | 320 | | | | | |

| gat | tcc | tct | gga | cat | gca | ggt | gga | cca | gtc | agt | gcc | aga | gta | att | aaa | 1063 |
|---|---|---|---|---|---|---|---|---|---|---|---|---|---|---|---|---|
| Asp | Ser | Ser | Gly | His | Ala | Gly | Gly | Pro | Val | Ser | Ala | Arg | Val | Ile | Lys | |
| 325 | | | | | 330 | | | | | 335 | | | | | 340 | |

| gcc | tta | cag | gta | gta | gat | cat | gct | ttt | ggg | atg | ttg | atg | gaa | ggc | ctg | 1111 |
|---|---|---|---|---|---|---|---|---|---|---|---|---|---|---|---|---|
| Ala | Leu | Gln | Val | Val | Asp | His | Ala | Phe | Gly | Met | Leu | Met | Glu | Gly | Leu | |
| | | | | 345 | | | | | 350 | | | | | 355 | | |

```
aag cag cgg aat ttg cac aac tgt gtc aat atc atc ctt ctg gct gac      1159
Lys Gln Arg Asn Leu His Asn Cys Val Asn Ile Ile Leu Leu Ala Asp
        360                 365                 370 cat gga atg gac cag act tat tgt aac aag atg gaa tac atg act gat      1207
His Gly Met Asp Gln Thr Tyr Cys Asn Lys Met Glu Tyr Met Thr Asp
            375                 380                 385 tat ttt ccc aga ata aac ttc ttc tac atg tac gaa ggg cct gcc ccc      1255
Tyr Phe Pro Arg Ile Asn Phe Phe Tyr Met Tyr Glu Gly Pro Ala Pro
    390                 395                 400 cgc atc cga gct cat aat ata cct cat gac ttt ttt agt ttt aat tct      1303
Arg Ile Arg Ala His Asn Ile Pro His Asp Phe Phe Ser Phe Asn Ser
405                 410                 415                 420 gag gaa att gtt aga aac ctc agt tgc cga aaa cct gat cag cat ttc      1351
Glu Glu Ile Val Arg Asn Leu Ser Cys Arg Lys Pro Asp Gln His Phe
                425                 430                 435 aag ccc tat ttg act cct gat ttg cca aag cga ctg cac tat gcc aag      1399
Lys Pro Tyr Leu Thr Pro Asp Leu Pro Lys Arg Leu His Tyr Ala Lys
            440                 445                 450 aac gtc aga atc gac aaa gtt cat ctc ttt gtg gat caa cag tgg ctg      1447
Asn Val Arg Ile Asp Lys Val His Leu Phe Val Asp Gln Gln Trp Leu
        455                 460                 465 gct gtt agg agt aaa tca aat aca aat tgt gga gga ggc aac cat ggt      1495
Ala Val Arg Ser Lys Ser Asn Thr Asn Cys Gly Gly Gly Asn His Gly
    470                 475                 480 tat aac aat gag ttt agg agc atg gag gct atc ttt ctg gca cat gga      1543
Tyr Asn Asn Glu Phe Arg Ser Met Glu Ala Ile Phe Leu Ala His Gly
485                 490                 495                 500 ccc agt ttt aaa gag aag act gaa gtt gaa cca ttt gaa aat att gaa      1591
Pro Ser Phe Lys Glu Lys Thr Glu Val Glu Pro Phe Glu Asn Ile Glu
                505                 510                 515 gtc tat aac cta atg tgt gat ctt cta cgc att caa cca gca cca aac      1639
Val Tyr Asn Leu Met Cys Asp Leu Leu Arg Ile Gln Pro Ala Pro Asn
            520                 525                 530 aat gga acc cat ggt agt tta aac cat ctt ctg aag gtg cct ttt tat      1687
Asn Gly Thr His Gly Ser Leu Asn His Leu Leu Lys Val Pro Phe Tyr
        535                 540                 545 gag cca tcc cat gca gag gag gtg tca aag ttt tct gtt tgt ggc ttt      1735
Glu Pro Ser His Ala Glu Glu Val Ser Lys Phe Ser Val Cys Gly Phe
    550                 555                 560 gct aat cca ttg ccc aca gag tct ctt gac tgt ttc tgc cct cac cta      1783
Ala Asn Pro Leu Pro Thr Glu Ser Leu Asp Cys Phe Cys Pro His Leu
565                 570                 575                 580 caa aat agt act cag ctg gaa caa gtg aat cag atg cta aat ctc acc      1831
Gln Asn Ser Thr Gln Leu Glu Gln Val Asn Gln Met Leu Asn Leu Thr
                585                 590                 595 caa gaa gaa ata aca gca aca gtg aaa gta aat ttg cca ttt ggg agg      1879
Gln Glu Glu Ile Thr Ala Thr Val Lys Val Asn Leu Pro Phe Gly Arg
            600                 605                 610 cct agg gta ctg cag aag aac gtg gac cac tgt ctc ctt tac cac agg      1927
Pro Arg Val Leu Gln Lys Asn Val Asp His Cys Leu Leu Tyr His Arg
        615                 620                 625 gaa tat gtc agt gga ttt gga aaa gct atg agg atg ccc atg tgg agt      1975
Glu Tyr Val Ser Gly Phe Gly Lys Ala Met Arg Met Pro Met Trp Ser
    630                 635                 640 tca tac aca gtc ccc cag ttg gga gac acg tcg cct ctg cct ccc act      2023
Ser Tyr Thr Val Pro Gln Leu Gly Asp Thr Ser Pro Leu Pro Pro Thr
645                 650                 655                 660 gtc cca gac tgt ctg cgg gct gat gtc agg gtt cct cct tct gag agc      2071
Val Pro Asp Cys Leu Arg Ala Asp Val Arg Val Pro Pro Ser Glu Ser
                665                 670                 675
```

| | | |
|---|---|---|
| caa aaa tgt tcc ttc tat tta gca gac aag aat atc acc cac ggc ttc<br>Gln Lys Cys Ser Phe Tyr Leu Ala Asp Lys Asn Ile Thr His Gly Phe<br>680 685 690 | | 2119 |
| ctc tat cct cct gcc agc aat aga aca tca gat agc caa tat gat gct<br>Leu Tyr Pro Pro Ala Ser Asn Arg Thr Ser Asp Ser Gln Tyr Asp Ala<br>695 700 705 | | 2167 |
| tta att act agc aat ttg gta cct atg tat gaa gaa ttc aga aaa atg<br>Leu Ile Thr Ser Asn Leu Val Pro Met Tyr Glu Glu Phe Arg Lys Met<br>710 715 720 | | 2215 |
| tgg gac tac ttc cac agt gtt ctt ctt ata aaa cat gcc aca gaa aga<br>Trp Asp Tyr Phe His Ser Val Leu Leu Ile Lys His Ala Thr Glu Arg<br>725 730 735 740 | | 2263 |
| aat gga gta aat gtg gtt agt gga cca ata ttt gat tat aat tat gat<br>Asn Gly Val Asn Val Val Ser Gly Pro Ile Phe Asp Tyr Asn Tyr Asp<br>745 750 755 | | 2311 |
| ggc cat ttt gat gct cca gat gaa att acc aaa cat tta gcc aac act<br>Gly His Phe Asp Ala Pro Asp Glu Ile Thr Lys His Leu Ala Asn Thr<br>760 765 770 | | 2359 |
| gat gtt ccc atc cca aca cac tac ttt gtg gtg ctg acc agt tgt aaa<br>Asp Val Pro Ile Pro Thr His Tyr Phe Val Val Leu Thr Ser Cys Lys<br>775 780 785 | | 2407 |
| aac aag agc cac aca ccg gaa aac tgc cct ggg tgg ctg gat gtc cta<br>Asn Lys Ser His Thr Pro Glu Asn Cys Pro Gly Trp Leu Asp Val Leu<br>790 795 800 | | 2455 |
| ccc ttt atc atc cct cac cga cct acc aac gtg gag agc tgt cct gaa<br>Pro Phe Ile Ile Pro His Arg Pro Thr Asn Val Glu Ser Cys Pro Glu<br>805 810 815 820 | | 2503 |
| ggt aaa cca gaa gct ctt tgg gtt gaa gaa aga ttt aca gct cac att<br>Gly Lys Pro Glu Ala Leu Trp Val Glu Glu Arg Phe Thr Ala His Ile<br>825 830 835 | | 2551 |
| gcc cgg gtc cgt gat gta gaa ctt ctc act ggg ctt gac ttc tat cag<br>Ala Arg Val Arg Asp Val Glu Leu Leu Thr Gly Leu Asp Phe Tyr Gln<br>840 845 850 | | 2599 |
| gat aaa gtg cag cct gtc tct gaa att ttg caa cta aag aca tat tta<br>Asp Lys Val Gln Pro Val Ser Glu Ile Leu Gln Leu Lys Thr Tyr Leu<br>855 860 865 | | 2647 |
| cca aca ttt gaa acc act att taa cttaataatg tctacttaat atataattta<br>Pro Thr Phe Glu Thr Thr Ile<br>870 875 | | 2701 |
| ctgtataaag taattttggc aaaatataag tgatttttc tggagaattg taaaataaag | | 2761 |
| ttttctattt ttccttaaaa aaaaaaccgg aattccgggc ttgggaggct gaggcaggag | | 2821 |
| actcgcttga acccgggagg cagaggttgc agtgagccaa gattgcgcca ttgcactcca | | 2881 |
| gagcctgggt gacagagcaa gactacatct caaaaaataa ataaataaaa taaaagtaac | | 2941 |
| aataaaaata aaaagaacag cagagagaat gagcaaggag aaatgtcaca aactattgca | | 3001 |
| aaatactgtt acactgggtt ggctctccaa gaagatactg gaatctcttc agccatttgc | | 3061 |
| ttttcagaag tagaaaccag caaaccacct ctaagcggag aacatacgat tctttattaa | | 3121 |
| gtagctctgg ggaaggaaag aataaaagtt gatagctccc tgattgggaa aaatgcaca | | 3181 |
| attaataaag aatgaagatg aaagaaagca tgcttatgtt gtaacacaaa aaaaattcac | | 3241 |
| aaacgttggt ggaaggaaaa cagtatagaa acattactt taactaaaag ctggaaaaat | | 3301 |
| tttcagttgg gatgcgactg acaaaagaa cgggatttcc aggcataaag ttggcgtgag | | 3361 |
| ctacagaggg caccatgtgg ctcagtggaa gacccttcaa gattcaaagt tccatttgac | | 3421 |
| agagcaaagg cacttcgcaa ggagaagggt ttaaattatg ggtccaaaag ccaagtggta | | 3481 |
| aagcgagcaa tttgcagcat aactgcttct cctagacagg gctgagtggg caaaatacga | | 3541 |

-continued

```
cagtacacac agtgactatt agccactgcc agaaacaggc tgaacagccc tgggagacaa    3601
gggaaggcag gtggtgggag ttgttcatgg agagaaagga gagttttaga accagcacat    3661
ccactggaga tgctgggcca ccagacccct cccagtcaat aaagtctggt gcctcatttg    3721
atctcagcct catcatgacc ctggagagac cctgatacca tctgccagtc cccgacagct    3781
taggcactcc ttgccatcaa cctgaccccc cgagtggttc tccaggctcc ctgccccacc    3841
cattcaggcc ggaattc                                                   3858
```

<210> SEQ ID NO 2
<211> LENGTH: 875
<212> TYPE: PRT
<213> ORGANISM: Homo sapiens
<220> FEATURE:
<221> NAME/KEY: misc_feature
<222> LOCATION: (1)...(875)
<223> OTHER INFORMATION: 161P2F10B variant 2

<400> SEQUENCE: 2

```
Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Arg Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
```

```
              290                 295                 300
Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
                    340                 345                 350

Met Glu Gly Leu Lys Gln Arg Asn Leu His Asn Cys Val Asn Ile Ile
                355                 360                 365

Leu Leu Ala Asp His Gly Met Asp Gln Thr Tyr Cys Asn Lys Met Glu
    370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                    405                 410                 415

Ser Phe Asn Ser Glu Glu Ile Val Arg Asn Leu Ser Cys Arg Lys Pro
                420                 425                 430

Asp Gln His Phe Lys Pro Tyr Leu Thr Pro Asp Leu Pro Lys Arg Leu
                    435                 440                 445

His Tyr Ala Lys Asn Val Arg Ile Asp Lys Val His Leu Phe Val Asp
    450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                    485                 490                 495

Leu Ala His Gly Pro Ser Phe Lys Glu Lys Thr Glu Val Glu Pro Phe
                500                 505                 510

Glu Asn Ile Glu Val Tyr Asn Leu Met Cys Asp Leu Leu Arg Ile Gln
                    515                 520                 525

Pro Ala Pro Asn Asn Gly Thr His Gly Ser Leu Asn His Leu Leu Lys
    530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                    565                 570                 575

Cys Pro His Leu Gln Asn Ser Thr Gln Leu Glu Gln Val Asn Gln Met
                580                 585                 590

Leu Asn Leu Thr Gln Glu Glu Ile Thr Ala Thr Val Lys Val Asn Leu
                    595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                    645                 650                 655

Leu Pro Pro Thr Val Pro Asp Cys Leu Arg Ala Asp Val Arg Val Pro
                660                 665                 670

Pro Ser Glu Ser Gln Lys Cys Ser Phe Tyr Leu Ala Asp Lys Asn Ile
                    675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720
```

```
Phe Arg Lys Met Trp Asp Tyr Phe His Ser Val Leu Ile Lys His
            725                 730                 735

Ala Thr Glu Arg Asn Gly Val Asn Val Val Ser Gly Pro Ile Phe Asp
        740                 745                 750

Tyr Asn Tyr Asp Gly His Phe Asp Ala Pro Asp Glu Ile Thr Lys His
            755                 760                 765

Leu Ala Asn Thr Asp Val Pro Ile Pro Thr His Tyr Phe Val Val Leu
        770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Arg Phe
                820                 825                 830

Thr Ala His Ile Ala Arg Val Arg Asp Val Glu Leu Leu Thr Gly Leu
            835                 840                 845

Asp Phe Tyr Gln Asp Lys Val Gln Pro Val Ser Glu Ile Leu Gln Leu
        850                 855                 860

Lys Thr Tyr Leu Pro Thr Phe Glu Thr Thr Ile
865                 870                 875

<210> SEQ ID NO 3
<211> LENGTH: 1440
<212> TYPE: DNA
<213> ORGANISM: Homo sapiens
<220> FEATURE:
<221> NAME/KEY: misc_feature
<222> LOCATION: (1)...(1440)
<223> OTHER INFORMATION: H16-7.8 heavy chain
<220> FEATURE:
<221> NAME/KEY: CDS
<222> LOCATION: (34)...(1440)

<400> SEQUENCE: 3
tttctgagag tcctggacct cctgtgcaag aac atg aaa cac ctg tgg ttc ttc      54
                                    Met Lys His Leu Trp Phe Phe
                                     1               5 ctc ctg ctg gtg gca gct ccc aga tgg gtc ctg tcc cag gtg cag ctg     102
Leu Leu Leu Val Ala Ala Pro Arg Trp Val Leu Ser Gln Val Gln Leu
         10                  15                  20 cag gag tcg ggc cca gga ctg gtg aag cct tca cag acc ctg tcc ctc     150
Gln Glu Ser Gly Pro Gly Leu Val Lys Pro Ser Gln Thr Leu Ser Leu
 25                  30                  35 acc tgc act gtc tct ggt ggc tcc atc agc agt ggt ggt tac tac tgg     198
Thr Cys Thr Val Ser Gly Gly Ser Ile Ser Ser Gly Gly Tyr Tyr Trp
 40                  45                  50                  55 agc tgg atc cgc cag cac cca ggg aag ggc ctg gag tgg att ggg atc     246
Ser Trp Ile Arg Gln His Pro Gly Lys Gly Leu Glu Trp Ile Gly Ile
                 60                  65                  70 atc tat tac agt ggg agc acc tac tac aac ccg tcc ctc aag agt cga     294
Ile Tyr Tyr Ser Gly Ser Thr Tyr Tyr Asn Pro Ser Leu Lys Ser Arg
             75                  80                  85 gtt acc ata tca gta gac acg tct aag aac cag ttc tcc ctg aag ctg     342
Val Thr Ile Ser Val Asp Thr Ser Lys Asn Gln Phe Ser Leu Lys Leu
         90                  95                 100 aac tct gtg act gcc gcg gac acg gcc gtg ttt tac tgt gcg aga gtg     390
Asn Ser Val Thr Ala Ala Asp Thr Ala Val Phe Tyr Cys Ala Arg Val
105                 110                 115 gct ata gtg act acg atc ccg ggc ggt atg gac gtc tgg ggc caa ggg     438
Ala Ile Val Thr Thr Ile Pro Gly Gly Met Asp Val Trp Gly Gln Gly
120                 125                 130                 135
```

-continued

| | | |
|---|---|---|
| acc acg gtc acc gtc tcc tca gcc tcc acc aag ggc cca tcg gtc ttc<br>Thr Thr Val Thr Val Ser Ser Ala Ser Thr Lys Gly Pro Ser Val Phe<br>140 145 150 | 486 | |
| ccc ctg gcg ccc tgc tcc agg agc acc tcc gag agc aca gcg gcc ctg<br>Pro Leu Ala Pro Cys Ser Arg Ser Thr Ser Glu Ser Thr Ala Ala Leu<br>155 160 165 | 534 | |
| ggc tgc ctg gtc aag gac tac ttc ccc gaa ccg gtg acg gtg tcg tgg<br>Gly Cys Leu Val Lys Asp Tyr Phe Pro Glu Pro Val Thr Val Ser Trp<br>170 175 180 | 582 | |
| aac tca ggc gct ctg acc agc ggc gtg cac acc ttc cca gct gtc cta<br>Asn Ser Gly Ala Leu Thr Ser Gly Val His Thr Phe Pro Ala Val Leu<br>185 190 195 | 630 | |
| cag tcc tca gga ctc tac tcc ctc agc agc gtg gtg acc gtg ccc tcc<br>Gln Ser Ser Gly Leu Tyr Ser Leu Ser Ser Val Val Thr Val Pro Ser<br>200 205 210 215 | 678 | |
| agc aac ttc ggc acc cag acc tac acc tgc aac gta gat cac aag ccc<br>Ser Asn Phe Gly Thr Gln Thr Tyr Thr Cys Asn Val Asp His Lys Pro<br>220 225 230 | 726 | |
| agc aac acc aag gtg gac aag aca gtt gag cgc aaa tgt tgt gtc gag<br>Ser Asn Thr Lys Val Asp Lys Thr Val Glu Arg Lys Cys Cys Val Glu<br>235 240 245 | 774 | |
| tgc cca ccg tgc cca gca cca cct gtg gca gga ccg tca gtc ttc ctc<br>Cys Pro Pro Cys Pro Ala Pro Pro Val Ala Gly Pro Ser Val Phe Leu<br>250 255 260 | 822 | |
| ttc ccc cca aaa ccc aag gac acc ctc atg atc tcc cgg acc cct gag<br>Phe Pro Pro Lys Pro Lys Asp Thr Leu Met Ile Ser Arg Thr Pro Glu<br>265 270 275 | 870 | |
| gtc acg tgc gtg gtg gtg gac gtg agc cac gaa gac ccc gag gtc cag<br>Val Thr Cys Val Val Val Asp Val Ser His Glu Asp Pro Glu Val Gln<br>280 285 290 295 | 918 | |
| ttc aac tgg tac gtg gac ggc gtg gag gtg cat aat gcc aag aca aag<br>Phe Asn Trp Tyr Val Asp Gly Val Glu Val His Asn Ala Lys Thr Lys<br>300 305 310 | 966 | |
| cca cgg gag gag cag ttc aac agc acg ttc cgt gtg gtc agc gtc ctc<br>Pro Arg Glu Glu Gln Phe Asn Ser Thr Phe Arg Val Val Ser Val Leu<br>315 320 325 | 1014 | |
| acc gtt gtg cac cag gac tgg ctg aac ggc aag gag tac aag tgc aag<br>Thr Val Val His Gln Asp Trp Leu Asn Gly Lys Glu Tyr Lys Cys Lys<br>330 335 340 | 1062 | |
| gtc tcc aac aaa ggc ctc cca gcc ccc atc gag aaa acc atc tcc aaa<br>Val Ser Asn Lys Gly Leu Pro Ala Pro Ile Glu Lys Thr Ile Ser Lys<br>345 350 355 | 1110 | |
| acc aaa ggg cag ccc cga gaa cca cag gtg tac acc ctg ccc cca tcc<br>Thr Lys Gly Gln Pro Arg Glu Pro Gln Val Tyr Thr Leu Pro Pro Ser<br>360 365 370 375 | 1158 | |
| cgg gag gag atg acc aag aac cag gtc agc ctg acc tgc ctg gtc aaa<br>Arg Glu Glu Met Thr Lys Asn Gln Val Ser Leu Thr Cys Leu Val Lys<br>380 385 390 | 1206 | |
| ggc ttc tac ccc agc gac atc gcc gtg gag tgg gag agc aat ggg cag<br>Gly Phe Tyr Pro Ser Asp Ile Ala Val Glu Trp Glu Ser Asn Gly Gln<br>395 400 405 | 1254 | |
| ccg gag aac aac tac aag acc aca cct ccc atg ctg gac tcc gac ggc<br>Pro Glu Asn Asn Tyr Lys Thr Thr Pro Pro Met Leu Asp Ser Asp Gly<br>410 415 420 | 1302 | |
| tcc ttc ttc ctt tac agc aag ctc acc gtg gac aag agc agg tgg cag<br>Ser Phe Phe Leu Tyr Ser Lys Leu Thr Val Asp Lys Ser Arg Trp Gln<br>425 430 435 | 1350 | |
| cag ggg aac gtc ttc tca tgc tcc gtg atg cat gag gct ctg cac aac<br>Gln Gly Asn Val Phe Ser Cys Ser Val Met His Glu Ala Leu His Asn<br>440 445 450 455 | 1398 | |

```
cac tac acg cag aag agc ctc tcc ctg tct ccg ggt aaa taa       1440
His Tyr Thr Gln Lys Ser Leu Ser Leu Ser Pro Gly Lys
                460                 465
```

<210> SEQ ID NO 4
<211> LENGTH: 468
<212> TYPE: PRT
<213> ORGANISM: Homo sapiens
<220> FEATURE:
<221> NAME/KEY: misc_feature
<222> LOCATION: (1)...(468)
<223> OTHER INFORMATION: H16-7.8 heavy chain

<400> SEQUENCE: 4

```
Met Lys His Leu Trp Phe Phe Leu Leu Val Ala Ala Pro Arg Trp
 1               5                  10                  15

Val Leu Ser Gln Val Gln Leu Gln Glu Ser Gly Pro Gly Leu Val Lys
                20                  25                  30

Pro Ser Gln Thr Leu Ser Leu Thr Cys Thr Val Ser Gly Gly Ser Ile
            35                  40                  45

Ser Ser Gly Gly Tyr Tyr Trp Ser Trp Ile Arg Gln His Pro Gly Lys
50                  55                  60

Gly Leu Glu Trp Ile Gly Ile Ile Tyr Tyr Ser Gly Ser Thr Tyr Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Asn Ser Val Thr Ala Ala Asp Thr Ala
            100                 105                 110

Val Phe Tyr Cys Ala Arg Val Ala Ile Val Thr Thr Ile Pro Gly Gly
        115                 120                 125

Met Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335
```

```
Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
            355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 5
<211> LENGTH: 744
<212> TYPE: DNA
<213> ORGANISM: Homo sapiens
<220> FEATURE:
<221> NAME/KEY: misc_feature
<222> LOCATION: (1)...(744)
<223> OTHER INFORMATION: H16-7.8 light chain
<220> FEATURE:
<221> NAME/KEY: CDS
<222> LOCATION: (43)...(744)

<400> SEQUENCE: 5
aggagtagaa aatgagcaaa actgacaagt caaggcagga ag atg ttg cca tca          54
                                              Met Leu Pro Ser
                                                1 caa ctc att ggg ttt ctg ctg ctc tgg gtt cca gcc tcc agg ggt gaa        102
Gln Leu Ile Gly Phe Leu Leu Leu Trp Val Pro Ala Ser Arg Gly Glu
 5                  10                  15                  20 att gtg ctg act cag tct cca gac ttt cag tct gtg act cca aag gag        150
Ile Val Leu Thr Gln Ser Pro Asp Phe Gln Ser Val Thr Pro Lys Glu
                25                  30                  35 aaa gtc acc atc acc tgc cgg gcc agt cag agc att ggt att agc tta        198
Lys Val Thr Ile Thr Cys Arg Ala Ser Gln Ser Ile Gly Ile Ser Leu
            40                  45                  50 cac tgg tac cag cag aaa cca gat cag tct cca aag ctc ctc atc aag        246
His Trp Tyr Gln Gln Lys Pro Asp Gln Ser Pro Lys Leu Leu Ile Lys
        55                  60                  65 tat gct tcc cag tcc ttc tca ggg gtc ccc tcg agg ttc agt ggc agt        294
Tyr Ala Ser Gln Ser Phe Ser Gly Val Pro Ser Arg Phe Ser Gly Ser
    70                  75                  80 gga tct ggg aca gat ttc acc ctc acc atc aat agc ctg gaa gct gaa        342
Gly Ser Gly Thr Asp Phe Thr Leu Thr Ile Asn Ser Leu Glu Ala Glu
85                  90                  95                 100 gat gct gca acg tat tac tgt cat cag agt agg agt ttc ccg tgg acg        390
Asp Ala Ala Thr Tyr Tyr Cys His Gln Ser Arg Ser Phe Pro Trp Thr
                105                 110                 115 ttc ggc caa ggg acc aag gtg gaa atc aaa cga act gtg gct gca cca        438
Phe Gly Gln Gly Thr Lys Val Glu Ile Lys Arg Thr Val Ala Ala Pro
            120                 125                 130 tct gtc ttc atc ttc ccg cca tct gat gag cag ttg aaa tct gga act        486
Ser Val Phe Ile Phe Pro Pro Ser Asp Glu Gln Leu Lys Ser Gly Thr
```

```
                135                 140                 145
gcc tct gtt gtg tgc ctg ctg aat aac ttc tat ccc aga gag gcc aaa       534
Ala Ser Val Val Cys Leu Leu Asn Asn Phe Tyr Pro Arg Glu Ala Lys
    150                 155                 160 gta cag tgg aag gtg gat aac gcc ctc caa tcg ggt aac tcc cag gag       582
Val Gln Trp Lys Val Asp Asn Ala Leu Gln Ser Gly Asn Ser Gln Glu
165                 170                 175                 180 agt gtc aca gag cag gac agc aag gac agc acc tac agc ctc agc agc       630
Ser Val Thr Glu Gln Asp Ser Lys Asp Ser Thr Tyr Ser Leu Ser Ser
                185                 190                 195 acc ctg acg ctg agc aaa gca gac tac gag aaa cac aaa gtc tac gcc       678
Thr Leu Thr Leu Ser Lys Ala Asp Tyr Glu Lys His Lys Val Tyr Ala
            200                 205                 210 tgc gaa gtc acc cat cag ggc ctg agc tcg ccc gtc aca aag agc ttc       726
Cys Glu Val Thr His Gln Gly Leu Ser Ser Pro Val Thr Lys Ser Phe
        215                 220                 225 aac agg gga gag tgt tag                                               744
Asn Arg Gly Glu Cys
    230

<210> SEQ ID NO 6
<211> LENGTH: 233
<212> TYPE: PRT
<213> ORGANISM: Homo sapiens
<220> FEATURE:
<221> NAME/KEY: misc_feature
<222> LOCATION: (1)...(233)
<223> OTHER INFORMATION: H16-7.8 light chain

<400> SEQUENCE: 6

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ile Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Thr Tyr Tyr Cys His Gln Ser Arg Ser
            100                 105                 110

Phe Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220
```

```
Thr Lys Ser Phe Asn Arg Gly Glu Cys
225                 230
```

```
<210> SEQ ID NO 7
<211> LENGTH: 468
<212> TYPE: PRT
<213> ORGANISM: Homo sapiens
<220> FEATURE:
<221> NAME/KEY: misc_feature
<222> LOCATION: (1)...(468)
<223> OTHER INFORMATION: H16-7.8 heavy chain

<400> SEQUENCE: 7

Met Lys His Leu Trp Phe Phe Leu Leu Val Ala Ala Pro Arg Trp
  1               5                  10                  15

Val Leu Ser Gln Val Gln Leu Gln Glu Ser Gly Pro Gly Leu Val Lys
         20                  25                  30

Pro Ser Gln Thr Leu Ser Leu Thr Cys Thr Val Ser Gly Gly Ser Ile
         35                  40                  45

Ser Ser Gly Gly Tyr Tyr Trp Ser Trp Ile Arg Gln His Pro Gly Lys
 50                  55                  60

Gly Leu Glu Trp Ile Gly Ile Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Asn Ser Val Thr Ala Ala Asp Thr Ala
            100                 105                 110

Val Phe Tyr Cys Ala Arg Val Ala Ile Val Thr Thr Ile Pro Gly Gly
            115                 120                 125

Met Asp Val Trp Gly Gln Gly Thr Thr Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Gln Phe Asn Trp Tyr Val Asp Gly Val Glu
290                 295                 300

Val His Asn Ala Lys Thr Lys Pro Arg Glu Glu Gln Phe Asn Ser Thr
305                 310                 315                 320

Phe Arg Val Val Ser Val Leu Thr Val His Gln Asp Trp Leu Asn
                325                 330                 335

Gly Lys Glu Tyr Lys Cys Lys Val Ser Asn Lys Gly Leu Pro Ala Pro
            340                 345                 350
```

```
Ile Glu Lys Thr Ile Ser Lys Thr Lys Gly Gln Pro Arg Glu Pro Gln
            355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 8
<211> LENGTH: 233
<212> TYPE: PRT
<213> ORGANISM: Homo sapiens
<220> FEATURE:
<221> NAME/KEY: misc_feature
<222> LOCATION: (1)...(233)
<223> OTHER INFORMATION: H16-7.8 light chain

<400> SEQUENCE: 8

Met Leu Pro Ser Gln Leu Ile Gly Phe Leu Leu Leu Trp Val Pro Ala
  1               5                  10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ile Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Thr Tyr Tyr Cys His Gln Ser Arg Ser
            100                 105                 110

Phe Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
```

-continued

<210> SEQ ID NO 9
<211> LENGTH: 7
<212> TYPE: PRT
<213> ORGANISM: Artificial Sequence
<220> FEATURE:
<223> OTHER INFORMATION: synthetically constructed light chain peptide

<400> SEQUENCE: 9

Ser Phe Asn Arg Gly Glu Cys
 1               5

<210> SEQ ID NO 10
<211> LENGTH: 25
<212> TYPE: PRT
<213> ORGANISM: Artificial Sequence
<220> FEATURE:
<223> OTHER INFORMATION: synthetically constructed heavy chain peptide

<400> SEQUENCE: 10

Cys Cys Val Glu Cys Pro Pro Cys Pro Ala Pro Pro Val Gly Pro Ser
 1               5                  10                  15

Val Phe Leu Phe Pro Pro Lys Pro Lys
             20                  25

<210> SEQ ID NO 11
<211> LENGTH: 369
<212> TYPE: DNA
<213> ORGANISM: Homo sapiens
<220> FEATURE:
<221> NAME/KEY: misc_feature
<222> LOCATION: (1)...(369)
<223> OTHER INFORMATION: H16-7.8 heavy chain variable region

<400> SEQUENCE: 11
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggatcatct attacagtgg gagcacctac     180
tacaacccgt ccctcaagag tcgagttacc atatcagtag acacgtctaa gaaccagttc     240
tccctgaagc tgaactctgt gactgccgcg gacacggccg tgttttactg tgcgagagtg     300
gctatagtga ctacgatccc gggcggtatg gacgtctggg gccaagggac cacggtcacc     360
gtctcctca                                                            369

<210> SEQ ID NO 12
<211> LENGTH: 452
<212> TYPE: DNA
<213> ORGANISM: Homo sapiens
<220> FEATURE:
<221> NAME/KEY: misc_feature
<222> LOCATION: (1)...(452)
<223> OTHER INFORMATION: H16-7.8 light chain variable region

<400> SEQUENCE: 12
gaaattgtgc tgactcagtc tccagacttt cagtctgtga ctccaaagga gaaagtcacc      60
atcacctgcc gggccagtca gagcattggt attagcttac actggtacca gcagaaacca     120
gatcagtctc caaagctcct catcaagtat gcttcccagt ccttctcagg ggtccctcg      180 aggttcagtg gcagtggatc tgggacagat ttcaccctca ccatcaatag cctggaagct     240
gaagatgctg caacgtatta ctgtcatcag agtaggagtt cccgtggac gttcggccaa     300 gggaccaagg tggaaatcaa acgaactgtg gctgcaccat ctgtcttcat cttcccgcca     360

```
tctgatgagc agttgaaatc tggaactgcc tctgttgtgt gcctgctgaa taacttctat    420
cccagagagg ccaaagtaca gtggaaggtg ga                                  452
```